US011859250B1

(12) United States Patent
Rothenberg et al.

(10) Patent No.: US 11,859,250 B1
(45) Date of Patent: Jan. 2, 2024

(54) METHODS FOR TREATING EOSINOPHILIC ESOPHAGITIS

(71) Applicant: CHILDREN'S HOSPITAL MEDICAL CENTER, Cincinnati, OH (US)

(72) Inventors: Marc E. Rothenberg, Cincinnati, OH (US); Tetsuo Shoda, Cincinnati, OH (US); Ting Wen, Cincinnati, OH (US)

(73) Assignee: CHILDREN'S HOSPITAL MEDICAL CENTER, Cincinnati, OH (US)

( * ) Notice: Subject to any disclaimer, the term of this patent is extended or adjusted under 35 U.S.C. 154(b) by 695 days.

(21) Appl. No.: 16/281,750

(22) Filed: Feb. 21, 2019

Related U.S. Application Data

(60) Provisional application No. 62/634,446, filed on Feb. 23, 2018.

(51) Int. Cl.
C12Q 1/68 (2018.01)
C12Q 1/6883 (2018.01)

(52) U.S. Cl.
CPC ..... *C12Q 1/6883* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

| | | |
|---|---|---|
| 4,376,110 A | 3/1983 | David et al. |
| 4,522,811 A | 6/1985 | Eppstein et al. |
| 4,675,604 A | 6/1987 | Moyer et al. |
| 4,675,904 A | 6/1987 | Silverman |
| 5,148,483 A | 9/1992 | Silverman |
| 5,288,644 A | 2/1994 | Beavis et al. |
| 5,412,073 A | 5/1995 | Kalsheker |
| 5,445,934 A | 8/1995 | Fodor et al. |
| 5,530,101 A | 6/1996 | Queen et al. |
| 5,700,637 A | 12/1997 | Southern |
| 5,744,305 A | 4/1998 | Fodor et al. |
| 5,888,510 A | 3/1999 | Kishimoto et al. |
| 5,945,334 A | 8/1999 | Besemer et al. |
| 5,976,081 A | 11/1999 | Silverman |
| 6,054,270 A | 4/2000 | Southern |
| 6,300,063 B1 | 10/2001 | Lipshutz et al. |
| 6,403,782 B1 | 6/2002 | Luster et al. |
| 6,429,027 B1 | 8/2002 | Chee et al. |
| 6,733,977 B2 | 5/2004 | Besemer et al. |
| 6,780,973 B1 | 8/2004 | Luster et al. |
| 6,825,350 B2 | 11/2004 | Crooks et al. |
| 6,858,394 B1 | 2/2005 | Chee et al. |
| 7,364,858 B2 | 4/2008 | Barany et al. |
| 7,514,209 B2 | 4/2009 | Dai et al. |
| 7,582,620 B2 | 9/2009 | Lew |
| 7,592,326 B2 | 9/2009 | Karaolis |
| 7,879,547 B2 | 2/2011 | Rothenberg et al. |
| 8,030,003 B2 | 10/2011 | Rothenberg |
| 8,409,565 B2 | 4/2013 | Levi-Schaffer et al. |
| 9,260,756 B2 | 2/2016 | Rothenberg et al. |
| 9,345,763 B2 | 5/2016 | Rothenberg et al. |
| 9,517,238 B2 | 12/2016 | Rochman et al. |
| 9,624,545 B2 | 4/2017 | Rothenberg et al. |
| 9,691,411 B2 | 6/2017 | Scherer et al. |
| 9,803,244 B2 | 10/2017 | Rothenberg et al. |
| 9,928,344 B2 | 3/2018 | Rothenberg et al. |
| 9,982,303 B2 | 5/2018 | Rothenberg |
| 10,155,985 B2 | 12/2018 | Rothenberg et al. |
| 10,294,517 B2 | 5/2019 | Rothenberg et al. |
| 10,422,004 B2 | 9/2019 | Rothenberg et al. |
| 10,821,094 B2 | 11/2020 | Azouz et al. |
| 2002/0077825 A1 | 6/2002 | Silverman et al. |
| 2003/0078768 A1 | 4/2003 | Silverman et al. |
| 2003/0157479 A1 | 8/2003 | Bachmann et al. |
| 2003/0167189 A1 | 9/2003 | Lutgen et al. |
| 2003/0194404 A1 | 10/2003 | Greenfeder et al. |
| 2004/0033502 A1 | 2/2004 | Williams et al. |
| 2004/0141951 A1 | 7/2004 | Rothenberg et al. |
| 2005/0163764 A1 | 7/2005 | Medzhitov et al. |
| 2007/0059720 A9 | 3/2007 | Fuqua et al. |
| 2007/0233468 A1 | 10/2007 | Ozdas et al. |
| 2007/0233498 A1 | 10/2007 | Silverman et al. |
| 2008/0187908 A1 | 8/2008 | Adra |
| 2008/0201280 A1 | 8/2008 | Martin et al. |
| 2009/0233275 A1 | 9/2009 | Rothenberg |
| 2009/0269774 A1 | 10/2009 | Rothenberg et al. |
| 2010/0151472 A1 | 6/2010 | Mcgarrigle et al. |
| 2010/0240965 A1 | 9/2010 | Furuta et al. |
| 2010/0262603 A1 | 10/2010 | Odom et al. |

(Continued)

FOREIGN PATENT DOCUMENTS

CN 101275941 A 10/2008
EP 0619321 A1 10/1994

(Continued)

OTHER PUBLICATIONS

Kalinin et al.; Future Medicine, vol. 19, pp. 629-650, 2018.*
Siddique et al.; Human Pathology, vol. 68, pp. 79-86, 2017.*
Butz et al.; Gastroenterology, vol. 147, pp. 324-333, 2014.*
Molina-Infante et al.; Gut, 2016; 65:524-531.*
Dellon et al.; Gastrointest Endox, 2010, 71:706-7012.*
Accession No. E-MEXP-3298.
Accession No. E-MEXP-3345.
Accession No. E-MEXP-3346.
Accession No. E-MEXP-3350.
Accession No. E-MEXP-3351.
Accession No. E-MEXP-3353.
Asthma and Immunology, American College of Allergy, Oct. 10, 2017.
Eosinophilic Esophagitis, American College of Gastroenterology, Oct. 10, 2017.

(Continued)

*Primary Examiner* — Jehanne S Sitton
(74) *Attorney, Agent, or Firm* — KDW FIRM PLLC

(57) ABSTRACT

The present invention relates to methods for identifying an EoE endotype of a patient and treating the patient with one or more therapies targeted to the patient's disease endotype; and related methods for stratifying patients for clinical trials.

18 Claims, 18 Drawing Sheets

(56) References Cited

U.S. PATENT DOCUMENTS

| | | |
|---|---|---|
| 2011/0123530 A1 | 5/2011 | Arron et al. |
| 2011/0144183 A1 | 6/2011 | Paquet et al. |
| 2011/0195500 A1 | 8/2011 | Rothenberg |
| 2011/0301046 A1 | 12/2011 | Rothenberg et al. |
| 2012/0004205 A1 | 1/2012 | Rothenberg |
| 2012/0041911 A1 | 2/2012 | Pestian et al. |
| 2012/0283117 A1 | 11/2012 | Rothenberg |
| 2012/0288068 A1 | 11/2012 | Jaiswal et al. |
| 2013/0035961 A1 | 2/2013 | Yegnanarayanan |
| 2013/0065972 A1 | 3/2013 | Dent et al. |
| 2013/0324435 A1 | 12/2013 | Rothenberg et al. |
| 2014/0073801 A1 | 3/2014 | Storer et al. |
| 2014/0113372 A1 | 4/2014 | Haque et al. |
| 2014/0228301 A1 | 8/2014 | Meade et al. |
| 2014/0228315 A1 | 8/2014 | Rothenberg et al. |
| 2014/0286896 A1 | 9/2014 | Rothenberg et al. |
| 2014/0328861 A1 | 11/2014 | Payton et al. |
| 2014/0343255 A1 | 11/2014 | Gonzalez et al. |
| 2015/0038552 A1 | 2/2015 | Rothenberg et al. |
| 2015/0045334 A1 | 2/2015 | Rothenberg et al. |
| 2015/0182499 A1 | 7/2015 | Reboud-Ravaux et al. |
| 2015/0355180 A1 | 12/2015 | Resnick et al. |
| 2016/0129012 A1 | 5/2016 | Rochman et al. |
| 2016/0177394 A1 | 6/2016 | Rothenberg et al. |
| 2016/0180041 A1 | 6/2016 | Pestian et al. |
| 2016/0213681 A1 | 7/2016 | Santus et al. |
| 2016/0264658 A1 | 9/2016 | Ahmed et al. |
| 2016/0304960 A1 | 10/2016 | Rothenberg |
| 2016/0312282 A1 | 10/2016 | Rothenberg et al. |
| 2017/0061073 A1 | 3/2017 | Sadhasivam |
| 2017/0067111 A1 | 3/2017 | Rothenberg et al. |
| 2017/0183719 A1 | 6/2017 | Rothenberg et al. |
| 2017/0199191 A1 | 7/2017 | Fulkerson |
| 2017/0233813 A1 | 8/2017 | Rothenberg et al. |
| 2019/0000799 A1 | 1/2019 | Azouz et al. |
| 2019/0046444 A1 | 2/2019 | Konduri et al. |
| 2020/0338043 A1 | 10/2020 | Azouz et al. |
| 2021/0080453 A1 | 3/2021 | Rothenberg et al. |

FOREIGN PATENT DOCUMENTS

| | | |
|---|---|---|
| EP | 0619321 B1 | 1/1999 |
| EP | 0949271 A1 | 10/1999 |
| WO | 8910977 A1 | 11/1989 |
| WO | 9937319 A1 | 7/1999 |
| WO | 2005007175 A2 | 1/2005 |
| WO | 2005033134 A2 | 4/2005 |
| WO | 2005106492 A2 | 11/2005 |
| WO | 2005106492 A3 | 5/2006 |
| WO | 2006083390 A2 | 8/2006 |
| WO | 2006119343 A1 | 11/2006 |
| WO | 2006083390 A3 | 12/2006 |
| WO | 2009015434 A1 | 2/2009 |
| WO | 2009018493 A1 | 2/2009 |
| WO | 2009061819 A1 | 5/2009 |
| WO | 2009089062 A2 | 7/2009 |
| WO | 2009089062 A3 | 9/2009 |
| WO | 2009089062 A8 | 9/2010 |
| WO | 2010126867 A1 | 11/2010 |
| WO | 2012025765 A1 | 3/2012 |
| WO | 2012094643 A2 | 7/2012 |
| WO | 2012094643 A3 | 11/2012 |
| WO | 2012174549 A2 | 12/2012 |
| WO | 2012177945 A2 | 12/2012 |
| WO | 2012178188 A2 | 12/2012 |
| WO | 2012174549 A9 | 2/2013 |
| WO | 2012177945 A3 | 2/2013 |
| WO | 2013082308 A1 | 6/2013 |
| WO | 2012178188 A3 | 7/2013 |
| WO | 2013126834 A1 | 8/2013 |
| WO | 2013155010 A1 | 10/2013 |
| WO | 2014059178 A1 | 4/2014 |
| WO | 2014190269 A1 | 11/2014 |
| WO | 2015017731 A1 | 2/2015 |
| WO | 2015127379 A1 | 8/2015 |
| WO | 2015142739 A1 | 9/2015 |
| WO | 2016023026 A1 | 2/2016 |
| WO | 2016196146 A1 | 12/2016 |
| WO | 2017048860 A1 | 3/2017 |
| WO | 2017123401 A1 | 7/2017 |
| WO | 2019204580 A1 | 10/2019 |

OTHER PUBLICATIONS

Extended European Search Report for EP Application No. 15828951. 2, dated Nov. 16, 2017, 8 pages.
Extended European Search Report issued in European Application No. 16885429.7, dated Jul. 23, 2019, 15 pages.
Extended European Search Report dated Feb. 13, 2015 for European Application No. EP12802640, filed on Dec. 27, 2012.
Zimmerman et al. (Feb. 2003) "Chemokines in Asthma: Cooperative Interaction between Chemokines and IL-13", The Journal of Allergy and Clinical Immunology, 111(2):227-242.
International Preliminary Report on Patentability received for PCT International Application No. PCT/US16/68238, dated Jul. 26, 2018, 7 pages.
International Search Report and Written Opinion of the International Searching Authority dated Jul. 8, 2019 for International Application No. PCT/US2019/028076, dated Apr. 18, 2019, 15 pages.
International Search Report for PCT Application No. PCT/US2006/016948, filed May 3, 2006, 1 page.
International search report issued in PCT/US2015/020768, dated Jun. 12, 2015.
International Search Report dated Dec. 27, 2012 for International Application No. PCT/US2012/043640, filed Jun. 21, 2012.
International Search Report dated Mar. 25, 2013 for International Application No. PCT/US2012/044061, filed Jun. 25, 2012.
International Search Report dated Sep. 9, 2016 for International Application No. PCT/US2016/034185, filed May 25, 2016, 8 pages.
International Search Report received for PCT Patent International Application No. PCT/US16/68238, dated Mar. 27, 2017, 8 pages.
International Search Report received for PCT Patent International Application No. PCT/US2014/039357, dated Sep. 24, 2014, 8 pages.
International Search Report received for PCT Patent International Application No. PCT/US2014/049301, dated Dec. 8, 2014, 8 pages.
International Search Report received for PCT Patent International Application No. PCT/US2015/017134, dated May 6, 2015, 11 pages.
International Search Report received in connection with PCT/US2005/044456, dated Dec. 7, 2006, 7 pages.
Mus Musculus TaqMan Probe Mm00446968_m1 for Hypoxanthine Guanine Phosphoribosyl Transferase (Hprt).
Mus musculus TaqMan probe Mm01216172_m1 for chemokine (C-C motif) receptor 3 (Ccr3).
Notes for 5th International Eosinophil Symposium, Jul. 2007.
Zimmermann et al. (Apr. 30, 1999) "CC Chemokine Receptor-3 Undergoes Prolonged Ligand-induced Internalization", Journal of Biological Chemistry, 274(18):12611-12618.
The Merck Manual, 1992, 1229-1230 & 1233.
The Merck Manual, 1992, 646-649.
Transcription Profiling of *Drosophila* 40 Homozygous Raleigh Lines to Understand the Genetic Basis of Complex Traits in *Drosophila*, Accession No. E-MEXP-1594.
Abidi et al. (2008) "Eosinopenia is a Reliable Marker of Sepsis on Admission to Medical Intensive Care Units", Critical Care, R59, 12(2):10 pages.
Abonia et al. (2012) "Eosinophilic Esophagitis: Rapidly Advancing Insights", Annual Review of Medicine, 63:421-434.
Abonia et al. (Jul. 2010) "Involvement of Mast Cells in Eosinophilic Esophagitis", The Journal of Allergy and Clinical Immunology, 126(1):140-149.
Aceves et al. (Jan. 2007) "Esophageal Remodeling in Pediatric Eosinophilic Esophagitis", The Journal of Allergy and Clinical Immunology, 119(1):206-212.
Aceves et al. (Dec. 2010) "Mast Cells Infiltrate the Esophageal Smooth Muscle in Patients with Eosinophilic Esophagitis, Express

(56) References Cited

OTHER PUBLICATIONS

TGF-β1, and Increase Esophageal Smooth Muscle Contraction", The Journal of Allergy and Clinical Immunology, e4, 126(6): 1198-204.
Ackerman et al. (Apr. 26, 2002) "Charcot-Leyden Crystal Protein (Galectin-10) Is Not a Dual Function Galectin with Lysophospholipase Activity but Binds a Lysophospholipase Inhibitor in a Novel Structural Fashion", Journal of Biological Chemistry, 277(17):14859-14868.
Adachi et al. (Dec. 15, 2007) "Transduction of Phosphatase and Tensin Homolog Deleted on Chromosome 10 into Eosinophils Attenuates Survival, Chemotaxis, and Airway Inflammation", The Journal of Immunology, 179 (12):8105-8111.
Akuthota et al. (2011) "Eosinophils: Offenders or General Bystanders in Allergic Airway Disease and Pulmonary Immunity?", Journal of Innate Immunity, 3(2):113-119.
Alexander Jeffreya (May 2014) "Topical Steroid Therapy for Eosinophilic Esophagitis", Gastroenterology & Hepatology, 10(5):327-329.
Allakhverdi et al. (Feb. 2009) "CD34+ Hemopoietic Progenitor Cells are Potent Effectors of Allergic Inflammation", Journal of Allergy and Clinical Immunology, 123(2):472-478.
Anderson et al. (Sep. 2011) "Evaluation of a morphine maturation model for the prediction of morphine clearance in children", British Journal of Clinical Pharmacology, 72(3):518-520.
Andrews, "Allosteric Small Molecule Inhibitors of the NGF/TrkA Pathway A New Approach to Treating Inflammatory Pain", Available at: http://www.arraybiopharma.com/files/6313/9810/8021/PubAttachment587.pdf, 33 pages.
Angus et al. (Jul. 2009) "Epidemiology of Severe Sepsis in the United States: Analysis of Incidence, Outcome, and Associated Costs of Care", Critical Care Medicine, 29(7):1303-1310.
Anonymous (Jul. 7, 2015) "TaqMan(R) Human Micro RNA Arrays", 2 pages.
Anthony et al. (Dec. 2007) "Protective Immune Mechanisms in Helminth Infection", Nature Reviews Immunology, 7(12):975-987.
April et al. (Dec. 3, 2009) "Whole-Genome Gene Expression Profiling of Formalin-Fixed, Paraffin-Embedded Tissue Samples", Plos One, e8162, 4(12): 10 pages.
Arefi et al. (Sep. 2012) "Response to Imatinib Mesylate in Patients with Hypereosinophilic Syndrome", International Journal of Hematology, 96(3):320-326.
Armour et al. (Mar. 31, 2010) "Expression of Human FcγRIIIa as a GPI-linked Molecule on CHO Cells to Enable Measurement of Human IgG Binding", Journal of Immunological Methods, 354(1-2):20-33.
Arroyo et al. (Mar. 22, 2011) "Argonaute2 Complexes Carry a Population of Circulating MicroRNAs Independent of Vesicles in Human Plasma", Proceedings of the National Academy of Sciences of the United States of America, 108 (12):5003-5008.
Collins, Mh et al., (2017). "Newly developed and validated eosinophilic esophagitis histology scoring system and evidence that it outperforms peak eosinophil count for disease diagnosis and monitoring." *Dis. Esophagus* 30:1-8.
Wechsler JB., et al., (2018). "Esophagitis reference score accurately identifies disease activity and treatment effects in children." *Clin. Gastroenterol. Hepatol.* 16(7):1056-1063.
Wen, T. et al., (2013). "Molecular diagnosis of eosinophilic esophagitis by gene expression profiling." *Gastroenterol.* 145(6):1289-1299.
Rothenberg, ME., (2016). "Humanized anti-IL-5 antibody therapy." *Cell* 165(Apr. 21, 2016) 509.
Lexmond, WS., et al., (2013). "Elevated levels of leukotriene $C^4$ synthase mRNA distinguish a subpopulation of eosinophilic oesophagitis patients." *Clin. Exp. Allergy*. 43(8):902-913.
Sato et al. (May 2011) "MicroRNAs and Epigenetics", The FEBS Journal, 278(10):1598-1609.
Sayed et al. (Jul. 2011) "MicroRNAs in Development and Disease", Physiological Reviews, 91(3):827-887.

Scherer et al. (2013) "Investigating the Speech Characteristics of Suicidal Adolescents", International Conference on Acoustics, Speech and Signal Processing, 5 pages.
Schmid-Grendelmeier et al. (Jul. 15, 2002) "Eosinophils Express Functional IL-13 in Eosinophilic Inflammatory Diseases", Journal of Immunology, 169(2):1021-1027.
Schoneberg et al. (Mar. 2, 2018) "Structural Basis of G Protein-coupled Receptor Function", Molecular and Cellular Endocrinology, 151(1-2):181-193.
Schultz et al. (May 26, 1998) "SMART, A Simple Modular Architecture Research Tool: Identification of Signaling Domains", Proceedings of the National Academy of Sciences of the United States of America, 95(11):5857-5864.
Sehmi et al. (Nov. 15, 1997) "Allergen-induced Increases in IL-5 Receptor Alpha-subunit Expression on Bone Marrow-derived CD34+ Cells from Asthmatic Subjects. A Novel Marker of Progenitor Cell Commitment Towards Eosinophilic Differentiation", Journal of Clinical Investigation, 100(10):2466-2475.
Sexton et al. (Sep. 2009) "Recent Advances in our Understanding of Peptide Hormone Receptors and RAMPS", Current Opinion in Drug Discovery & Development, 2(5):440-448.
Shaaban et al. (Dec. 2010) "Eosinopenia: Is it a Good Marker of Sepsis in Comparison to Procalcitonin and C-reactive Protein Levels for Patients Admitted to a Critical Care Unit in an Urban Hospital?", Journal of Critical Care, 25 (4):570-575.
Shah et al. (Mar. 2009) "Histopathologic Variability in Children with Eosinophilic Esophagitis", The American Journal of Gastroenterology, 104(3):716-721.
Sharma et al. (Aug. 5, 2011) "Protein Kinase R as Mediator of the Effects of Interferon (IFN) Gamma and Tumor Necrosis Factor (TNF) Alpha on Normal and Dysplastic Hematopoiesis", Journal of Biological Chemistry, 286 (31):27506-27514.
Shen et al. (Apr. 2011) "Plasma MicroRNAs as Potential Biomarkers for Non-small-cell Lung Cancer", Laboratory Investigation, 91(4):579-587.
Sheng et al. (Jun. 2011) "The MUC13 Cell Surface Mucin Protects Against Intestinal Inflammation by Inhibiting Epithelial Cell Apoptosis", Gut, 60(12):1661-1670.
Sherrill et al. (Jul. 2011) "Genetic Dissection of Eosinophilic Esophagitis Provides Insight into Disease Pathogenesis and Treatment Strategies", The Journal of Allergy and Clinical Immunology, 128(1):23-32.
Sherrill et al. (Jul. 1, 2010) "Variants of Thymic Stromal Lymphopoietin and its Receptor Associate with Eosinophilic Esophagitis", Journal of Allergy and Clinical Immunology, 126(1):160-165.
Shinkai et al. (Aug. 1, 1999) "A Novel Human CC Chemokine, Eotaxin-3, Which Is Expressed in IL-4-Stimulated Vascular Endothelial Cells, Exhibits Potent Activity Toward Eosinophils", The Journal of Immunology, 163 (3):1602-1610.
Shinkai et al. (Nov. 2002) "N-terminal Domain of Eotaxin-3 is Important for Activation Of CC Chemokine Receptor 3", Protein Engineering, Design and Selection, 15(11):923-929.
Shoda et al. (Jan. 2020) "Molecular, Endoscopic, Histologic, and Circulating Biomarker-based Diagnosis of Eosinophilic Gastritis: Multi-site Study", The Journal of Allergy and Clinical Immunology, 145(1):255-269.
Simon et al. (Oct. 10, 2005) "Roadmap for Developing and Validating Therapeutically Relevant Genomic Classifiers", Journal of Clinical Oncology, 23(29):7332-7341.
Simonini et al. (Nov. 15, 2010) "Epigenetically Deregulated Microrna-375 is Involved in a Positive Feedback Loop with Estrogen Receptor Alpha in Breast Cancer Cells", Cancer Research, 70(22):9175-9184.
Sin et al. (Sep. 2011) "Nerve Growth Factor or IL-3 Induces more IL-13 Production from Basophils of Allergic Subjects than from Basophils of Nonallergic Subjects", The Journal of Allergy and Clinical Immunology, 108 (3):387-393.
Slonim Donnak. (Dec. 2002) "From Patterns to Pathways: Gene Expression Data Analysis Comes of Age", Nature Genetics, 32:502-508.
Smith et al. (Jun. 2010) "Insulin-Like Growth Factor-I Regulation of Immune Function: A Potential Therapeutic Target in Autoimmune Diseases?", Pharmacological Reviews, 62(2):199-236.

(56) References Cited

OTHER PUBLICATIONS

Smith et al. (Feb. 7, 2010) "MicroRNAs, Development of Barrett's Esophagus, and Progression to Esophageal Adenocarcinoma", World Journal of Gastroenterology, 16(5):531-537.
Smith et al. (Dec. 2006) "Serine Proteases, their Inhibitors and Allergy", Allergy, 61(12):1441-1447.
Sonkoly et al. (Jul. 2007) "MicroRNAs: Novel Regulators Involved in the Pathogenesis of Psoriasis?", PLoS One, e610, 2(7):8 pages.
Sonkoly et al. (Dec. 2010) "MIR-155 is Overexpressed in Patients with Atopic Dermatitis and Modulates T-cell Proliferative Responses by Targeting Cytotoxic T Lymphocyte-associated Antigen 4", The Journal of Allergy and Clinical Immunology, 126(3):581-589.
Spergel et al. (Oct. 2005) "Treatment of Eosinophilic Esophagitis with Specific Food Elimination Diet Directed by a Combination of Skin Prick and Patch Tests", Annals of Allergy, Asthma & Immunology, 95(4):336-343.
Sprenger et al. (Jan. 2009) "Eosinophilic Oesophagitis: An Enigmatic, Emerging Disease", The Netherlands Journal of Medicine, 67(1):8-12.
Spry C. (Sep. 1976) "Eosinophilia in Addison's Disease", Yale Journal of Biology and Medicine, 49(4):411-413.
Stansfield et al. (Dec. 2009) "Periostin Is a Novel Factor in Cardiac Remodeling After Experimental and Clinical Unloading of the Failing Heart", The Annals of Thoracic Surgery, 88(6): 1916-1921.
Stappert et al. (Aug. 1994) "A Short Core Region of E-cadherin is Essential for Catenin Binding and is Highly Phosphorylated", Cell Communication & Adhesion, 2(4):319-327.
Stein et al. (Jun. 2008) "Anti-IL-5 (Mepolizumab) Therapy Reduces Eosinophil Activation Ex Vivo and Increases IL-5 and IL-5 Receptor Levels", The Journal of Allergy and Clinical Immunology, 121(6):1473-1483.
Stein et al. (Nov. 2010) "Targeting Interleukin (IL) 5 for Asthma and Hypereosinophilic Diseases", Recent Patents on Inflammation & Allergy Drug Discovery, 4(3):201-209.
Stothard P. (Jun. 2000) "Javascript Programs for Analyzing and Formatting Protein and DNA Sequences", BioTechniques, 28(6);1102, 1104.
Straumann et al. (Nov. 2010) "Budesonide Is Effective in Adolescent and Adult Patients With Active Eosinophilic Esophagitis", Gastroenterology, 139(5): 1526-1537.
Straumann et al. (Feb. 2005) "Eosinophilic esophagitis: escalating epidemiology?", The Journal of Allergy and Clinical Immunology, 115(2):418-419.
Straumann Alex (Feb. 3, 2012) "Eosinophilic Esophagitis: Rapidly Emerging Disorder", Swiss Medical Weekly, w13513, 142:8 pages.
Straumann et al. (Dec. 2001) "Idiopathic Eosinophilic Esophagitis is Associated with a T(H)2-type Allergic Inflammatory Response", The Journal of Allergy and Clinical Immunology, 108(6):954-961.
Straumann et al. (May 2011) "Long-term Budesonide Maintenance Treatment is Partially Effective for Patients with Eosinophilic Esophagitis", Clinical Gastroenterology and Hepatology, 9(5):370-372.
Straumann et al. (Apr. 2012) "Pediatric and Adult Eosinophilic Esophagitis: Similarities and Differences", Allergy, 67(4):477-490.
Strausberg et al. (2002) "Reading the Molecular Signatures of Cancer", Microarrays and Cancer Research, 11-16.
Suire et al. (Apr. 2005) "p84, a New Gβγ-activated Regulatory Subunit of the Type IB Phosphoinositide 3-kinase p110γ", Current Biology, 15(6):566-570.
Svensson et al. (Apr. 2005) "Human Eosinophils Selectively Recognize and Become Activated by Bacteria Belonging to Different Taxonomic Groups", Microbes and Infection, 7(4):720-728.
Talley et al. (Jan. 1990) "Eosinophilic Gastroenteritis: A Clinicopathological Study of Patients with Disease of the Mucosa, Muscle Layer, and Subserosal Tissues", Gut, 31(1):54-58.
Tan et al. (Mar. 15, 2011) "HYAL 1 Overexpression is Correlated with the Malignant Behavior of Human Breast Cancer", International Journal of Cancer, 128(6):1303-1315.

Teitelbaum et al. (May 2002) "Eosinophilic Esophagitis in Children: Immunopathological Analysis and Response to Fluticasone Propionate", Gastroenterology, 122(5):1216-1225.
Tezza et al. (Jun. 2013) "Epigenetics of Allergy", Early Human Development, 89(Suppl 1):S20-S21.
Lu et al. (Sep. 15, 2011) "MicroRNA-21 Limits in Vivo Immune Response-mediated Activation of the IL-12/IFN-gamma Pathway, Th1 Polarization, and the Severity of Delayed-type Hypersensitivity", Journal of Immunology, 187 (16):3362-3373.
Lu et al. (Feb. 15, 2013) "miR-223 Deficiency Increases Eosinophil Progenitor Proliferation", Journal of Immunology, 190(4):1576-1582.
Lu et al. (Jul. 2012) "MiR-375 is Downregulated in Epithelial Cells after IL-13 Stimulation and Regulates an IL-13-induced Epithelial Transcriptome", Mucosal Immunology, 5(4):388-396.
Lu et al. (Mar. 22, 2013) "Targeted Ablation of miR-21 Decreases Murine Eosinophil Progenitor Cell Growth", PLoS One, e59397, 8(3):8 pages.
Lucendo et al. (Jun. 15, 2011) "Montelukast Was Inefficient in Maintaining Steroid-Induced Remission in Adult Eosinophilic Esophagitis", Digestive Diseases and Sciences, 56(12):3551-3558.
Lucendo et al. (Sep. 2008) "Treatment with Topical Steroids Downregulates IL-5, Eotaxin-1/CCL11, and Eotaxin-3/CCL26 Gene Expression in Eosinophilic Esophagitis", The American Journal of Gastroenterology, 103(9):2184-2193.
Markowitz et al. (Apr. 2003) "Elemental Diet Is an Effective Treatment for Eosinophilic Esophagitis in Children and Adolescents", The American Journal of Gastroenterology, 98(4):777-782.
Martin et al. (May 2003) "Role of Innate Immune Factors in the Adjuvant Activity of Monophosphoryl Lipid A", Infection and Immunity, 71(5):2498-2507.
Martinez-Nunez et al. (Jan. 21, 2011) "The Interleukin 13 (IL-13) Pathway in Human Macrophages is Modulated by MicroRNA-155 Via Direct Targeting of Interleukin 13 Receptor Alpha1 (IL13Ralpha1)", Journal of Biological Chemistry, 286(3): 1786-1794.
MATSUSHIMA (2010) "MicroRNAs and Esophageal Squamous Cell Carcinoma", Digestion, 82(3):38-144.
Mattes et al. (Nov. 3, 2009) "Antagonism of microRNA-126 Suppresses the Effector Function of TH2 Cells and the Development of Allergic Airways Disease", Proceedings of the National Academy of Sciences of the United States of America, 106(44):18704-18709.
Mayer et al. (Apr. 27, 2001) "Identification of Receptor Binding and Activation Determinants in the N-Terminal and N-loop Regions of the CC Chemokine Eotaxin", Journal of Biological Chemistry, 276(17):13911-13916.
Mayo Clinic, (Oct. 10, 2017) "Eosinophilic Esophagitis", Available at: http://www.mayoclinic.org/diseases-conditions/eosinophilic-esophagitis/basics/treatment/con-20035681.
Mayoral et al. (Jan. 1, 2009) "MicroRNA-221-222 Regulate the Cell-Cycle in Mast Cells", Journal of Immunology, 182(1):433-445.
McGettrick et al. (Sep. 25, 2007) "Toll-like Receptors: Key Activators of Leucocytes and Regulator of Haematopoiesis", British Journal of Haematology, 139(2): 185-193.
Medina et al. (Sep. 2, 2010) "OncomiR Addiction in an in Vivo Model of microRNA-21-induced Pre-B-cell Lymphoma", Nature, 467(7311):86-90.
Meineke et al. (Dec. 2002) "Pharmacokinetic modelling of morphine, morphine-3- glucuronide and morphine-6-glucuronide in plasma and cerebrospinal fluid of neurosurgical patients after short-term infusion of morphine", British Journal of Clinical Pharmacology, 54(6):592-603.
Menard-Katcher et al. (2012) "MicroRNAs are Altered in Eosinophilic Esophagitis", Gastroenterology, 142(5) 8440.
Menzies-Gow et al. (Apr. 2003) "Anti-IL-5 (Mepolizumab) Therapy Induces Bone Marrow Eosinophil Maturational Arrest and Decreases Eosinophil Progenitors in the Bronchial Mucosa of Atopic Asthmatics", The Journal of Allergy and Clinical Immunology, 111(4):714-719.
Meyer et al. (Jan. 2013) "The UCSC Genome Browser database: Extensions and Updates 2013", Nucleic Acids Research, 41:D64-D69.

(56) References Cited

OTHER PUBLICATIONS

Michael et al. (2005) "Biochemical and Enzymatic Characterization of Human Kallikrein 5 (hK5), a Novel Serine Protease Potentially Involved in Cancer Progression", Journal of Biological Chemistry, 280(15):14628-35.
Michaels et al. (Feb. 5-11, 2005) "Prediction of Cancer Outcome with Microarrays: A Multiple Random Validation Strategy", Lancet, 365(9458):488-492.
Milbrandt J. (Nov. 6, 1987) "A Nerve Growth Factor-induced Gene Encodes a Possible Transcriptional Regulatory Factor", Science, 238(4828):797-799.
Milgrom et al. (Dec. 23, 1999) "Treatment of Allergic Asthma with Monoclonal Anti-IgE Antibody", The New England Journal of Medicine, 341(26):1966-1973.
Mishra et al. (Jan. 1, 2001) "An Etiological Role for Aeroallergens and Eosinophils in Experimental Esophagitis", Journal of Clinical Investigation, 107(1):83-90.
Mishra et al. (Jan. 2008) "Esophageal Remodeling Develops as a Consequence of Tissue Specific IL-5-induced Eosinophilia", Gastroenterology, 134(1):204-214.
Mishra et al. (Mar. 1, 2002) "IL-5 Promotes Eosinophil Trafficking to the Esophagus", The Journal of Immunology, 168(5):2464-2469.
Mishra et al. (Nov. 2003) "Intratracheal IL-13 Induces Eosinophilic Esophagitis by an IL-5, Eotaxin-1, and STAT6-Dependent Mechanism", Gastroenterology, 125(5)1419-1427.
Mitchell et al. (Jul. 29, 2008) "Circulating microRNAs as Stable Blood-based Markers for Cancer Detection", Proceedings of the National Academy of Sciences of the United States of America, 105(30):10513-10518.
Mizuno et al. (2013) "Genotype of Abcc3-211c > T Influences the Pharmacokinetics of Morphine Glucuronide in Children", Clinical Pharmacology & Therapeutics, 93:S63.
Mogil et al. (Jul. 6, 1999) "The genetic mediation of individual differences in sensitivity to pain and its inhibition", PNAS, 96(14):7744-7751.
Molina-Infante et al. (May 7, 2008) "Overlap of Reflux and Eosinophilic Esophagitis in Two Patients Requiring Different Therapies: A Review of the Literature", World Journal of Gastroenterology, 14(9):1463-1466.
Mori et al. (Jan. 16, 2009) "Identification of the Human Eosinophil Lineage-committed Progenitor: Revision of Phenotypic Definition of the Human Common Myeloid Progenitor", Journal of Experimental Medicine, 206(1):183-193.
Mukhopadhyay et al. (Jul. 2010) "Matrix Metalloproteinase-12 is a Therapeutic Target for Asthma in Children and Young Adults", The Journal of Allergy and Clinical Immunology, 126(1):70-76.
Mulder et al. (Jan. 12, 2011) "Understanding Eosinophilic Esophagitis: The Cellular and Molecular Mechanisms of an Emerging Disease", Mucosal Immunology, 4(2):139-147.
Murata et al. (Jul. 2008) "Activation of Toll-like Receptor 2 by a Novel Preparation of Cell Wall Skeleton from Mycobacterium Bovis BCG Tokyo (SMP-105) Sufficiently Enhances Immune Responses Against Tumors", Cancer Science, 99(7):1435-1440.
Nagai et al. (Jun. 2006) "Toll-like Receptors on Hematopoietic Progenitor Cells Stimulate Innate Immune System Replenishment", Immunity, 24(6):801-812.
Nagase et al. (Oct. 15, 2003) "Expression and Function of Toll-like Receptors in Eosinophils: Activation by Toll-like Receptor 7 Ligand", Journal of Immunology, 171(8):3977-3982.
Navarro et al. (Jun. 1, 2010) "Small RNAs Guide Hematopoietic Cell Differentiation and Function", Journal of Immunology, 184(11):5939-5947.
Naya et al. (May 7, 2001) "Discovery of a Novel CCR3 Selective Antagonist", Bioorganic & Medicinal Chemistry Letters, 11(9):1219-1223.
Naya et al. (Jun. 2003) "Structure-Activity Relationships of 2-(Benzothiazolylthio)acetamide Class of CCR3 Selective Antagonist", Chemical and Pharmaceutical Bulletin, 51(6):697-701.

Newberry et al. (Nov. 2005) "Strongyloides Hyperinfection Presenting as Acute Respiratory Failure and Gram-negative Sepsis", Chest, 128(5):3681-3684.
Noel et al. (Jul. 2004) "Clinical and Immunopathologic Effects of Swallowed Fluticasone for Eosinophilic Esophagitis", Clinical Gastroenterology and Hepatology, 2(7):568-575.
Notterman et al. (2002) "Tumor Biology and Microarray Analysis of Solid Tumors: Colorectal Cancer as a Model System", Microarrays and Cancer Research, 81-111.
Novak et al. (Apr. 1, 2007) "CCL23 Expression Is Induced by IL-4 in a STAT6-Dependent Fashion", Journal of Immunology, 178(7):4335-4341.
Ogbogu et al. (Dec. 2009) "Hypereosinophilic Syndromes: A Multicenter, Retrospective Analysis of Clinical Characteristics and Response to Therapy", The Journal of Allergy and Clinical Immunology, 124(6):1319-1325.
Ordoñez et al. (Dec. 2000) "Epithelial Desquamation in Asthma", American Journal of Respiratory and Critical Care Medicine, 162(6):2324-2329.
Ozawa et al. (Oct. 2009) "BRAK/CXCL14 Expression Oral Carcinoma Cells Completely Suppresses Tumor Cell Xenografts in SCID Mouse", Biomedical Research, 30(5):315-318.
Ozawa et al. (Oct. 11, 2009) "Restoration of BRAK/CXCL14 Gene Expression by Gefitinib is Associated with Antitumor Efficacy of the Drug in Head and Neck Squamous Cell Carcinoma", Cancer Science, 100(11):2202-2209.
Zahm et al. (Jul. 2011) "Circulating MicroRNA Is a Biomarker of Pediatric Crohn Disease", Journal of Pediatric Gastroenterology and Nutrition, 53(1):26-33.
Zediak et al. (Mar. 1, 2011) "Cutting Edge: Persistently Open Chromatin at Effector Gene Loci in Resting Memory CD8+ T Cells Independent of Transcriptional Status", Journal of Immunology, 186(5):2705-2709.
Zeng et al. (Feb. 2006) "Extracting Principal Diagnosis, Co-morbidity and Smoking Status for Asthma Research: Evaluation of a Natural Language Processing System", BMC Medical Informatics and Decision Making, 6(1):9 pages.
Zhang et al. (Dec. 2009) "Effects of Endogenous Glucocorticoids on Allergic Inflammation and T(H)1/T(H)2 Balance in Airway Allergic Disease", Annals of Allergy, Asthma & Immunology, 103(6):525-534.
Zhen et al. (Feb. 2007) "IL-13 and Epidermal Growth Factor Receptor Have Critical but Distinct Roles in Epithelial Cell Mucin Production", American Journal of Respiratory Cell and Molecular Biology, 36(2):244-253.
Zheng et al. (Mar. 2009) "Transgenic Expression of Interleukin-13 in the Skin Induces a Pruritic Dermatitis and Skin Remodeling", Journal of Investigative Dermatology, 129(3):742-751.
Caramori et al. (Aug. 2005) "Anti-inflammatory Mechanisms of Glucocorticoids Targeting Granulocytes", Current Drug Targets—Inflammation & Allergy, 4(4):455-463.
Carriere et al. (Jan. 2, 2007) "IL-33, the IL-1-like Cytokine Ligand for ST2 Receptor, is a Chromatin-associated Nuclear Factor in Vivo", Proceedings of the National Academy of Sciences of the United States of America, 104 (1):282-287.
Carthew et al. (Feb. 20, 2009) "Origins and Mechanisms of miRNAs and siRNAs", Cell, 136(4):642-655.
Chehade et al. (Jun. 2010) "Food Allergy and Eosinophilic Esophagitis", Current Opinion in Allergy and Clinical Immunology, 10(3):231-237.
Chen et al. (Jul. 1, 2009) "ToppGene Suite for Gene List Enrichment Analysis and Candidate Gene Prioritization", Nucleic Acids Research, 37(Suppl. 2):W305-W311.
Cheverud Jamesm. (Jul. 2001) "A Simple Correction for Multiple Comparisons in Interval Mapping Genome Scans", Heredity, 87(Pt 1):52-58.
Cho et al. (Mar. 24, 2006) "Role of Early Growth Response-1 (Egr-1) in Interleukin-13-induced Inflammation and Remodeling", Journal of Biological Chemistry, 281(12):8161-8168.
Chu et al. (Jan. 9, 2011) "Eosinophils are Required for the Maintenance of Plasma Cells in the Bone Marrow", Nature Immunology, 12(2):151-159.

(56) References Cited

OTHER PUBLICATIONS

Clavijo et al. (Mar. 12, 2011) "A sensitive assay for the quantification of morphine and its active metabolites in human plasma and dried blood spots using high-performance liquid chromatography-tandem mass spectrometry", Analytical and Bioanalytical Chemistry, 400(3):715-728.
Cohen et al. (Aug. 2012) "Pharmacogenetics in perioperative medicine", Current opinion in anaesthesiology, 25 (4):419-427.
Collins et al. (Jun. 2008) "Clinical, Pathologic, and Molecular Characterization of Familial Eosinophilic Esophagitis Compared With Sporadic Cases", Clinical Gastroenterology and Hepatology, 6(6):621-629.
Collins et al. (Oct. 2005) "Online Selection of Discriminative Tracking Features", IEEE Transactions on Pattern Analysis and Machine Intelligence, 27(10):1631-1643.
Collison et al. (Jul. 2011) "Inhibition of House Dust Mite-induced Allergic Airways Disease by Antagonism of MicroRNA-145 is Comparable to Glucocorticoid Treatment", The Journal of Allergy and Clinical Immunology, e4, 128(1):160-167.
Corren et al. (Sep. 22, 2011) "Lebrikizumab Treatment in Adults with Asthma", The New England Journal of Medicine, 365(12):1088-1098.
Crews et al. (Jan. 29, 2014) "Clinical Pharmacogenetics Implementation Consortium Guidelines For Cytochrome P450 2d6 Genotype And Codeine Therapy", Clinical Pharmacology & Therapeutics, 95(4):376-382.
Czajkowsky et al. (Oct. 2012) "Fc-fusion Proteins: New Developments and Future Prospectives", EMBO Molecular Medicine, 4(10):1015-1028.
D'Agostini et al. (Jul. 2005) "Antitumour Effect of Om-174 and Cyclophosphamide on Murine B16 Melanoma in Different Experimental Conditions", International Immunopharmacology, 5(7-8):1205-1212.
Dalal et al. (Oct. 31, 1997) "Molecular Characterization of Neurotrophin Expression and the Corresponding Tropomyosin Receptor Kinases (trks) in Epithelial and Stromal Cells of the Human Prostate", Molecular and Cellular Endocrinology, 134(1):15-22.
Davis Carla M. (Feb. 11, 2011) "Diagnosis and Treatment of Eosinophilic Gastrointestinal Disorders", Pediatric Allergy, Immunology, and Pulmonology, 23(4):237-242.
De Bruin et al. (Oct. 7, 2010) "Eosinophil Differentiation in the Bone Marrow is Inhibited by T Cell-derived IFN-γ", Blood, 116(14):2559-2569.
Debrosse et al. (Jul. 2010) "Identification, Epidemiology and Chronicity of Pediatric Esophageal Eosinophilia from 1982-1999", The Journal of Allergy and Clinical Immunology, 126(1):112-119.
Dellon et al. (May 1, 2014) "59 Immunohistochemical Evidence of Inflammation Is Similar in Patients With Eosinophilic Esophagitis and PPI-Responsive Esophageal Eosinophilia: A Prospective Cohort Study", Gastroenterology, 146(5):S17.
Dellon et al. (Oct. 22, 2013) "Clinical and endoscopic characteristics do not reliably differentiate PPI-responsive esophageal eosinophilia and eosinophilic esophagitis in patients undergoing upper endoscopy: a prospective cohort study", The American Journal of Gastroenterology, 108(12):1854-1860.
Dellon et al. (Jul. 2012) "Eosinophilic Esophagitis: Diagnostic Tests and Criteria", Current Opinion in Gastroenterology, 28(4):382-388.
Dellon et al. (Feb. 2011) "Tryptase Staining of Mast Cells may Differentiate Eosinophilic Esophagitis from Gastroesophageal Reflux Disease", The American Journal of Gastroenterology, 106(2):264-271.
Dent et al. (Nov. 1, 1990) "Eosinophilia in Transgenic Mice Expressing Interleukin 5", Journal of Experimental Medicine, 172(5):1425-1431.
Descamps et al. (Jul. 2005) "Expression of Nerve Growth Factor Receptors and their Prognostic Value in Human Breast Cancer", Oncology Reports, 14(1):161-171.
Dewson et al. (Oct. 1, 2001) "Interleukin-5 Inhibits Translocation of Bax to the Mitochondria, Cytochrome C Release, and Activation of Caspases in Human Eosinophil", Blood, 98(7):2239-2247.

Dohrman et al. (Aug. 1997) "Ethanol Reduces Expression of the Nerve Growth Factor Receptor, But not Nerve Growth Factor Protein Levels in the Neonatal Rat Cerebellum", Alcoholism: Clinical and Experimental Research, 21(5):882-893.
Donato et al. (Jan. 1, 2002) "Human HTm4 is a Hematopoietic Cell Cycle Regulator", Journal of Clinical Investigation, 109(1):51-58.
Driss et al. (Apr. 2, 2009) "TLR2-dependent Eosinophil Interactions with Mycobacteria: Role of Alpha-defensins", Blood, 113(14):3235-3244.
Dyer et al. (Sep. 15, 2008) "Functionally Competent Eosinophils Differentiated Ex Vivo in High Purity From Normal Mouse Bone Marrow", Journal of Immunology, 181(6):4004-4009.
Dyer et al. (Jan. 1, 2009) "Generation of Eosinophils from Unselected Bone Marrow Progenitors: Wild-type, TLR- and Eosinophil-deficient Mice", The Open Immunology Journal, 2:163-167.
Dyer et al. (Jun. 1, 2010) "Mouse and Human Eosinophils De Granulate in Response to Platelet-activating Factor (PAF) and C21 LysoPAF Via A Paf receptor-independent Mechanism: Evidence for a Novel Receptor", Journal of Immunology, 184(11):6327-6334.
Dyer et al. (Sep. 24, 2009) "Pneumoviruses Infect Eosinophils and Elicit MyD88-dependent Release of Chemoattractant Cytokines and Interleukin-6", Blood, 114(13):2649-2656.
Ehlers et al. (1991) "Differentiation of T Cell Lymphokine Gene Expression: The in Vitro Acquisition of T Cell Memory", Journal of Experimental Medicine, 173(1):25-36.
Eissing et al. (Feb. 1, 2012) "Pharmacogenomics of Codeine, Morphine, and Morphine-6-Glucuronide: Model-Based Analysis of the Influence of CYP2D6 Activity, UGT2B7 Activity, Renal Impairment, and CYP3A4 Inhibition", Molecular Diagnosis & Therapy, 16(1):43-53.
Elsner (Nov. 1992) "The CC Chemokine Antagonist Met-RANTES Inhibits Eosinophil Effector Functions through the Chemokine Receptors CCR1 and CCR3", European Journal of Immunology, 27(11):2892-2998.
Fahy et al. (Nov. 15, 2001) "Remodeling of the Airway Epithelium in Asthma", American Journal of Respiratory and Critical Care Medicine, 164(10 Pt 2):S46-S51.
Fardet et al. (Jan. 22, 2006) "Severe Strongyloidiasis in Corticosteroid-treated Patients: Case Series and Literature Review", Journal of Infection, 54(1):18-27.
Faubion et al. (Jul. 1998) "Treatment of Eosinophilic Esophagitis with Inhaled Corticosteroids", Journal of Pediatric Gastroenterology and Nutrition, 27(1):90-93.
Festuccia et al. (Jan. 2007) "Tyrosine Kinase Inhibitor CEP-701 Blocks the NTRK1/NGF Receptor and Limits the Invasive Capability of Prostate Cancer Cells in Vitro", International Journal of Oncology, 30(1):193-200.
Flower et al. (Nov. 16, 1999) "Modelling G-protein-coupled Receptors for Drug Design", Biochimica et Biophysica Acta, 1422(3):207-234.
Fox et al. (Aug. 2002) "Eosinophilic Esophagitis: It's Not Just Kid's Stuff", Gastrointestinal Endoscopy, 56(2):260-270.
Freund-Michel et al. (Jan. 2008) "The Nerve Growth Factor and its Receptors in Airway Inflammatory Diseases", Pharmacology & Therapeutics, 117(1):52-76.
Frossard et al. (Oct. 1, 2004) "Nerve Growth Factor and its Receptors in Asthma and Inflammation", European Journal of Pharmacology, 500(1-3):453-465.
Fuentebella et al. (Sep. 2010) "Increased Number of Regulatory T Cells in Esophageal Tissue of Patients with Eosinophilic Esophagitis in Comparison to Gastro Esophageal Reflux Disease and Control Groups", Journal of Pediatric Gastroenterology and Nutrition, 51(3):283-589.
Fukada et al. (Jul. 2013) "OCT1 genetic variants influence the pharmacokinetics of morphine in children", Pharmacogenomics, 14(10):1141-1151.
Fukao (Jun. 2007) "An Evolutionarily Conserved Mechanism for MicroRNA-223 Expression Revealed by MicroRNA Gene Profiling", Cell, 129(3):617-631.
Fukuda et al. (Feb. 2013) "Oral Session II-A (OII-A) Special Populations 3:45 pm-4:45 pm", Clinical Pharmacology & Therapeutics, 93:S49-S51.

(56) References Cited

OTHER PUBLICATIONS

Fulkerson et al. (Oct. 31, 2006) "A Central Regulatory Role for Eosinophils and the Eotaxin/CCR3 Axis in Chronic Experimental Allergic Airway Inflammation", Proceedings of the National Academy of Sciences of the United States of America, 103(44):16418-16423.
Fulkerson et al. (Feb. 2013) "Targeting Eosinophils in Allergy, Inflammation and Beyond", Nature Reviews Drug Discovery, 12(2):117-129.
Furuta et al. (Oct. 2007) "Eosinophilic Esophagitis in Children and Adults: A Systematic Review and Consensus Recommendations for Diagnosis and Treatment", Gastroenterology, 133(4):1342-1363.
Garbacki et al. (Jan. 28, 2011) "MicroRNAs Profiling in Murine Models of Acute and Chronic Asthma: A Relationship with mRNAs Targets", PLoS One, e16509, 6(1):23 pages.
Garcia-Echeverria et al. (Apr. 2004) "In Vivo Antitumor Activity of NVP-AEW541-A Novel, Potent, and Selective Inhibitor of the IGF-IR Kinase", Cancer Cell, 5(3):231-239.
Garon et al. (Aug. 1, 2011) "Development of an AS04-adjuvanted HPV Vaccine with the Adjuvant System Approach", BioDrugs, 25(4):217-226.
Garrett et al. (Jan. 2004) "Anti-interleukin-5 (Mepolizumab) Therapy for Hypereosinophilic Syndrome", Journal of Allergy and Clinical Immunology, 113(1):115-119.
Georgantas et al. (Feb. 20, 2007) "CD34+ Hematopoietic Stem-progenitor Cell MicroRNA Expression and Function: A Circuit Diagram of Differentiation Control", Proceedings of the National Academy of Sciences of the United States of America, 104(8):2750-2755.
Gilbert et al. (Aug. 1978) "Effects of Acute Endotoxemia and Glucose Administration on Circulating Leukocyte Populations in Normal and Diabetic Subjects", Metabolism, 27(8):889-899.
Goettig et al. (2010) "Natural and Synthetic Inhibitors of Kallikrein-Related Peptidases (KLKs)", Biochimie, 92 (11):1546-67.
Gong et al. (May 30, 2013) "Gene polymorphisms of OPRM1 A118G and ABCB1 C3435T may influence opioid requirements in Chinese patients with cancer pain", Asian Pacific Journal of Cancer Prevention, 14(5):2937-2943.
Gonsalves et al. (Jan. 2020) "Diagnosis and Treatment of Eosinophilic Esophagitis", The Journal of Allergy and Clinical Immunology, 145(1):1-7.
Gonsalves et al. (Sep. 2006) "Histopathologic Variability and Endoscopic Correlates in Adults with Eosinophilic Esophagitis", Gastrointestinal Endoscopy, 64(3):313-319.
Griffiths-Jones et al. (2006) "miRBase: MicroRNA Sequences, Targets and Gene Nomenclature", Nucleic Acids Research, 34:D140-D144.
Griffiths-Jones et al. (Jan. 2008) "miRBase: Tools for Micro RNA Genomics", Nucleic Acids Research, 36 (Database issue):D154-D158.
Gupta et al. (Jan. 2006) "Cytokine Expression in Normal and Inflamed Esophageal Mucosa: A Study into the Pathogenesis of Allergic Eosinophilic Esophagitis", Journal of Pediatric Gastroenterology and Nutrition: , 42(1):22-26.
Gupta et al. (May 1998) "Expression of Inducible Nitric Oxide Synthase (iNOS) mRNA in Inflamed Esophageal and Colonic Mucosa in a Pediatric Population", American Journal of Gastroenterology, 93(5):795-798.
Guyon et al. (Jan. 2002) "Gene Selection for Cancer Classification using Support Vector Machines", Machine Learning, 46:389-422.
Hahn et al. (Apr. 2006) "Airway Epithelial Cells Produce Neurotrophins and Promote the Survival of Eosinophils During Allergic Airway Inflammation", Journal of Allergy and Clinical Immunology, 117(4):787-794.
Hamilton et al. (1980) "Regulation of The Plasminogen Activator Activity of Macrophage Tumor Cell Lines", International Journal of Immunopharmacology, 2(4):353-362.
Hamoui et al. (Aug. 2004) "Increased Acid Exposure in Patients With Gastroesophageal Reflux Disease Influences Cyclooxygenase-2 Gene Expression in the Squamous Epithelium of the Lower Esophagus", Archives of Surgery, 139(7):712-716.
Hardiman Gary (Nov. 5, 2004) "Microarray Platforms—Comparisons and Contrasts", Pharmacogenomics, 5(5):487-502.
Hatley et al. (Sep. 14, 2010) "Modulation of K-Ras-dependent Lung Tumorigenesis by MicroRNA-21", Cancer Cell, 18(3):282-293.
Heib et al. (May 2019) "Wheat Amylase/Trypsin Inhibitors Aggravate Eosinophilic Esophagitis", Gastroenterology, 6 (Suppl. 1):1 page.
Hennessy et al. (Apr. 2010) "Targeting Toll-Like Receptors: Emerging Therapeutics?", Nature Reviews Drug Discovery, 9(4):293-307.
Himes et al. (Mar. 4, 2009) "Prediction of Chronic Obstructive Pulmonary Disease (COPD) in Asthma Patients Using Electronic Medical Records", Journal of the American Medical Informatics Association, 16(3):371-379.
Hogan et al. (May 2008) "Eosinophils: Biological Properties and Role in Health and Disease", Clinical & Experimental Allergy, 38(5):709-750.
Hogan et al. (Dec. 2004) "The Eosinophil as a Therapeutic Target in Gastrointestinal Disease", Alimentary Pharmacology and Therapeutics, 20(11-12):1231-1240.
Hotchkiss et al. (Jun. 1, 2001) "Sepsis-induced Apoptosis Causes Progressive Profound Depletion of B and CD4+ T Lymphocytes in Humans", Journal of Immunology, 166(11):6952-6963.
Huang et al. (Jul. 1, 2006) "RegRNA: An Integrated Web Server for Identifying Regulatory RNA Motifs and Elements", Nucleic Acids Research, 34:W429-W434.
Hwang et al. (Apr. 30, 2005) "Expression of IL-17 Homologs and their Receptors in the Synovial Cells of Rheumatoid Arthritis Patients", Molecular Cell, 19(2):180-184.
Indo Y. (Dec. 2001) "Molecular Basis of Congenital Insensitivity to Pain with Anhidrosis (CIPA): Mutations and Polymorphisms in TRKA (NTRK1) Gene Encoding the Receptor Tyrosine Kinase for Nerve Qrowth Factor", Human Mutation, 18(6):462-471.
Indo et al. (Aug. 1996) "Mutations in the TRKA/NGF Receptor Gene in Patients with Congenital Insensitivity to Pain with Anhidrosis", Nature Genetics, 13(4):485-488.
Indo Y. (Oct. 2012) "Nerve Growth Factor and the Physiology of Pain: Lessons from Congenital Insensitivity to Pain with Anhidrosis", Clinical Genetics, 82(4):341-350.
Ip et al. (Dec. 2007) "Interleukin-31 Induces Cytokine and Chemokine Production from Human Bronchial Epithelial Cells through Activation of Mitogen-activated Protein Kinase Signalling Pathways: Implications for the Allergic Response", Immunology, 122(4):532-541.
Iwasaki et al. (Jun. 20, 2005) "Identification of Eosinophil Lineage-committed Progenitors in the Murine Bone Marrow", Journal of Experimental Medicine, 201(12):1891-1897.
Jacobsen et al. (Jun. 2007) "Eosinophils: Singularly Destructive Effector Cells or Purveyors of Immunoregulation?", The Journal of Allergy and Clinical Immunology, 119(6): 1313-1320.
Jakiela et al. (Oct. 2009) "Intrinsic Pathway of Apoptosis in Peripheral Blood Eosinophils of Churg-strauss Syndrome", Rheumatology (Oxford), 48(10):1202-1207.
Jia et al. (Nov. 2008) "Mist1 Regulates Pancreatic Acinar Cell Proliferation through p21 CIP1/WAF1", Gastroenterology, 135(5):1687-1697.
Jiang et al. (Jul. 2011) "The Emerging Role of MicroRNAs in Asthma", Molecular and Cellular Biochemistry, 353(1-2):35-40.
Johnnidis et al. (Feb. 28, 2008) "Regulation of Progenitor Cell Proliferation and Granulocyte Function by MicroRNA-223", Nature, 451:1125-1129.
Juffali et al. (2010) "The WiNAM project: Neural data analysis with applications to epilespy", Biomedical Circuits and Systems Conference, 45-48.
Junttila et al. (Oct. 27, 2008) "Tuning Sensitivity to IL-4 and IL-13: Differential Expression of IL-4Ralpha, IL-13Ralpha1, and Gammac Regulates Relative Cytokine Sensitivity", Journal of Experimental Medicine, 205 (11):2595-2608.
Kaiko et al. (Feb. 2011) "New Insights into the Generation of Th2 Immunity and Potential Therapeutic Targets for the Treatment of Asthma", Current Opinion in Allergy and Clinical Immunology, 11(1):39-45.

(56) References Cited

OTHER PUBLICATIONS

Kaimal et al. (Jul. 2010) "Toppcluster: A Multiple Gene List Feature Analyzer for Comparative Enrichment Clustering and Network-based Dissection of Biological System", Nucleic Acids Research, 38:W96-W102.
Kanzler et al. (May 3, 2007) "Therapeutic Targeting of Innate Immunity with Toll-like Receptor Agonists and Antagonists", Nature Medicine, 13(5):552-559.
Kariyawasam et al. (Sep. 2009) "Activin and Transforming Growth Factor-β Signaling Pathways are Activated after Allergen Challenge in Mild Asthma", The Journal of Allergy and Clinical Immunology, 124(3):454-462.
Ozdas et al. (Sep. 2004) "Investigation of Vocal Jitter and Glottal Flow Spectrum as Possible Cues for Depression and Near-Term Suicidal Risk", Transactions on Biomedical Engineering, 51(9):1530-1540.
Papagiannakopoulos et al. (Oct. 1, 2008) "MicroRNA-21 Targets a Network of Key Tumor-Suppressive Pathways in Glioblastoma Cells", Cancer Research, 68(19):8164-8172.
Park et al. (Dec. 27, 2006) "Genetic polymorphisms in the ABCB1 gene and the effects of fentanyl in Koreans", Clinical Pharmacology & Therapeutics, 81(4):539-546.
Patent Cooperation Treaty, "International Preliminary Report on Patentability and Written Opinion in corresponding International application No. PCT/US2012/044061", dated Dec. 23, 2013, 7 pages.
PCTUS2015044461, "International Search Report dated Nov. 9, 2015 for International Application No. PCT/US2015/044461", 11 pages.
Peeters et al. (Apr. 8, 2005) "Real-time RT-PCR Quantification of mRNA Encoding Cytokines and Chemokines in Histologically Normal Canine Nasal, Bronchial and Pulmonary Tissue", Veterinary Immunology and Immunopathology, 104(3-4):195-204.
Persson et al. (Jun. 2001) "Bactericidal Activity of Human Eosinophilic Granulocytes Against *Escherichia coli*", Infection and Immunity, 69(6):3591-3596.
Petriv et al. (Aug. 31, 2010) "Comprehensive MicroRNA Expression Profiling of the Hematopoietic Hierarchy", Proceedings of the National Academy of Sciences of the United States of America, 107(35):15443-15448.
Phipps et al. (Sep. 1, 2007) "Eosinophils Contribute to Innate Antiviral Immunity and Promote Clearance of Respiratory Syncytial Virus", Blood, 110(5):1578-1586.
Plötz et al. (Jan. 1, 2001) "The Interaction of Human Peripheral Blood Eosinophils with Bacterial Lipopolysaccharide is CD14 Dependent", Blood, 97(1):235-241.
Polikepahad et al. (Sep. 24, 2010) "Proinflammatory Role for let-7 MicroRNAs in Experimental Asthma", Journal of Biological Chemistry, 285(39):30139-30149.
Pouladi et al. (Jan. 2004) "Interleukin-13-dependent Expression of Matrix Metalloproteinase-12 is Required for the Development of Airway Eosinophilia in Mice", American Journal of Respiratory Cell and Molecular Biology, 30(1):84-90.
Proudfoot et al. (Nov. 5, 1999) "Amino-terminally Modified RANTES Analogues Demonstrate Differential Effects on RANTES Receptors", Journal of Biological Chemistry, 274(45):32478-32485.
Prows et al. (Nov. 13, 2013) "Codeine-related adverse drug reactions in children following tonsillectomy: a prospective study", Laryngoscope, 124(5):1242-1250.
Prussin et al. (Dec. 2009) "Eosinophilic Gastrointestinal Disease and Peanut Allergy are Alternatively Associated with IL-5+ and IL-5(-) T(H)2 Responses", The Journal of Allergy and Clinical Immunology, 124 (6):1326-1332.
Raap et al. (Feb. 2010) "The Role of Neurotrophins in the Pathophysiology of Allergic Rhinitis", Current Opinion in Allergy and Clinical Immunology, 10(1):8-13.
Rabinowits et al. (Jan. 2009) "Exosomal microRNA: a Diagnostic Marker for Lung Cancer", Clinical Lung Cancer, 10(1):42-46.
Rahaghi et al. ( 2017) "Long-term Clinical Outcomes Following Treatment with Alpha 1-Proteinase Inhibitor for COPD associated with alpha-1 Antitrypsin Deficiency: A Look at the Evidence", Respiratory Researc, 18(1):9 Pages.
Zuo et al. (Jul. 1, 2010) "IL-13 Induces Esophageal Remodeling and Gene Expression by an Eosinophil-Independent, IL-13Ra2-Inhibited Pathway", The Journal of Immunology, 185(1):660-669.
Ramirez et al. (Dec. 15, 2004) "Immortalization of Human Bronchial Epithelial Cells in the Absence of Viral Oncoproteins", Cancer Research, 64(24):9027-9034.
Ramirez et al. (Aug. 2006) "Transcriptional Regulation of the Human α2(I) Collagen Gene (COL1A2), an Informative Model System to Study Fibrotic Diseases", Matrix Biology, 25(6):365-372.
Rank et al. (May 2020) "Technical Review on the Management of Eosinophilic Esophagitis: A Report from the AGA Institute and the Joint Task Force on Allergy-immunology Practice Parameters", Annals of Allergy, Asthma & Immunology, e17, 124(5):424-440.
Ray et al. (May 16, 2011) "Human Mu Opioid Receptor (OPRM1 A 118G) polymorphism is associated with brain mu-opioid receptor binding potential in smokers", PNAS, 108(22):9268-9273.
Raychaudhuri et al. (2000) "Principal Components Analysis to Summarize Microarray Experiments: Application to Sporulation Time Series", Pacific Symposium on Biocomputing, 5:452-463.
Robinson et al. (Jan. 1999) "CD34(+)/Interleukin-5Ralpha Messenger RNA+ Cells in the Bronchial Mucosa in Asthma: Potential Airway Eosinophil Progenitors", American Journal of Respiratory Cell and Molecular Biology, 20(1):9-13.
Rochman et al. (Jun. 1, 2007) "Cutting Edge: Direct Action of Thymic Stromal Lymphopoietin on Activated Human CD4+ T cells", The Journal of Immunology, 178(11):6720-6724.
Rochman et al. (Jul. 2015) "Neurotrophic Tyrosine Kinase Receptor 1 is a Direct Transcriptional and Epigenetic Target of IL-13 Involved in Allergic Inflammation", Immunology, 8(4):785-798.
Rodrigo et al. (Feb. 2008) "High Intraepithelial Eosinophil Counts in Esophageal Squamous Epithelium Are Not Specific for Eosinophilic Esophagitis in Adults", The American Journal of Gastroenterology, 103(2);435-442.
Romani et al. (Jul. 9, 2002) "Cluster Analysis of Gene Expression Dynamics", Proceedings of the National Academy of Sciences, 99(14):9121-9126.
Rosas et al. (Jul. 2006) "IL-5-mediated Eosinophil Survival Requires Inhibition of GSK-3 and Correlates with β-catenin Relocalization", Journal of Leukocyte Biology, 80(1):186-195.
Rothenberg Marc E. (Oct. 2009) "Biology and Treatment of Eosinophilic Esophagitis", Gastroenterology, 137(4):1238-1249.
Rothenberg et al. (Apr. 2010) "Common Variants at 5q22 Associate with Pediatric Eosinophilic Esophagitis", Nature Genetics, 42(4):289-291.
Rothenberg et al. (Jan. 2004) "Eosinophilic Gastrointestinal Disorders (EGID)", The Journal of Allergy and Clinical ImmunologyThe Journal of Allergy and Clinical Immunology, 113(1):11-28.
Rothenberg et al. (Dec. 2001) "Pathogenesis and Clinical Features of Eosinophilic Esophagitis", The Journal of Allergy and Clinical Immunology, 108(6):891-894.
Rothenberg et al. (Apr. 2010) "The Eosinophil", Annual Review of Immunology, 24:147-174.
Rothenberg et al. (Mar. 20, 2008) "Treatment of Patients with the Hypereosinophilic Syndrome with Mepolizumab", The New England Journal of Medicine, 358(12):1215-1228.
Russ et al. (2013) "T Cell Immunity as a Tool for Studying Epigenetic Regulation of Cellular Differentiation", Frontiers in Genetics, 4:218.
Sabroe et al. (Aug. 25, 2000) "A Small Molecule Antagonist of Chemokine Receptors CCR1 and CCR3", The Journal of Biological Chemistry, 275(34):25985-25992.
Sabroe et al. (May 1, 2002) "Toll-Like Receptor (TLR)2 and TLR4 in Human Peripheral Blood Granulocytes: A Critical Role for Monocytes in Leukocyte Lipopolysaccharide Responses", The Journal of Immunology, 168(9):4701-4710.
Sadhasivam et al. (2014) "Genetics of pain perception, COMT and postoperative pain management in children", The Pharmacogenomics Journal, 15(3):277-284.
Sadhasivam et al. (Jul.-Aug. 2012) "Morphine clearance in children: does race or genetics matter?", Journal of Opioid Management, 8(4):217-226.

(56) References Cited

OTHER PUBLICATIONS

Sadhasivam et al. (2015) "Novel Associations between FAAH Genetic Varients an Postoperative Central Opioid Related Adverse Effects", The Pharmacogenomics Journal, 15(5):436-442.

Sadhasivam et al. (Jun. 13, 2012) "Preventing Opioid-Related Deaths in Children Undergoing Surgery", Pain Medicine, 13(7):982-983.

Sadhasivam et al. (Apr. 23, 2012) "Race and unequal burden of perioperative pain and opioid related adverse effects in children", Pediatrics, 129(5):832-838.

Saeki et al. (Mar. 2, 2001) "Identification of a Potent and Nonpeptidyl CCR3 Antagonist", Biochemical and Biophysical Research Communications, 281(3):779-782.

Sahin et al. (Oct. 2014) "mRNA-Based Therapeutics—Developing a New Class of Drugs", Nature reviews, 13(10):759-780.

Saini et al. (Nov. 27, 2008) "Annotation of Mammalian Primary microRNAs", BMC Genomics, Article No. 564, 9(1):19 pages.

Saito et al. (Mar. 15, 2002) "Pathogenesis of Murine Experimental Allergic Rhinitis: A Study of Local and Systemic Consequences of IL-5 Deficiency", The Journal of Immunology, 168(6):3017-3023.

Assa'Ad et al. (Nov. 2011) "An Antibody Against IL-5 Reduces Numbers of Esophageal Intraepithelial Eosinophils in Children With Eosinophilic Esophagitis", Gastroenterology, 141(5):1593-1604.

Assa'Ad et al. (Mar. 2007) "Pediatric Patients With Eosinophilic Esophagitis: An 8-year Follow-up", The Journal of Allergy and Clinical Immunology, 119(3):731-738.

Attwood et al. (Jan. 1993) "Esophageal Eosinophilia with Dysphagia. A Distinct Clinicopathologic Syndrome", Digestive Diseases and Sciences, 38(1):109-116.

Aune et al. (Mar. 2009) "Epigenetics and T helper 1 Differentiation", Immunology, 126(3):299-305.

Ayala et al. (May 15, 1996) "Differential Induction of Apoptosis in Lymphoid Tissues during Sepsis: Variation in Onset, Frequency, and the Nature of the Mediators", Blood, 87(10):4261-4275.

Azouz et al. (May 27, 2020) "Functional Role of Kallikrein 5 and Proteinase-activated Receptor 2 in Eosinophilic Esophagitis", Science Translational Medicine, eaaz7773, 12(545):34 pages.

Azouz et al. (Feb. 2016) "Loss of SPINK7 in Esophageal Epithelial Cells Unleashes a Pro-Inflammatory Response Characterized By Excessive Cytokine Production and Loss of Barrier Function", The Journal of Allergy and Clinical Immunology, 137(2):1 page.

Azouz et al. (Jun. 6, 2818) "The Antiprotease SPINK7 Serves as an Inhibitory Checkpoint for Esophageal Epithelial Inflammatory Responses", Science Translational Medicine, 10(444):29 pages.

Baker et al. (Apr. 2, 2003) "The Central Role of Receiver Operating Characteristic (ROC) Curves in Evaluating Tests for the Early Detection of Cancer", Journal of the National Cancer Institute, 95(7):511-515.

Baldrick et al. (Jul.-Aug. 2007) "Pollinex Quattro Ragweed: Safety Evaluation of a New Allergy Vaccine Adjuvanted with Monophosphoryl Lipid a (MPL) for the Treatment of Ragweed Pollen Allergy", Journal of Applied Toxicology, 27(4):399-409.

Barratt et al. (Apr. 18, 2012) "ABCB1 haplotype and OPRM1 118A > G genotype interaction in methadone maintenance treatment pharmacogenetics", 5(1):53-62.

Barski et al. (Oct. 2009) "Chromatin Poises miRNA- and Protein-coding Genes for Expression", Genome Research, 19(10):1742-151.

Bass D.A. (Jun. 1975) "Behavior of Eosinophil Leukocytes in Acute Inflammation. I. Lack of Dependence on Adrenal Function", Journal of Clinical Investigation, 55(6):1229-1236.

Bass D.A. (Oct. 1975) "Behavior of Eosinophil Leukocytes in Acute Inflammation II. Eosinophil Dynamics During Acute Inflammation", Journal of Clinical Investigation, 56(4):870-879.

Ben-Dor et al. (2000) "Tissue Classification with Gene Expression Profiles", Journal of Computational Biology, 7(3-4):559-583.

Berkman et al. (Jun. 2001) "Eotaxin-3 but Not Eotaxin Gene Expression Is Upregulated in Asthmatics 24 Hours after Allergen Challenge", American Journal of Respiratory Cell and Molecular Biology, 24(6):682-687.

Bhattacharya et al. (Dec. 2007) "Increased Expression of Eotaxin-3 Distinguishes Between Eosinophilic Esophagitis and Gastroesophageal Reflux Disease", Human Pathology, 38(12):1744-1753.

Biesiada et al. (Nov. 2014) "Genetic risk signatures of opioid-induced respiratory depression following pediatric tonsillectomy", Pharmacogenomics, 15(14):1749-1762.

Biton et al. (Mar. 2011) "Epithelial MicroRNAs Regulate Gut Mucosal Immunity Via Epithelium-T Cell Crosstalk", Nature Immunology, 12(3):239-246.

Blanchard et al. (Jan. 2011) "A Striking Local Esophageal Cytokine Expression Profile in Eosinophilic Esophagitis", The Journal of Allergy and Clinical Immunology, e7, 127(1):208-217.

Blanchard et al. (Jan. 2008) "Basics Pathogenesis of Eosinophilic Esophagitis", Gastrointestinal Endoscopy Clinics of North America, 18(1):133-143.

Blanchard et al. (Apr. 1, 2010) "Coordinate Interaction Between IL-13 and Epithelial Differentiation Cluster Genes in Eosinophilic Esophagitis", Journal of Immunology, 184(7):4033-4041.

Blanchard et al. (Sep. 19, 2006) "Eosinophilic Esophagitis: Pathogenesis, Genetics, and Therapy", The Journal of Allergy and Clinical Immunology, 118(5):1054-1059.

Blanchard et al. (Feb. 2006) "Eotaxin-3 and a Uniquely Conserved Gene-Expression Profile in Eosinophilic Esophagitis", Journal of Clinical investigation, 116(2):536-547.

Blanchard et al. (Dec. 2005) "Eotaxin-3/CCL26 Gene Expression in Intestinal Epithelial Cells is Up-regulated by Interleukin-4 and Interleukin-13 Via the Signal Transducer and Activator of Transcription 6", The International Journal of Biochemistry & Cell Biology, 37(12):2559-2573.

Blanchard et al. (Dec. 2007) "IL-13 Involvement in Eosinophilic Esophagitis: Transcriptome Analysis and Reversibility with Glucocorticoids", Journal of Allergy and Clinical Immunology, 120(6):1292-1300.

Blanchard et al. (Jan. 2007) "Il-13 Is Overexpressed in Eosinophilic Esophagitis and Induces Eotaxin-3 Expression in Esophageal Epithelial Cells", The Journal of Allergy and Clinical Immunology, S240, 1 page.

Blanchard et al. (Aug. 24, 2005) "Inhibition of Human Interleukin-13-induced Respiratory and Oesophageal Inflammation by Anti-human-interleukin-13 Antibody (CAT-354)", Clinical and Experimental Allergy, 35(8):1096-1103.

Blanchard et al. (Jul. 2008) "Periostin Facilitates Eosinophil Tissue Infiltration in Allergic Lung and Esophageal Responses", Mucosal Immunology, 1(4):289-296.

Blennow Kaj (Apr. 2004) "Cerebrospinal Fluid Protein Biomarkers for Alzheimer's Disease", NeuroRx, 1 (2):213-225.

Bochner et al. (Jul. 2010) "What Targeting the Eosinophil has Taught Us About their Role in Diseases", The Journal of Allergy and Clinical Immunology, 126(1):16-25.

Boeuf et al. (Mar. 4, 2005) "CyProQuant-PCR: A Real Time RT-PCR Technique for Profiling Human Cytokines, Based on External RNA Standards, Readily Automatable for Clinical Use", BMC Immunology, 6:14 pages.

Bonini et al. (Oct. 1, 1996) "Circulating Nerve Growth Factor Levels are Increased in Humans with Allergic Diseases and Asthma", Proceedings of the National Academy of Sciences of the United States of America, 93 (20):10955-10960.

Boon et al. (Oct. 23, 2003) "Comparison of Medulloblastoma and Normal Neural Transcriptomes Identifies a Restricted Set of Activated Genes", Oncogene, 22(48):7687-7694.

Branford et al. (Jul. 27, 2012) "Opioid genetics: the key to personalized pain control?", Clinical Genetics, 82(4):301-310.

Brightling et al. (Jan. 2010) "Interleukin-13: Prospects for New Treatments", Clinical & Experimental Allergy, 40(1):42-49.

Brodeur et al. (Jan. 1997) "Expression of TrkA, TrkB and TrkC in Human Neuroblastomas", Journal of Neuro-Oncology, 31(1-2):49-55.

(56) References Cited

OTHER PUBLICATIONS

Broide et al. (Mar. 2011) "Advances in Mechanisms of Asthma, Allergy, and Immunology in 2010", The Journal of Allergy and Clinical Immunology, 127(3):689-695.
Broide et al. (2009) "Immunomodulation of Allergic Disease", Annual Review of Medicine, 60:279-291.
Buitenhuis et al. (Jun. 1, 2005) "Differential Regulation of Granulopoiesis by the Basic Helix-loop-helix Transcriptional Inhibitors Id1 and Id2", Blood, 105(11):4272-4281.
Bullens et al. (Nov. 3, 2006) "IL-17 mRNA in Sputum of Asthmatic Patients: Linking T Cell Driven Inflammation and Granulocytic Influx?", Respiratory Research, 7(1):9 pages.
Bullock et al. (Jul. 2007) "Interplay of Adaptive Th2 Immunity with Eotaxin-3/c-C Chemokine Receptor 3 in Eosinophilic Esophagitis", Journal of Pediatric Gastroenterology and Nutrition, 45(1):22-31.
Burnett et al. (Jan. 27, 2012) "RNA-based Therapeutics: Current Progress and Future Prospects", Chemistry & Biology, 19(1):60-71.
Buscaglia et al. (Jun. 2011) "Apoptosis and the Target Genes of MicroRNA-21", Chinese Journal of Cancer, 30(6):371-380.
Busse et al. (Apr. 2010) "A Review of Treatment with Mepolizumab, an Anti-il-5 Mab, in Hypereosinophilic Syndromes and Asthma", The Journal of Allergy and Clinical Immunology, 25(4):803-813.
Cai et al. (Mar. 2017) "The Imprinted H19 Noncoding RNA is a Primary MicroRNA Precursor", RNA, 13(3):313-316.
Caldwell et al. (Sep. 2017) "Cadherin 26 is an alpha integrin-binding epithelial receptor regulated during allergic inflammation", Mucosal Immunology, 10(5):1190-1201.
Caldwell et al. (Feb. 2011) "Global Gene Expression Profile Analysis in Eosinophilic Gastritis Identifies CDH26", The Journal of Allergy and Clinical Immunology, Abstract 831, 127(2):1 page.
Caldwell et al. (Apr. 2010) "Glucocorticoid-regulated Genes in Eosinophilic Esophagitis: A Role for FKBP51", American Academy of Allergy, Asthma & Immunology, 125(4):879-888.
Cameron et al. (Mar. 2000) "Evidence for Local Eosinophil Differentiation Within Allergic Nasal Mucosa: Inhibition with Soluble IL-5 Receptor", The Journal of Immunology, 164(3):1538-1545.
Tian et al. (Oct. 1, 2010) "Visualizing of the Cellular Uptake and Intracellular Trafficking of Exosomes by Live-cell Microscopy", Journal of Cellular Biochemistry, 111(2):488-496.
Tkachuk et al. (Nov. 19, 1996) "Regulation and Role of Urokinase Plasminogen Activator in Vascular Remodelling", Clinical and Experimental Pharmacology and Physiology, 23(9):759-765.
Todorov et al. (2018) "Principal Components Analysis: Theory and Applicaiton to Gene Expression Data Analysis", Genomics and Computational Biology, e100041, 4(2):7 pages.
Trapnell et al. (Apr. 2009) "TopHat: Discovering Splice Junctions with RNA-Seq", Bioinformatics, 25(9):1105-1111.
Trapnell et al. (May 2010) "Transcript Assembly and Quantification By RNA-seq Reveals Unannotated Transcripts and Isoform Switching During Cell Differentiation", Nature Biotechnology, 28(5):511-515.
Tsang et al. (Mar. 2010) "Oncofetal H19-derived MIR-675 Regulates Tumor Suppressor RB In Human Colorectal Cance", Carcinogenesis, 31(3):350-358.
Tsuchiya et al. (Jan. 7, 2011) "MicroRNA-210 Regulates Cancer Cell Proliferation through Targeting Fibroblast Growth Factor Receptor-like 1 (FGFRLI)", Journal of Biological Chemistry, 286(1):420-428.
Tsukamoto et al. (Mar. 15, 2010) "MicroRNA-375 is Downregulated in Gastric Carcinomas and Regulates Cell Survival by Targeting PDK1 and 14-3-3ζ", Cancer Research, 70(6):2339-2349.
Tzvetkov et al. (Jul. 5, 2013) "Morphine is a substrate of the organic cation transporter OCT1 and polymorphisms in OCT1 gene affect morphine pharmacokinetics after codeine administration", Biochemical Pharmacology, 86(5):666-678.
Ueda et al. (Jun. 6, 2005) "Inflammation and the Reciprocal Production of Granulocytes and Lymphocytes in Bone Marrow", Journal of Experimental Medicine, 201(11):1771-1780.
Vaishnavi et al. (2013) "Oncogenic and Drug-Sensitive NTRK1 Rearrangements in Lung Cancer", Nature Medicine, 19(11):1469-1472.
Valadi et al. (Jun. 2007) "Exosome-Mediated Transfer of mRNA and microRNA is a Novel Mechanism of Genetic Exchange Between Cells", Nature Cell Biology, 9(6):654-659.
Van Rooij et al. (Feb. 3, 2012) "Developing microRNA Therapeutics", Circulation Research, 110(3):496-507.
Vandepapeliere et al. (Jan. 14, 2008) "Vaccine Adjuvant Systems Containing Monophosphoryl Lipid A and QS21 Induce Strong C63 and Persistent Humoral and T Cell Responses Against Hepatitis B Surface Antigen in Healthy Adult Volunteers", Vaccine, 33(8):1084-1091.
Varnes et al. (Apr. 5, 2004) "Discovery of N-propylurea 3-benzylpiperidines as Selective CC Chemokine Receptor-3 (CCR3) Antagonists", Bioorganic & Medicinal Chemistry Letters, 14(7):1645-1649.
Velasco et al. (Mar. 2005) "Toll-like Receptor 4 or 2 Agonists Decrease Allergic Inflammation", American Journal of Respiratory Cell and Molecular Biology, 32(3):218-224.
Velu et al. (May 7, 2009) "Gfi1 Regulates miR-21 and miR-196b to Control Myelopoiesis", Blood, 113 (19):4720-4728.
Venek et al. (2014) "Adolescent Suicidal Risk Assessment in Clinician-Patient Interaction: A Study of Verbal and Acoustic Behaviors", Spoken Language Technology Workshop, 6 pages.
Venge Per (May 2010) "The Eosinophil and Airway Remodelling in Asthma", The Clinical Respiratory Journal, 4 (Suppl 1):15-19.
Venkatasubramanian et al. (Jul. 2014) "ABCC3 and OCT1 genotypes influence pharmacokinetics of morphine in children", Pharmacogenomics, 15(10):1297-1309.
Verspoor et al. (Jun. 15, 2009) "The textual characteristics of traditional and Open Access scientific journals are similar", BMC Bioinformatics, 10:183.
Mcario et al. (Jan. 2010) "Local B Cells and IgE Production in the Oesophageal Mucosa in Eosinophilic Oesophagitis", Gut, 59(1):12-20.
Vincent et al. (Dec. 2, 2009) "International Study of the Prevalence and Outcomes of Infection in Intensive Care Units", JAMA, 302(21):2323-2329.
Von Ahlfen et al. (2007) "Determinants of RNA Quality from FFPE Samples", PLoS One, e1261, 2(12): 7 pages.
Von Arnim et al. (2014) "Eosinophilic Esophagitis—Treatment of Eosinophilic Esophagitis with Drugs: Corticosteroids", Digestive Diseases, 32(1-2):126-129.
Wacker et al. (Jul. 8, 2002) "CCR3 Antagonists: A Potential New Therapy for the Treatment of Asthma. Discovery and Structure-activity Relationships", Bioorganic & Medicinal Chemistry Letters, 12(13):1785-1789.
Wan et al. (Feb. 2004) "Foxa2 Regulates Alveolarization and Goblet Cell Hyperplasia", Development, 131(4):953-964.
Wang et al. (May 2010) "Differential Functions of Growth Factor Receptor-Bound Protein 7 (GRB7) and Its Variant GRB7v in Ovarian Carcinogenesis", Clinical Cancer Research, 16(9):2529-2539.
Wen et al. (Oct. 19, 2014) "Transcriptome analysis of proton pump inhibitor-responsive esophageal eosinophilia reveals proton pump inhibitor-reversible allergic inflammation", Journal of Allergy and Clinical Immunology, 135(1):187-197.
White (Nov. 24, 2000) "Identification of Potent, Selective Non-peptide CC Chemokine Receptor-3 Antagonist that Inhibits Eotaxin-, Eotaxin-2-, and Monocyte Chemotactic Protein-4-induced Eosinophil Migration", The Journal of Biological Chemistry, 275(47):36626-36631.
Wills-Karp Marsha (Dec. 2004) "Interleukin-13 in Asthma Pathogenesis", Immunological Reviews, 202:175-190.
Winter et al. (Mar. 2009) "Many Roads to Maturity: microRNA Biogenesis Pathways and their Regulation", Nature Cell Biology, 11(3):228-234.
Wolska et al. (Apr. 2009) "The Role of Toll-Like Receptors in Hematopoietic Malignancies", Current Molecular Medicine, 9(3):324-335.

(56) References Cited

OTHER PUBLICATIONS

Wong et al. (Jul. 2007) "Intracellular Signaling Mechanisms Regulating Toll-like Receptor-mediated Activation of Eosinophils", American Journal of Respiratory Cell and Molecular Biology, 37(1):85-96.

Wong et al. (Feb. 2013) "Microrna-21 Regulates the Prosurvival Effect of GM-CSF on Human Eosinophils", Immunobiology, 218(2):255-262.

Woodruff et al. (Oct. 2, 2007) "Genome-wide Profiling Identifies Epithelial Cell Genes Associated with Asthma and With Treatment Response to Corticosteroids", Proceedings of the National Academy of Sciences of the United States of America, 10(40):15858-15863.

Wu et al. (Nov. 2008) "MicroRNAs Are Differentially Expressed in Ulcerative Colitis and Alter Expression of Macrophage Inflammatory Peptide-2a", Gastroenterology, e24, 135(5):1624-1635.

Xanthou Marietta (Sep. 2008) "Leucocyte Blood Picture in III Newborn Babies", Archives of Disease in Childhood, 47(255):741-746.

Xiang et al. (Feb. 15, 2008) "Wound Repair and Proliferation of Bronchial Epithelial Cells Regulated by CTNNAL1", Journal of Cellular Biochemistry, 103(3):920-930.

Xing et al. (Aug. 23, 2011) "Protease Phenotype of Constitutive Connective Tissue and of Induced Mucosal Mast Cells in Mice Is Regulated by the Tissue", Proceedings of the National Academy of Sciences of the United States of America, 108(34):4210-1421.

Yamazaki et al. (Nov. 2006) "Allergen-specific In Vitro Cytokine Production in Adult Patients with Eosinophilic Esophagitis", Digestive Diseases and Sciences, 51(11):1934-1941.

Yang et al. (Oct. 15, 2006) "Inhibition of Arginase I Activity by RNA Interference Attenuates IL-13-Induced Airways Hyperresponsiveness", The Journal of Immunology, 177(8):5595-5603.

Yang et al. (May 2009) "Th17 and Natural Treg Cell Population Dynamics in Systemic Lupus Erythematosus", Arthritis & Rheumatology, 60(5);1472-1483.

Yee et al. (Jul. 3, 2012) "Insulin-like Growth Factor Receptor Inhibitors: Baby or the Bathwater?", Journal of the National Cancer Institute, 104(13):975-981.

Yi et al. (Mar. 13, 2008) "A Skin MicroRNA Promotes Differentiation by Repressing 'Stemness'", Nature, 452(7184):225-229.

Yin et al. (Jan. 2010) "Targeting the Insulin-like Growth Factor-1 Receptor by Picropodophyllin as a Treatment Option for Glioblastoma", Neuro-Oncology, 12(1):19-27.

Yousefi et al. (Aug. 10, 2008) "Catapult-like Release of Mitochondrial DNA by Eosinophils Contributes to Antibacterial Defense", Nature Medicine, 14(9):949-953.

Yuan et al. (Feb. 7, 2011) "Microrna-203 Inhibits Cell Proliferation by Repressing Anp63 Expression in Human Esophageal Squamous Cell Carcinoma", BMC Cancer, 11:10 pages.

Kaur et al. (Jul. 1, 2002) "Rofecoxib Inhibits Cyclooxygenase 2 Expression and Activity and Reduces Cell Proliferation in Barrett's Esophagus", Gastroenterology, 123(1):60-67.

Kelly et al. (Apr. 9, 2012) "More codeine fatalities after tonsillectomy in North American children", Pediatrics, 129(5):e1343-1347.

Kerstjens et al. (Oct. 2019) "Airway Pharmacology: Treatment Options and Algorithms to Treat Patients with Chronic Obstructive Pulmonary Disease", Journal of Thoracic Disease, 11(S17):S2200-S2209.

Kihara et al. (Sep. 1, 2001) "Prediction of Sensitivity of Esophageal Tumors to Adjuvant Chemotherapy by cDNA Microarray Analysis of Gene-expression Profiles", Cancer Research, 61(17):6474-6479.

Kim et al. (2004) "Microarray Applications in Cancer Research", Cancer Research and Treatment, 36(4):207-213.

Kim et al. (Dec. 2004) "Rebound Eosinophilia after Treatment of Hypereosinophilic Syndrome and Eosinophilic Gastroenteritis with Monoclonal Anti-IL-5 Antibody SCH55700", The Journal of Allergy and Clinical Immunology, 114(6):1449-1455.

Kledal et al. (Sep. 12, 1997) "A Broad-Spectrum Chemokine Antagonist Encoded by Kaposi's Sarcoma-Associated Herpesvirus", Science, 277(5332):1656-1659.

Klingelhöfer et al. (Nov. 2002) "Dynamic Interplay Between Adhesive and Lateral E-Cadherin Dimers", Molecular and Cellular Biology, 22(21):7449-7458.

Komiya et al. (Oct. 2003) "Concerted Expression of Eotaxin-1, Eotaxin-2, and Eotaxin-3 in Human Bronchial Epithelial Cells", Cellular Immunology, 225(2):91-100.

Kong et al., (Jan. 2012) "MicroRNA-375 Inhibits Tumour Growth and Metastasis in Oesophageal Squamous Cell Carcinoma Through Repressing Insulin-like Growth Factor 1 Receptor", Gut., 61(1):33-42.

Konikoff et al. (Nov. 2006) "A Randomized, Double-blind, Placebo-controlled Trial of Fluticasone Propionate for Pediatric Eosinophilic Esophagitis", Gastroenterology, 131(5):1381-1391.

Konturek et al. (Aug. 2004) "Activation of NFκB Represents the Central Event in the Neoplastic Progression Associated with Barrett's Esophagus: A Possible Link to the Inflammation and Overexpression of COX-2, PPARγ and Growth Factors", Digestive Diseases and Sciences, 49(7-8):1075-1083.

Kottyan et al. (Jul. 13, 2014) "Genome-wide Association Analysis of Eosinophilic Esophagitis Provides Insight into the Tissue Specificity of this Allergic Disease", Nature Genetics, 46(8):895-900.

Kouro et al. (Dec. 2009) "IL-5- and Eosinophil-mediated Inflammation: From Discovery to Therapy", International Immunology, 21(12):1303-1309.

Krichevsky et al. (Jan. 2009) "MIR-21: A Small Multi-faceted RNA", Journal of Cellular and Molecular Medicine, 13(1):39-53.

Krutzfeldt et al. (Dec. 1, 2005) "Silencing of MicroRNAs in Vivo with 'Antagomirs'", Nature, 438 (7068):685-689.

Kumar et al. (Nov. 2011) "Let-7 microRNA-mediated Regulation of IL-13 and Allergic Airway Inflammation", The Journal of Allergy and Clinical Immunology, e10, 128(5):1077-1085.

Kuperman et al. (Aug. 2002) "Direct Effects of Interleukin-13 on Epithelial Cells Cause Airway Hyperreactivity and Mucus Overproduction in Asthma", Nature Medicine, 8(8):885-889.

Kuperman et al. (Mar. 16, 1998) "Signal Transducer and Activator of Transcription Factor 6 (Stat6)-deficient Mice are Protected from Antigen-induced Airway Hyperresponsiveness and Mucus Production", Journal of Experimental Medicine, 187(6):939-948.

Laprise et al. (Mar. 23, 2004) "Functional Classes of Bronchial Mucosa Genes that are Differentially Expressed in Asthma", BMC Genomics, 5(1):10 pages.

Lavigne et al. (Nov. 12, 2004) "Human Bronchial Epithelial Cells Express and Secrete MMP-12", Biochemical and Biophysical Research Communications, 324(2):534-546.

Lee et al. (Apr. 2010) "Eosinophils in Health and Disease: The LIAR Hypothesis", Clinical & Experimental Allergy, 40(4):563-575.

Lee et al. (Jan. 2006) "ERK1/2 Mitogen-activated Protein Kinase Selectively Mediates IL-13-induced Lung Inflammation and Remodeling in Vivo", Journal of Clinical Investigation, 116(1):163-173.

Lee et al. (Oct. 2001) "Interleukin-13 Induces Dramatically Different Transcriptional Programs in Three Human Airway Cell Types", American Journal of Respiratory Cell and Molecular, 25(4):474-485.

Lei et al. (Mar. 2007) "Transcriptional Regulation of Trk Family Neurotrophin Receptors", Cellular and Molecular Life Sciences, 64(5):522-532.

Leigh et al. (Apr. 1, 2004) "Type 2 Cytokines in the Pathogenesis of Sustained Airway Dysfunction and Airway Remodeling in Mice", American Journal of Respiratory and Critical Care Medicine, 169(7):860-867.

Leschziner et al. (Sep. 12, 2006) "ABCB1 genotype and PGP expression, function and therapeutic drug response: a critical review and recommendations for future research", The Pharmacogenomics Journal, 7(3):154-179.

Letunic et al. (Jan. 2012) "SMART 7: Recent Updates to the Protein Domain Annotation Resource", Nucleic Acids Research, 40:D302-D305.

Levi-Montalcini R. (Sep. 4, 1987) "The Nerve Growth Factor 35 Years Late", Science, 237 (4819):1154-1162.

Li et al. (Oct. 2011) "Epigenetic Silencing of microRNA-375 Regulates PDKI Expression in Esophageal Cancer", Digestive Diseases and Sciences, 56(10):2849-2856.

(56) References Cited

OTHER PUBLICATIONS

Li et al. (Mar. 31, 2011) "miR-223 Regulates Migration and Invasion by Targeting Artemin in Human Esophageal Carcinoma", Journal of Biomedical Science, 18(1):9 pages.
Liacouras et al. (Jul. 2011) "Eosinophilic Esophagitis: Updated Consensus Recommendations for Children and Adults", Journal of Allergy and Clinical Immunology, 128(1):3-26.
Liacouras et al. (Sep. 2007) "Summary of the First International Gastrointestinal Eosinophil Research Symposium", Journal of Pediatric Gastroenterology and Nutrition, 45(3):370-391.
Liesveld Jane (Dec. 2018) "Hypereosinophilic Syndrome", MSD Manual Professional Version, 5 Pages.
Lim et al. (Jan. 1, 2014) "Demethylation of the Human Eotaxin-3 Gene Promoter Leads to the Elevated Expression of Eotaxin-3", Journal of Immunology, 192(1):466-474.
Lim et al. (Apr. 15, 2011) "Epigenetic Regulation of the IL-13-induced Human Eotaxin-3 Gene by CREB-binding Protein-mediated Histone 3 Acetylation", Journal of Biological Chemistry, 286(15):13193-13204.
Lin et al. (Mar. 31, 2011) "miR-142-3p as a Potential Prognostic Biomarker for Esophageal Squamous Cell Carcinoma", Journal of Surgical Oncology, 105(2):175-182.
Linch et al. (Nov. 2009) "Mouse Eosinophils Possess Potent Antibacterial Properties in Vivo", Infection and Immunity, 77(11):4976-4982.
Linch et al. (Jun. 2011) "The Role of Eosinophils in Non-parasitic Infections", Endocrine, Metabolic & Immune Disorders—Drug Targets, 11(2):165-172.
Lipkin Stefanien. (Apr. 1979) "Eosinophil Counts in Bacteremia", Archives of Internal Medicin, 139(4):490-491.
Liu et al. (Feb. 2012) "Role of microRNA let-7 and Effect to HMGA2 in Esophageal Squamous Cell Carcinoma", Molecular Biology Reports, 39(2):1239-1246.
Livak et al. (2001) "Analysis of Relative Gene Expression Data using Real- Time Quantitative PCR and the 2-Delta DeltaCT Method", Methods, 25:402-408.
Lo et al. (Dec. 16, 2011) "Identification of a Novel Mouse p53 Target Gene DDA3", Oncogene, 18 (54):7765-7774.
Long et al. (Jun. 1, 2002) "Disruption of the NAD(P)H:quinone Oxidoreductase 1 (NQO1) Gene in Mice Causes Myelogenous Hyperplasia", Cancer Research, 62(11):3030-3036.
Lovinsky-Desir et al. (Jun. 2012) "Epigenetics, Asthma, and Allergic Diseases: A Review of the Latest Advancements", Current Allergy and Asthma Reports, 12(3):211-220.
Lu et al. (2013) "Diagnostic, functional, and therapeutic roles of microRNA in allergic diseases", Journal of Allergy and Clinical Immunology, 132(1):3-13.
Lu et al. (Sep. 17, 2010) "Function of miR-146a in Controlling Treg Cell-mediated Regulation of Th1 Responses", Cell, 142(6):914-929.
Lu et al. (Jul. 16, 2012) "MicroRNA Profiling in Mucosal Biopsies of Eosinophilic Esophagitis Patients Pre and Post Treatment with Steroids and Relationship with mRNA Targets", PLoS One, e40676, 7(7):11 pages.
Lu et al. (Apr. 2012) "MicroRNA signature in Patients with Eosinophilic Esophagitis, Reversibility with Glucocorticoids, and Assessment as Disease Biomarkers", The Journal of Allergy and Clinical Immunology, e9, 129(4):1064-1075.
Lu et al. (Apr. 15, 2009) "MicroRNA-21 is Up-Regulated in Allergic Airway Inflammation and Regulates IL-12p35 Expression", Journal of Immunology, 182(8):4994-5002.
Shinkai et al. (Protein Engineering (2002) vol. 15, pp. 923-929).
Elsner et al. 1997. Euro. J. of Immuno. vol. 27, pp. 2892-2898.
GeneSpring User Manual, version 6.1. Silicon Genetics. Nov. 14, 2003.
Sinicropi et al., BioMEMS and biomedical nanotechnology. Springer US, 2006. 23-46.
"rs77569859", Dec. 16, 2010, pp. 1-2, Retrieved from the Internet: URL: http://www.ncbi.nlm.nih.gov/projects/SNP/snp-SS.cgi?subsnp_id=276404309.
"rs2898261", Dec. 16, 2010, pp. 1-2, Retrieved from the Internet: URL: http://www.ncbi.nlm.nih.gov/projects/SNP/snp-SS.cgi?subsnp_id=279682708.
"rs8041227", Dec. 16, 2010, pp. 1-2, Retrieved from the Internet: URL: http://www.ncbi.nlm.nih.gov/projects/SNP/snp-SS.cgi?subsnp_id=90109558.
Caldwell. J. Allergy. Clin. Immuno. 134:1114-24 (2014).
Eisen et al. 1998. Proc. Natl. Acad. Sci. USA (25)95, p. 14863-14868.
Shoda et al. Lancet. Gastroenterology Hepatol. Jul. 2018; 3(7):477-488; Epub 2018.
Sato et al. J. Allergy Clin. Immuno. Pract. 2017, 5(6):1639-1649.
Descamps et al., Cancer Res. 61, 4337-4340 (2001).
Madhusudan et al. Resent Results Cancer Res. 172:25-44.
Prakash et al. Expert Rev. Resp. Med. 4(3), 395-411 (2010).
Oyoshi Current Opinion in Pediatrics, 2015, 27(6), 741-747.
Chen et al. Jiepoukexue Jinzhan (2007), 13(4), 388-391.
Rochlitzer et al. Biochem Soc. Trans (2006), 34(4), 594-599.
Nassenstein et al. J. Allergy Clin. Immuno. 2006; 118:597-605.
Weber et al. Experimental Dermatology, 2014. vol. 23, pp. 1-52.
International Search Report and Written Opinion, PCT/US2016/068236 dated Dec. 22, 2016.
Valeska et al. 2019. Gastroenterology. 156(6, Suppl. 1) S619. 1 page.
Wang et al. 1994. J. Immuno. 152(10):5014-5021.
European Search Report and Written Opinion for the Application No. 12732079.4 Apr. 22, 2014, 11 pages.
Recombinant Mouse N-Cadherin Fc Chimera Protein, Cf 6626-NC . . . https://www.mndsysytems.com> N-Cadherin Jan. 14, 2011—Mouse N-Caderin protein (6626-NC) is manufactured by R&D Systems. Retrieved Aug. 15, 2018.
Recombinant Human VE-Cadherin Fc Chimera Protein, CF . . . https://www.mndsysytems.com> N-Cadherin Jul. 4, 2015—Huamn VW-Caderin protein (938-VC) is manufactured by R&D Systems. Retrieved Aug. 15, 2018.
Ishihara, Shunji et al. "Serum Biomarkers for the Diagnosis of Eosinophilic Esophagitis and Eosinophilic Gastroenteritis." Internal medicine (Tokyo, Japan) vol. 56,21 (2017): 2819-2825.
Shoda, Tetsuo et al. "Sera of patients with infantile eosinophilic gastroenteritis showed a specific increase in both thymic stromal lymphopoietin and IL-33 levels." The Journal of allergy and clinical immunology vol. 138, 1 (2016):299-303.

* cited by examiner

Wilcoxon / Kruskal-Wallis Tests (Rank Sums)

| Level | Count | Score Sum | Expected Score | Score Mean | (Mean-Mean0)/Std0 |
|---|---|---|---|---|---|
| EoEe1 | 30 | 1752.00 | 1305.00 | 58.4000 | 4.046 |
| EoEe2 | 25 | 1355.00 | 1087.50 | 54.2000 | 2.539 |
| EoEe3 | 31 | 634.000 | 1348.50 | 20.4516 | -6.422 |

1-Way Test, ChiSquare Approximation

| ChiSquare | DF | Prob>ChiSq |
|---|---|---|
| 41.6850 | 2 | <.0001* |

Nonparametric Comparisons For All Pairs Using Dunn Method For Joint Ranking

| Level | - Level | Score Mean Difference | Std Err Dif | Z | p-Value |
|---|---|---|---|---|---|
| EoEe2 | EoEe1 | -4.1633 | 6.761903 | -0.61570 | 1.0000 |
| EoEe3 | EoEe2 | -33.7123 | 6.712146 | -5.02258 | <.0001* |
| EoEe3 | EoEe1 | -37.9156 | 6.395017 | -5.92893 | <.0001* |

| Wilcoxon / Kruskal-Wallis Tests (Rank Sums) | | | | | |
|---|---|---|---|---|---|
| Level | Count | Score Sum | Expected Score | Score Mean | (Mean-Mean0)/Std0 |
| EoEe1 | 30 | 1925.00 | 1305.00 | 64.1667 | 5.613 |
| EoEe2 | 25 | 1127.00 | 1087.50 | 45.0800 | 0.371 |
| EoEe3 | 31 | 689.000 | 1348.50 | 22.2258 | -5.927 |

| 1-Way Test, ChiSquare Approximation | | |
|---|---|---|
| ChiSquare | DF | Prob>ChiSq |
| 43.1533 | 2 | <.0001* |

| Nonparametric Comparisons For All Pairs Using Dunn Method For Joint Ranking | | | | | |
|---|---|---|---|---|---|
| Level | - Level | Score Mean Difference | Std Err Dif | Z | p-Value |
| EoEe2 | EoEe1 | -19.0500 | 6.761903 | -2.81725 | 0.0145* |
| EoEe3 | EoEe2 | -22.8181 | 6.712146 | -3.39952 | 0.0020* |
| EoEe3 | EoEe1 | -41.9081 | 6.395017 | -6.55324 | <.0001* |

Wilcoxon / Kruskal-Wallis Tests (Rank Sums)

| Level | Count | Score Sum | Expected Score | Score Mean | (Mean-Mean0)/Std0 |
|---|---|---|---|---|---|
| EoEe1 | 30 | 1021.00 | 1305.00 | 34.0333 | -2.569 |
| EoEe2 | 25 | 1742.00 | 1087.50 | 69.6800 | 6.220 |
| EoEe3 | 31 | 978.000 | 1348.50 | 31.5484 | -3.328 |

1-Way Test, ChiSquare Approximation

| ChiSquare | DF | Prob>ChiSq |
|---|---|---|
| 38.8956 | 2 | <.0001* |

Nonparametric Comparisons For All Pairs Using Dunn Method For Joint Ranking

| Level | - Level | Score Mean Difference | Std Err Dif | Z | p-Value |
|---|---|---|---|---|---|
| EoEe2 | EoEe1 | 35.6100 | 6.761903 | 5.26627 | <.0001* |
| EoEe3 | EoEe1 | -2.4522 | 6.395017 | -0.38345 | 1.0000 |
| EoEe3 | EoEe2 | -38.0955 | 6.712146 | -5.67560 | <.0001* |

| Wilcoxon / Kruskal-Wallis Tests (Rank Sums) | | | | | |
|---|---|---|---|---|---|
| Level | Count | Score Sum | Expected Score | Score Mean | (Mean-Mean0)/Std0 |
| EoEe1 | 30 | 1974.00 | 1305.00 | 65.8000 | 6.057 |
| EoEe2 | 25 | 945.000 | 1087.50 | 37.8000 | -1.350 |
| EoEe3 | 31 | 822.000 | 1348.50 | 26.5161 | -4.731 |

| 1-Way Test, ChiSquare Approximation | | |
|---|---|---|
| ChiSquare | DF | Prob>ChiSq |
| 39.5717 | 2 | <.0001* |

| Nonparametric Comparisons For All Pairs Using Dunn Method For Joint Ranking | | | | | |
|---|---|---|---|---|---|
| Level | - Level | Score Mean Difference | Std Err Dif | Z | p-Value |
| EoEe3 | EoEe2 | -11.2477 | 6.712146 | -1.67573 | 0.2814 |
| EoEe2 | EoEe1 | -27.9633 | 6.761903 | -4.13542 | 0.0001* |
| EoEe3 | EoEe1 | -39.2511 | 6.395017 | -6.13776 | <.0001* |

| Wilcoxon / Kruskal-Wallis Tests (Rank Sums) | | | | | |
|---|---|---|---|---|---|
| Level | Count | Score Sum | Expected Score | Score Mean | (Mean-Mean0)/Std0 |
| EoEe1 | 30 | 498.000 | 1305.00 | 16.6000 | -7.308 |
| EoEe2 | 25 | 1708.00 | 1087.50 | 68.3200 | 5.896 |
| EoEe3 | 31 | 1535.00 | 1348.50 | 49.5161 | 1.673 |

| 1-Way Test, ChiSquare Approximation | | |
|---|---|---|
| ChiSquare | DF | Prob>ChiSq |
| 61.3169 | 2 | <.0001* |

| Nonparametric Comparisons For All Pairs Using Dunn Method For Joint Ranking | | | | | |
|---|---|---|---|---|---|
| Level | - Level | Score Mean Difference | Std Err Dif | Z | p-Value |
| EoEe2 | EoEe1 | 51.6833 | 6.761903 | 7.64331 | <.0001* |
| EoEe3 | EoEe1 | 32.8833 | 6.395017 | 5.14202 | <.0001* |
| EoEe3 | EoEe2 | -18.7677 | 6.712146 | -2.79609 | 0.0155* |

| Wilcoxon / Kruskal-Wallis Tests (Rank Sums) | | | | | |
|---|---|---|---|---|---|
| Level | Count | Score Sum | Expected Score | Score Mean | (Mean-Mean0)/Std0 |
| EoEe1 | 30 | 507.000 | 1305.00 | 16.9000 | -7.226 |
| EoEe2 | 25 | 1745.00 | 1087.50 | 69.8000 | 6.248 |
| EoEe3 | 31 | 1489.00 | 1348.50 | 48.0323 | 1.259 |

| 1-Way Test, ChiSquare Approximation | | |
|---|---|---|
| ChiSquare | DF | Prob>ChiSq |
| 62.8001 | 2 | <.0001* |

| Nonparametric Comparisons For All Pairs Using Dunn Method For Joint Ranking | | | | | |
|---|---|---|---|---|---|
| Level | - Level | Score Mean Difference | Std Err Dif | Z | p-Value |
| EoEe2 | EoEe1 | 52.8633 | 6.761903 | 7.81782 | <.0001* |
| EoEe3 | EoEe1 | 31.0995 | 6.395017 | 4.86308 | <.0001* |
| EoEe3 | EoEe2 | -21.7316 | 6.712146 | -3.23766 | 0.0036* | ns
METHODS FOR TREATING EOSINOPHILIC ESOPHAGITIS

CROSS REFERENCE TO RELATED APPLICATIONS

This application claims the benefit of U.S. Provisional Application No. 62/634,446, filed Feb. 23, 2018, the entire disclosure of which is incorporated herein by reference in its entirety.

STATEMENT REGARDING FEDERALLY-SPONSORED RESEARCH

This invention was made with US government support under Grant Nos. AI045898, AI070235, and AI117804 awarded by the National Institute of Health. The government has certain rights in the invention.

FIELD OF THE INVENTION

The disclosure relates to methods for treating eosinophilic esophagitis by determining the disease endotype.

BACKGROUND OF THE INVENTION

Eosinophilic esophagitis (EoE) is an emerging disease characterized by marked esophageal specific eosinophilia that is typically driven by allergic sensitization to a variety of common foods. Lucendo A J, et al. *United Eur. Gastroent. J.* 2017; 5(3): 335-58. The diagnosis is dependent upon quantitative assessment of esophageal levels of eosinophils (i.e., peak eosinophil count of ≥15 intraepithelial eosinophils in one high-power field [HPF]). Although the gold standard for diagnosing disease and monitoring disease activity is the esophageal eosinophil level, recent advances have identified the potential value of a deeper analysis based on a wide range of quantifiable molecular, endoscopic, and histologic parameters. Warners M J et al. *Am J Gastroenterol* 2017; 112(11): 1658-69; Wen T, Rothenberg M E. Front Med (Lausanne) 2017; 4:108. In particular, a unique EoE transcriptome, referred to as the EoE Diagnostic Panel (EDP), a set of esophageal transcripts that distinguishes EoE from control individuals including those with gastroesophageal reflux disease, correlates with distinct disease features and can identify EoE amongst ambiguous cases. Wen T, et al. *Gastroenterology* 2013; 145(6): 1289-99. In addition, a deeper histologic assessment called the histologic scoring system (HSS) has been described and takes into account disease stage and grade across eight different parameters beyond peak eosinophil levels. Collins et al. *Dis Esophagus* 2017; 30(3): 1-8. Finally, a broad panel of endoscopic features, as measured by EoE endoscopic reference scoring (EREFS), which takes into account five endoscopic features (i.e., concentric rings, longitudinal furrows, white plaques/exudates, edema, and strictures), has significance in terms of understanding clinical features and monitoring the effect of therapy in both children and adults. Wechsler J B, et al. *Clin Gastroenterol Hepatol* 2017.

An outstanding need in the EoE field is to define the relationships between these various clinical, endoscopic, and histologic features (especially the gold standard of the disease, the esophageal eosinophil level) and the degree of patient heterogeneity, as current therapy is not governed by specific disease features. Atkins D, et al. *Pediatr Allergy Immunol* 2017; 28(4): 312-9. Although a fibrostenotic phenotype has been associated with a subset of subjects with EoE, its molecular features, particularly in comparison to a non-fibrostenotic phenotype, has not yet been determined. At present, EoE is treated by food elimination trials, focused on the most highly allergenic foods, and topical glucocorticoid therapy.

An unmet need in the therapy of eosinophilic esophagitis ("EoE") is the ability to identify clinically relevant disease endotypes in EoE patients in order to tailor each patient's treatment to that most likely to benefit the patient's specific form of disease. The present invention addresses this need.

SUMMARY OF THE INVENTION

The present invention is based, in part, on the discovery of three distinct EoE subtypes, referred to herein as disease "endotypes" and more particularly as EoEe1 or "mild", EoEe2 or "intermediate", and EoEe3 or "severe", each of which has characteristic histological and endoscopic features and is associated with distinct clinical characteristics and phenotypes. Collectively, the endotypes described here are useful to stratify patients with EoE into clinically relevant subgroups of mild, intermediate, or severe disease, thereby providing a framework for a precision medicine approach to EoE therapy, as described in more detail below. Generally, the EoEe1 endotype is characterized as having the mildest histological and clinical phenotype, most closely resembling findings seen in healthy tissue of normal biopsies. The EoEe2 endotype is generally characterized by substantial inflammatory changes, type-2 immune responses, and evidence of refractoriness to steroids. The EoEe3 endotype is generally characterized by a strong association with the presence of a narrow-caliber esophagus, the highest degree of endoscopic and histologic severity, and the lowest expression of epithelial differentiation genes. Accordingly, the disclosure provides methods for identifying the EoE endotype of a patient in need of treatment for EoE, including for example a patient diagnosed with EoE, and treating the patient with one or more therapies targeted to the patient's disease endotype, and related methods for stratifying patients for clinical trials.

In embodiments, the disclosure provides methods for treating eosinophilic esophagitis (EoE) in a subject in need thereof, the method comprising subjecting a biological sample from the subject to a method for gene expression analysis, determining the expression of one or more genes or a panel of genes in the biological sample, determining the subject's EoE endotype based on the expression of the one or more genes or panel of genes, and treating the patient with an EoE therapy tailored to the patient's EoE endotype. In embodiments, the EoE endotype is selected from mild, intermediate, and severe.

In embodiments, treating the patient with an EoE therapy tailored to the patient's EoE endotype comprises one or more of the following,
  where the EoE endotype is determined to be mild, treating the patient with one or both of proton pump inhibitor (PPI) therapy and dietary therapy;
  where the EoE endotype is determined to be intermediate, treating the patient with one or more of an anti-cytokine therapy, an anti-TSLP therapy, and an anti-ALOX15 therapy; and
  where the EoE endotype is determined to be severe, treating the patient with one or more of anti-ALOX15 therapy, esophageal dilation, anti-cytokine therapy, and glucocorticoid therapy.

In embodiments, the biological sample is an esophageal biopsy sample.

In embodiments, the determining the expression of one or more genes or a panel of genes in the biological sample is performed using a PCR-based method.

In embodiments, the determining the subject's EoE endotype based on the expression of the one or more genes or panel of genes is performed by a method comprising linear discriminant analysis. In embodiments, the linear discriminant analysis comprises determining a probability distance. In embodiments, the probability distance is the Mahalanobis distance.

In embodiments, the at least one gene or panel of genes comprises one or more of ANO1, CRYM, DSG1, PNLIPRP3, TNFAIP6, TSLP, UPK1A, and WDR36. In embodiments, the at least one gene or panel of genes further comprises one or more of the genes set forth in Table 2. In embodiments, the at least one gene or panel of genes comprises one or more of ALOX15, APOBEC3A, CDA, CRISP3, ACTG2, CCR3, FFAR3, IL4, RGS9BP, TSLP, CTNNAL1, EML1, FLG, PNLIPRP3 and TSPAN12.

In embodiments, the endotype is further characterized by one or more histologic, endoscopic, or clinical features. In embodiments, the one or more histologic features is selected from basal zone hyperplasia (BZH) and surface epithelial alteration (SEA). In embodiments, the one or more endoscopic features is selected from the occurrence of edema, exudates, and furrows. In embodiments, the one or more clinical features is selected from pediatric onset, adult onset, atopic, non-atopic, steroid sensitivity, steroid refractory, and fibrostenotic.

DETAILED DESCRIPTION OF THE INVENTION

Figure 1A:
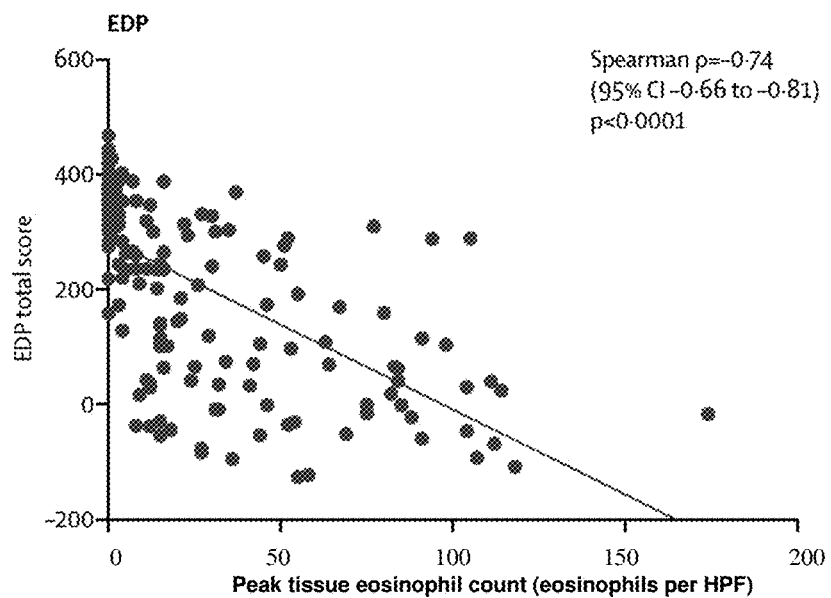
FIG. 1A-C: Associations between peak esophageal eosinophil counts in eosinophilic esophagitis and diagnostic platforms. A linear correlation is seen between peak esophageal eosinophils per HPF and total score from EDP (A), HSS (B), and EREFS (C). EDP=eosinophilic esophagitis diagnostic panel. EREFS=eosinophilic esophagitis endoscopic reference score. HPF=high-power field. HSS=eosinophilic esophagitis histology scoring system.

The present invention is based, in part, on the discovery of three distinct EoE endotypes, EoEe1, EoEe2, and EoEe3, which can be determined based on their differential gene expression patterns, as described infra. Each of the EoE endotypes described here has a pattern of gene expression as well as distinct histological, endoscopic, and clinical features. The disclosure provides methods for stratifying EoE patients into one of these endotypes and personalizing patient therapy based on same. In this context, the term 'stratify' and 'classify' are used interchangeably to refer to the grouping of EoE patients into one of at least three distinct EoE endotypes using the methods described here. An "endotype" refers to an EoE disease subtype defined by distinct molecular and cellular markers relevant to disease pathology. Each of the at least three EoE endotypes provided by the present disclosure is described in more detail in the following sections.

Generally, the histological features of each endotype are defined by a histological assessment, particularly the eosinophilic esophagitis histology scoring system (HSS), which takes into account disease stage and grade across eight different variables beyond peak eosinophil levels. See e.g., Collins et al. Newly developed and validated eosinophilic esophagitis histology scoring system and evidence that it outperforms peak eosinophil count for disease diagnosis and monitoring. *Dis Esophagus* 2017; 30: 1-8. The HSS assesses eight histological features: eosinophilic inflammation, basal zone hyperplasia, eosinophilic abscess, eosinophilic surface layering, dilated intercellular spaces, surface epithelial alteration, dyskeratotic epithelial cells, and lamina propria fibers. Each feature is scored on a 4-point scale for severity (grade) or extent (stage) of the abnormality, with 0 representing normal features and 3 denoting most severe or extensive features. A final HSS score (grade or stage) is the sum of the assigned scores for each feature assessed divided by the maximum possible score for that biopsy specimen.

As discussed in more detail below, two HSS features, basal zone hyperplasia (BZH) and surface epithelial alteration (SEA), demonstrated significant association with the EoE endotypes described here. BZH was significantly higher in EoEe2 compared to EoEe1, and SEA was significantly higher in EoEe3 compared to EoEe1.

The endoscopic features of each endotype are defined by the eosinophilic esophagitis endoscopic reference score (EREFS). The EREFS takes into account five endoscopic features, edema, concentric rings, white plaques or exudates, longitudinal furrows, and strictures, and has relevance in terms of understanding the clinical features and monitoring the effect of treatment in both children and adults.

As discussed in more detail below, the EREFS features of edema, exudates, and furrows showed significant association with the EoE endotypes described herein. Edema was higher in both EoEe2 and EoEe3 compared to EoEe1. The occurrence of exudates was significantly higher in EoEe2 compared to EoEe1, and the occurrence of furrows was significantly higher in EoEe3 compared to EoEe1.

Each endotype described here is also associated with specific clinical characteristics and phenotypes. For example, EoEe1 is strongly associated with normal appearing esophagus and the clinical phenotypes designated atopic, pediatric-onset, steroid sensitive, and normal endoscopic appearance. For this reason, the EoEe1 endotype may also be referred to herein as the 'mild' endotype.

EoEe2 is strongly associated with steroid refractory disease and the clinical phenotypes designated inflammatory and steroid-refractory. For this reason, the EoEe2 endotype may also be referred to herein as the 'intermediate', 'inflammatory' or 'steroid-refractory' endotype.

EoEe3 is strongly associated with the presence of narrow-caliber esophagus and the clinical phenotypes designated non-atopic, adult onset, and fibrostenotic. In the context of the present disclosure, the endotypes may also be referred to with reference to their associated clinical phenotypes. For this reason, the EoEe3 endotype may also be referred to herein as the 'severe' endotype.

In accordance with the methods described here, a patient's EoE disease is determined to be of a mild, intermediate, or severe EoE endotype. The methods comprise determining the gene expression of one or more genes, or the gene expression profile of a panel of genes, whose expression is associated with a mild, intermediate, or severe endotype. The disclosure further provides for the targeted treatment of a patient based on EoE endotype. In accordance with the methods described here, the patient may be treated with one or more EoE therapies, including, for example, proton pump inhibitor therapy, dietary therapy, anti-cytokine therapy, anti-ALOX15 therapy, anti-TSLP therapy, glucocorticoid therapy, and esophageal dilation. In the context of the present disclosure, the terms "treatment", "treating", or "treat" describe the management and care of a patient for the purpose of combating EoE and may include the administration of a therapeutic agent as well as the administration of a therapy such as a restricted diet, including for example elemental and elimination diets, or a medical procedure such as esophageal dilation, to alleviate one or more symptoms or complications of EoE, or to eliminate one or more symptoms or complications of EoE, thereby treating the EoE. Therapeutic agents may include small molecules, such as proton pump inhibitors and glucocorticoids, or biologic agents, such as therapeutic antibodies or nucleic acids, including interfering RNAs.

Proton pump inhibitor (PPI) therapy may include treatment with a PPI such as dexlansoprazole, esomeprazole, lansoprazole, omeprazole, pantoprazole, and rebeprazole.

Dietary therapy may include, for example, elemental and elimination diets.

Anti-cytokine therapy may include, for example, a biologic agent targeted to inhibit cytokine signaling by one or more cytokines via their cognate receptors. In embodiments, the anti-cytokine therapy is an anti-T helper type 2 (Th2) therapy. A Th2 immune response is generally characterized by the production of interleukin-4 (IL-4), interleukin-5 (IL-5), and interleukin-13 (IL-13). Accordingly, an anti-Th2 therapy encompasses a therapy targeting one or more of IL-4, IL-5, and IL-13, and/or their receptors in order to inhibit IL-4, IL-5, and/or IL-13 mediated signal transduction. The most common biologics for anti-cytokine therapy are antibodies, preferably monoclonal antibodies, and most preferably fully human or humanized monoclonal antibodies. In embodiments of the methods described here, the anti-cytokine therapy is an anti-T helper type 2 (Th2) therapy selected from one or more of a therapy targeting the IL-4 and/or IL-13 signaling pathway, and a therapy targeting the IL-5 signaling pathway.

Interleukin-4 and interleukin-13 both mediate inflammation through their receptors, with IL-13 also binding to type 2 IL-4 receptors. IL-4 and IL-13 signaling pathways thus overlap and therapies envisioned by the methods described here may target one or both of these signaling pathways. Therapies targeting IL-4 signaling include monoclonal antibodies such as dupilumab, which targets the IL-4 receptor alpha (IL-4Ra). Therapies targeting IL-13 signaling include monoclonal antibodies such as RPC4046 or tralokinumab, both of which target IL-13.

Interleukin-5 (IL-5, CD125) is an eosinophil growth, activation, and survival factor. Humanized anti-IL-5 antibodies have been shown to be effective in treating asthma patients with the severe eosinophilic form of the disease, as discussed in Rothenberg M E. Humanized Anti-IL-5 Antibody Therapy. Cell 2016; 165(3): 509. Therapies targeting the IL-5 signaling pathway include, for example, therapies targeting IL-5 and its receptor, also known as CD125. Such therapies include monoclonal antibodies such as mepolizumab and reslizumab, which target IL-5, and monoclonal antibodies such as benralizumab, which target the IL-5 receptor.

Anti-ALOX15 therapy is therapy directed at suppressing the expression or activity of the ALOX15 gene product, arachidonate 15-lipoxygenase. Examples of ALOX15 inhibitors include PD146176.

Anti-TSLP therapy or anti-ALOX15 therapy may also comprise the administration of a single or double stranded ribonucleic acid (RNA) agent that inhibits the expression of the TSLP gene or the ALOX15 gene, for example, by catalyzing the post-transcriptional cleavage of the target mRNA, or by inhibiting transcription or translation of the target mRNA. In embodiments, the RNA agent is a double stranded or single stranded RNA interference-based agent (RNAi). The RNAi agent may be based on a microRNA (miRNA), a short hairpin RNA (shRNA), or a small interfering RNA (siRNA). The RNAi agent comprises a region that is at least partially, and in some embodiments fully, complementary to the target RNA. Although perfect complementarity is not required, the correspondence should be sufficient to enable the RNAi agent, or its cleavage product in the case of double stranded siRNA or RNAi agents comprising cleavable linkers, to direct sequence specific silencing of the target mRNA, e.g., by RNAi-directed cleavage of the target mRNA.

Glucocorticoid therapy may comprise, for example, therapy with one or more glucocorticoids selected from fluticasone, prednisone and budesonide.

Previous work has suggested that EoE progresses from a chronic inflammatory phenotype, which may manifest on endoscopy with white exudates, edema, and linear furrows, to fibrostenosis, which is characterized by esophageal rings, strictures, and/or narrowing. Accordingly, the disclosure also provides methods for monitoring the progression of EoE in a patient diagnosed with EoE, and methods for monitoring the efficacy of therapy for an EoE patient. These methods may additional temporal assaying steps in order to monitor the changes in a patient's gene expression profile before and during the course of therapy, in order to determine the progression of the patient's EoE, for example from a mild endotype to an intermediate or severe endotype, and/or to monitor the effectiveness of the therapy in delaying the onset of a more serious endotype or ameliorating one or more symptoms of the patient's disease, including reverting to a less serious endotype.

Classification of patients into one of the EoE endotypes described here can also be used to stratify clinical trial participants, either prospectively or retrospectively, to identify subgroups with distinct responsiveness to therapy. Accordingly, the disclosure also provides methods for the stratification of clinical trial participants to identify participants whose disease can be characterized according to an EoE endotype as described here.

The present disclosure provides three defined EoE endotypes, which are described in more detail below, along with exemplary EoE therapies targeted to each. The disclosure also provides methods for differentiating among these three endotypes based on the expression of one or more genes or a panel genes. In embodiments, the one or more genes or panel of genes comprises one or more genes selected from the group consisting of ACTG2, ALOX15, ANO1, APOBEC3A, CCR3, CDA, CRISP3, CRYM, DSG1, FFAR3, IL4, PNLIPRP3, RGS9BP, TNFAIP6, TSLP, UPK1A, and WDR36. In embodiments, the expression of a panel of genes is assayed. In embodiments, the panel comprises or consists of two or more, or all eight, of the following genes: ANO1, CRYM, DSG1, PNLIPRP3, TNFAIP6, TSLP, UPK1A, and WDR36, which were determined by machine learning assisted methods to be sufficient for discriminating between the three endotypes, as described in more detail below. In embodiments, the panel comprises or consists of one or more of the genes disclosed in Table 2. In embodiments, the panel of genes assayed comprises or consists of one or more, or all, of ALOX15, APOBEC3A, CDA, CRISP3, ACTG2, CCR3, FFAR3, IL4, RGS9BP, TSLP; and PNLIPRP3; or ALOX15, APOBEC3A, CDA, CRISP3, ACTG2, CCR3, FFAR3, IL4, RGS9BP, TSLP, CTNNAL1, EML1, FLG, PNLIPRP3 and TSPAN12, each of which is differentially expressed among the three endotypes described here, as detailed in Table 2.

In accordance with the methods for determining a patient's EoE endotype described here, the methods may comprise determining the gene expression profile for a panel of genes selected comprising one or all of the genes in the following panels:

Panel 1: ANO1, CRYM, DSG1, PNLIPRP3, TNFAIP6, TSLP, UPK1A, and WDR36;
Panel 2: ALOX15, APOBEC3A, CDA, and CRISP3;
Panel 3: ACTG2, CCR3, FFAR3, IL4, RGS9BP, and TSLP; and
Panel 4: CTNNAL1, EML1, FLG, PNLIPRP3, and TSPAN12.

In this context, a gene expression profile represents the expression of multiple genes and may include genes whose expression is increased or decreased relative to a reference, for example as set forth in Table 2.

The disclosure provides methods of determining a patient's EoE endotype, the methods comprising assaying the expression of at least one gene or panel of genes selected from the genes set forth in Table 2.

In embodiments, the at least one gene or panel of genes is selected from the group consisting of ACTG2, ALOX15, ANO1, APOBEC3A, CCR3, CDA, CRISP3, CRYM, DSG1, FFAR3, IL4, PNLIPRP3, RGS9BP, TNFAIP6, TSLP, UPK1A, and WDR36. In embodiments, the at least one gene or panel of genes is selected from the group consisting of ALOX15, APOBEC3A, CDA, and CRISP3, wherein the expression of one or both of ALOX15 and APOBEC3A is decreased more than 2-fold and the expression of one or both of CDA and CRISP3 is increased more than 2-fold, compared to a reference, and the subject's EoE endotype is determined to be mild. In embodiments, the methods may also comprise assaying the expression of one or more of ALOX12, COL8A2, ENDOU, EPB41L3, GCNT3, HILPDA, IGFL1, PLAUR, SPINK7, UPK1A, and ZNF365. In embodiments, a subject determined to have a mild EoE endotype is treated with an EoE therapy targeted to the endotype, for example the subject is administered a therapy comprising one or both of proton pump inhibitor (PPI) therapy and dietary therapy.

In embodiments, the at least one gene or panel of genes is selected from the group consisting of ACTG2, CCR3, FFAR3, IL4, RGS9BP, and TSLP. In embodiments, the expression of one or more of ACTG2, CCR3, FFAR3, IL4, RGS9BP, and TSLP is increased more than 2-fold, more than 5-fold, or more than 10-fold, compared to a reference, and the subject's EoE endotype is determined to be intermediate. In embodiments, a subject determined to have an intermediate EoE endotype is treated with an EoE therapy targeted to the endotype, for example the subject is administered a therapy comprising one or more of anti-cytokine therapy, anti-TSLP therapy, and anti-ALOX15 therapy. In embodiments, a subject whose EoE endotype is determined to be intermediate as described herein is not administered glucocorticoid therapy.

In embodiments, the at least one gene or panel of genes is selected from the group consisting of ACPP, CITED2, CTNNAL1, EML1, FLG, GRPEL2, MT1M, PNLIPRP3, and TSPAN12. In embodiments, the expression of one or more of CTNNAL1, EML1, FLG, PNLIPRP3, and TSPAN12 is decreased at least 2-fold, at least 5-fold, or at least 10-fold, compared to a reference, and the subject's EoE endotype is determined to be severe. In embodiments, a subject determined to have a severe EoE endotype is treated with an EoE therapy targeted to the endotype, for example the subject is administered a therapy comprising one or more of anti-ALOX15 therapy, esophageal dilation, anti-cytokine therapy, and glucocorticoid therapy.

The methods of the present disclosure are preferably applicable to human subjects, also referred to as "patients", but the methods may also be applied to other mammalian subjects. Accordingly, in embodiments a method described here may be performed on a "subject" which may include any mammal, for example a human, primate, mouse, rat, dog, cat, cow, horse, goat, camel, sheep or a pig. Preferably, the subject is a human. The term "patient" refers to a human subject.

In accordance with the methods described here, in some embodiments, a subject "in need of" treatment may be a subject who has already been diagnosed with EoE. In other embodiments, the subject "in need of" treatment may be one who is suffering from one or more symptoms such as difficulty swallowing, impaction of food in the esophagus, chest pain, heartburn, or upper abdominal pain.

The term "biological sample" as used herein may refer to a sample, including a biopsy sample, of a tissue, or other biological sample such as an exudate, saliva, serum, plasma, mucus, blood, or urine sample; or a swab such as an oral or a buccal swab. In some embodiments, the sample is a tissue sample, for example an esophageal tissue sample obtained at biopsy.

Endotype 1 "Mild or EoEe1"

The EoEe1 endotype is generally characterized by relatively small changes in epithelial differentiation genes, a pauci-inflammatory state, and a greater proportion of normal-appearing esophagus by endoscopy. Other clinical features associated with EoEe1 include pediatric onset, atopic, and steroid sensitivity.

EoEe1 is also characterized by markedly low expression of the ALOX15 gene. ALOX15 may also be referred to as arachidonate 15-lipoxygenase or 15-lipoxygenase-1. Other genes differentially expressed in EoEe1 include APOBEC3A, which is also underexpressed in EoEe1 compared to either EoEe2 or EoEe3; CDA, and CRISP3, each of which is overexpressed in EoEe1. Additional genes that are differentially expressed in EoEe1 include ALOX12, COL8A2, ENDOU, EPB41L3, GCNT3, HILPDA, IGFL1, PLAUR, SPINK7, UPK1A, and ZNF365.

The disclosure provides methods for treating EoE patients whose disease endotype is determined to be mild, or EoEe1. The methods comprise one or both of proton pump inhibitor (PPI) therapy and dietary therapy, which may include for example elemental and elimination diets. Suitable proton pump inhibitors for use in PPI therapy are described above.

Endotype 2 "Intermediate or EoEe2"

The EoEe2 endotype is generally characterized by particularly high type-2 immune response mechanisms and a steroid-refractory phenotype. Other clinical features associated with EoEe2 include pediatric onset.

EoEe2 is also characterized by high expression of the interleukin-4 (IL-4), thymic stromal lymphopoietin (TSLP), and the actin gamma smooth muscle 2 (ACTG2) genes. Other genes differentially expressed in EoEe2 include CCR3, FFAR3, and RGS9BP, each of which is overexpressed in EoEe2 relative to either EoEe2 or EoEe3. Additional genes that are differentially expressed in EoEe2 include CLEC16A, FKBP5, HPGDS, IL5RA, KRT23, LRRC32, MUC4, NTRK1, PTGFRN, RUNX2, SAMSN1, TGFB1, UPK1B and WDR36.

The disclosure provides methods for treating EoE patients whose disease endotype is determined to be intermediate, or EoEe2. The methods comprise anti-cytokine therapy, including anti-Th2 immune therapies, such as therapies targeting the IL-4 and/or IL-13 signaling pathway, and therapies targeting the IL-5 signaling pathway. In embodiments, the anti-cytokine therapy is an anti-Th2 therapy. In embodiments, the anti-Th2 therapy is a monoclonal antibody targeted against one or more of IL-4, IL-13, and IL-5, or their receptors. In embodiments, the therapy is a monoclonal antibody targeted against IL-5 or its receptor. In embodiments, the monoclonal antibody targeted against IL-5 or its receptor is selected from mepolizumab, reslizumab, and benralizumab. In embodiments, the therapy is a monoclonal antibody targeted against IL-4 or its receptor. In embodiments, the monoclonal antibody targeted against IL-4 or its receptor is dupilumab. In embodiments, the therapy is a monoclonal antibody targeted against IL-13 or its receptor. In embodiments, the monoclonal antibody targeted against IL-13 or its receptor is RPC4046 or tralokinumab.

The methods may also comprise anti-TSLP therapy, such as monoclonal antibodies against TSLP including tezepelumab (MEDI9929, AMG 157), and therapies targeted to suppress ALOX15.

Endotype 3 "Severe or EoEe3"

The EoEe3 endotype is generally characterized by low expression of epithelial differentiation genes and a greater frequency of narrow-caliber esophagus. Other clinical features associated with EoEe3 include adult onset, non-atopic, and fibrostenotic.

EoEe3 is also characterized by low expression of the EML1, PNLIPPR3, and TSPAN12 genes. Other genes differentially expressed in EoEe3 include ACPP, CITED2, CTNNALI, FLG, GRPEL2, and MT1M.

The disclosure provides methods for treating EoE patients whose disease endotype is determined to be severe, or EoEe3. The methods comprise therapies targeted to suppress ALOX15, esophageal dilation, anti-cytokine therapy, for example anti-IL-13 and anti-IL-4 receptor alpha (IL-4Ra) therapies including monoclonal antibodies, for example RPC4046 (anti-IL-13) and dupilumab (anti-IL4Ra), and glucocorticoid therapy, for example therapy with fluticasone, prednisone or budesonide.

Methods of Measuring Gene Expression

In accordance with the methods described here, the expression of one or more genes, or of a panel of genes, is determined in a biological sample, such as an esophageal biopsy sample, obtained from a patient in need of treatment as described herein.

Gene expression may be determined, for example, using a method for detecting and quantitating mRNA expression. Such methods include PCR-based methods such as reverse transcription followed by a polymerase chain reaction (PCR), including a quantitative PCR (qPCR) reaction. The steps may comprise generating a single stranded complementary DNA (cDNA) template from mRNA of the biological sample, e.g., through the performance of a reverse transcription (RT) reaction. Additional steps may include amplification of the cDNA and performance of a method for determining the amount of amplified DNA, for example through the use of labeled probes or DNA intercalating dyes. Additional methods include quantitative PCR performed with a low density array or high density microarray based technique. In embodiments, the methods described here may further comprise one or more steps of converting mRNA to cDNA, converting cDNA to labelled cRNA, e.g., biotinylated cRNA, and hybridizing the labelled cRNA to an oligonucleotide-based DNA microarray chip.

The term "microarray" refers to arrays of probe molecules that can be used to detect analyte molecules, e.g., oligonucleotide probe arrays to measure gene expression. The terms "array," "slide," and "chip" may be used interchangeably to refer to oligonucleotide probe arrays. Such arrays may comprise oligonucleotide probes that are synthesized in silico on the array substrate, sometimes referred to as 'high density' arrays, or the arrays may be spotted arrays, which tend to have lower densities.

The term "gene expression" refers to the transcription of DNA sequences into RNA molecules. The expression level of a given gene measured at the nucleotide level refers to the amount of RNA transcribed from the gene measured on a relevant or absolute quantitative scale. The measurement can be, for example, an optic density value of a fluorescent signal on a microarray image. Differential expression means that the expression levels of certain genes, as measured at the nucleotide level, are different in different states, tissues, or type of cells, relative to the amount or level of gene expression of a reference gene. In the context of the methods described here, certain genes are differentially expressed in different EoE disease endotypes, for example as set forth in Table 2. The terms 'level' and 'amount' when used in the context of gene expression are used interchangeably to refer to the amount of gene transcripts in a cell or tissue sample. Where the amount is a relative amount, it is relative to the expression of a reference gene or the expression of a reference set of genes, or the amount of one or more reference oligonucleotides which are exogenously added to a sample. In some embodiments, the reference is an endogenous gene, an exogenously added reference oligonucleotide including an artificial RNA or DNA, a reference gene index, or a target gene index. A reference gene index may be comprised of multiple averaged endogenous control genes such as multiple housekeeping genes. A target gene index may be comprised of multiple averaged genes of interest, such as multiple genes described herein as differentially expressed in an EoE endotype. In some embodiments, more than one reference may be used, for example multiple exogenous control oligonucleotides and multiple endogenous housekeeping genes may be used in the same assay. In embodiments, the reference may be a computed average expression value for one or more genes expressed in a target endotype relative to the expression of the one or more genes in each of the other endotypes, for example EoEe1 relative to EoEe2 and/or EoEe3.

For qPCR based methods, the gene expression may be presented as a delta cycle threshold (Ct) value. The Ct value is defined as the number of PCR cycles required for the fluorescent signal of an amplified product to exceed a background or threshold level. The Ct value is therefore inversely proportional to the amount of the target nucleic acid in the sample. The delta Ct value represents the difference in expression between a target gene and a reference gene calculated as a difference in the Ct values of the target and reference genes in the sample.

In some embodiments, gene expression may further be compared to a second relative parameter such as a non-treated control, a time point (e.g., time zero), or healthy cells, tissues or subjects. Generally, normal healthy esophageal tissue is defined histologically as having zero eosinophils per high power field and no basal layer expansion.

In embodiments, the methods described here may further comprise one or more additional steps of extracting RNA from a biological sample obtained from the patient, for example, an esophageal biopsy sample. The steps may include isolating total RNA and/or mRNA from the biological sample, converting mRNA to cDNA, and performing a PCR-based amplification step. mRNA may be isolated from total RNA, for example using a commercially available kit, such as the RNeasy™ Mini kit (Qiagen), followed by enriching for mRNA using a suitable method, such as oligo(dT) magnetic beads. The mRNA may also be fragmented into short fragments of about 200 base pairs (bp) using a suitable fragmentation buffer. cDNA may be produced from the mRNA, for example, using the fragmented mRNA as a template with random hexamer primers for first-strand cDNA synthesis followed by second-strand cDNA synthesis and purification of the short double-stranded cDNA fragments using standard protocols or a commercially available kit, for example a QIAquick™ PCR purification kit (Qiagen).

Methods of Assigning Subjects to Endotypes

The present disclosure provide methods for assigning a subject to an EoE endotype for treating EoE in the subject. The methods comprise determining the subject's EoE endotype based on the expression of one or more genes or a panel of genes in a biological sample from the subject, and may optionally further comprise determining the expression of the one or more genes or a panel of genes, for example using a method as described above.

The methods for determining a subject's endotype are based on a linear discriminant analysis of the expression of the one or more genes or panel of genes in the biological sample from the subject. In embodiments, the analysis comprises or consists of one or more of ANO1, CRYM, DSG1, PNLIPRP3, TNFAIP6, TSLP, UPK1A, and WDR36; or a panel comprising or consisting of the foregoing genes. In this analysis, group membership, i.e., endotype, is predicted by the continuous variables, i.e., gene expression, which may also be referred to as covariates.

The methods generally relate to analyzing gene expression data taking into account the multidimensional structure of the data. The endotypes identified by the present disclosure are represented such that an input vector comprising the expression of the one or more genes or panel of genes can be assigned to an endotype based on the calculation of a similarity metric between the input vector and each of endotypes defined herein. This analysis determines which endotype is the nearest to, or most similar to, the input vector. In accordance with the present disclosure, the methods comprise utilizing a probability distance metric, e.g., the Mahalanobis distance, and calculating a probability distance between an input vector and the endotypes.

EXAMPLES

The following describes the identification and characterization of three EoE endotypes for use in the treatment of EoE. As discussed in more detail below, each of the three endotypes has characteristic histological and endoscopic features and is associated with distinct clinical characteristics and phenotypes. In addition, we provide eight genes with strong discriminatory power for assignment into one of the three endotypes, which may be used in clinical practice.

Gene expression profiles from a total of 285 esophageal biopsy samples were analyzed, including the discovery cohort of 185 individual subjects from 10 clinical sites and the validation cohort of 100 individual subjects from a single site (Cincinnati cohort) Basic demographic characteristics are detailed in Table 1.

TABLE 1

Basic characteristics of subjects in the discovery and validation cohorts

|  | Discovery Cohort (n = 185) | Validation Cohort (n = 100) |
| --- | --- | --- |
| Demographics |  |  |
| Age at biopsy (years) | 18.3 (8.8-37.1) | 10.2 (6.3-15.2) |
| Sex |  |  |
| Male | 125 (68%) | 80 (80%) |
| Female | 60 (32%) | 20 (20%) |
| Ethnic origin |  |  |
| White | 170 (92%) | 95 (95%) |
| Other | 15 (8%) | 5 (5%) |
| History of eosinophil gastrointestinal disease |  |  |
| Eosinophil esophagitis | 185 (100%) | 100 (100%) |
| Eosinophil gastritis | 4 (2%) | 6 (6%) |
| Eosinophil colitis | 4 (2%) | 0 (0%) |
| Treatment at biopsy |  |  |
| Current PPI treatment | 62 (34%) | 84 (84%) |
| Current topical steroid treatment | 95 (51%) | 58 (58%) |
| Ongoing diet therapy | 97 (52%) | 63 (63%) |
| Disease variables at biopsy |  |  |
| Peak eosinophil count (per HPF) | 15 (1-46) | 69 (34-144) |
| EDP total score | 242 (67-352) | 126 (67-249) |
| HSS total score | 0.5 (0.2-0.9) | 0.8 (0.5-1.0) |
| EREFS total score | 2.0 (0.0-6.0) | 1.0 (1.0-2.0)* |

Data are number (%) or median (IQR).
EDP = eosinophil esophagitis diagnostic panel.
EREFS = esophagitis endoscopic reference score.
ESS = endoscopic severity score.
HPF = high-power field.
HSS = eosinophil esophagitis histology scoring system.
PPI = proton-pump inhibitor.
*Simplified ESS used.

Of 185 subjects in the discovery cohort, the age range for all subjects was 3.5 to 69.6 years, with 88 children and 97 adults. The pediatric and adult groups both exhibited a male predominance. Although there were different proportions of pediatric-onset versus adult-onset EoE, the length of time from the initial EoE diagnosis to the biopsy sample collection were similar in pediatric and adult individuals. Peak eosinophil counts ranged from 0 to 174 eosinophils/HPF. Approximately half of the subjects (46.5%, n=86) had active EoE (≥15 eosinophils/HPF) and 20.5% of subjects (n=38) had biopsy specimens without eosinophils. There were no significant differences in peak eosinophil counts between pediatric and adult individuals with active EoE; however, some clinical and endoscopic findings differed by age. Among subjects with active EoE, a larger proportion of pediatric subjects with EoE had an inflammatory phenotype at endoscopy than did adults with EoE (p=0.0008), and significantly more adults had a fibrostenotic phenotype than did pediatric individuals (p<0.0001). There was no significant difference in the EDP score nor HSS score between pediatric and adult individuals with active EoE, whereas the EREFS total score was significantly higher in adults than children (p<0.0001). The distribution of the different types of therapy were similar between the pediatric and adult populations. Among the subjects with a history of swallowed steroid treatment (n=91), there were fewer subjects in the category of steroid-refractory (n=25/91, 27.5%) than steroid-sensitive (n=66/91, 72.5%), and this distribution was similar in pediatric and adult individuals (p=0.82).

Figure 1B:
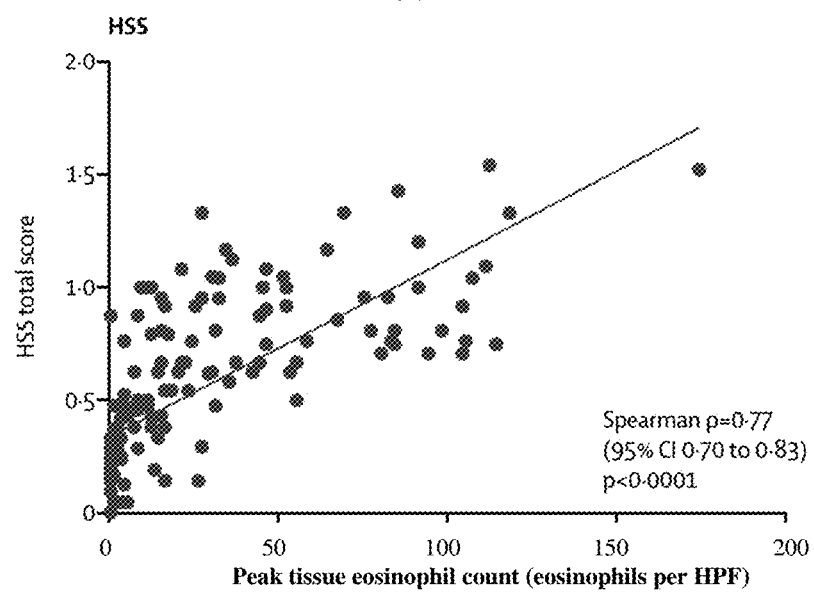
Figure 1C:
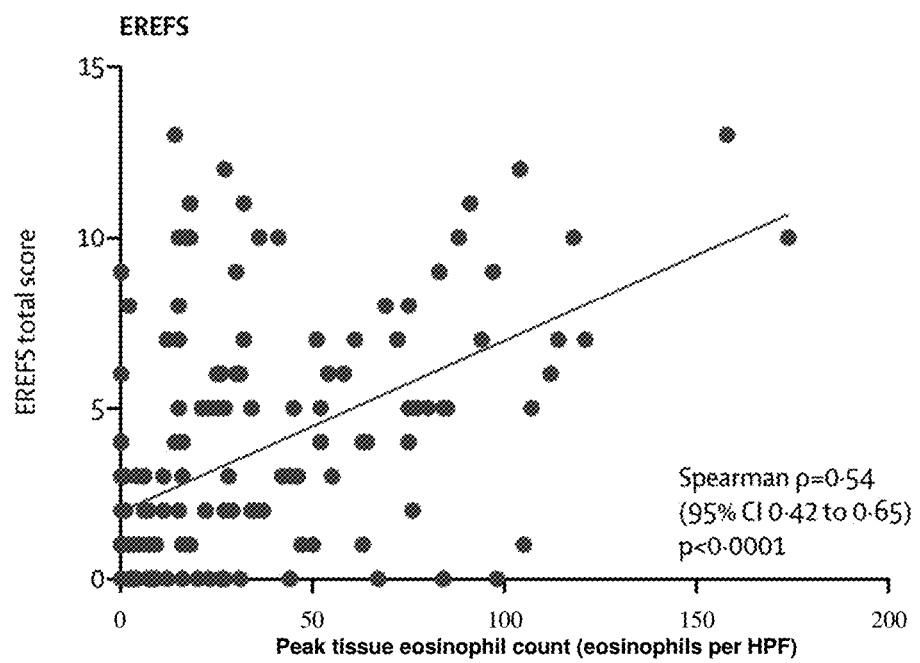

The EoE Diagnostic Panel (EDP) showed consistency across sites (Spearman $\rho=-0.73--0.80$, $p<0.0001$) and had similar values across pediatric and adult subjects with EoE ($p=0.11$) (appendix p 20). To define the relationship among various clinical, endoscopic, and histologic features in relation to the accepted gold standard of assessing disease activity, the esophageal eosinophil level, we evaluated the associations between peak eosinophil counts and disease parameters (EDP, HSS, and EREFS). Using total scores, which represent the overall values of each platform, we found significant correlations between peak eosinophil counts and each platform (FIG. 1A EoE EDP score: Spearman $\rho=-0.74$, $p=1.9$ E–22; FIG. 1B HSS score: Spearman $\rho=0-81$, $p=1.8E-30$; and FIG. 1C EREFS score: Spearman $\rho=0.51$ $p=5.4E-13$, respectively).

Figure 2A:
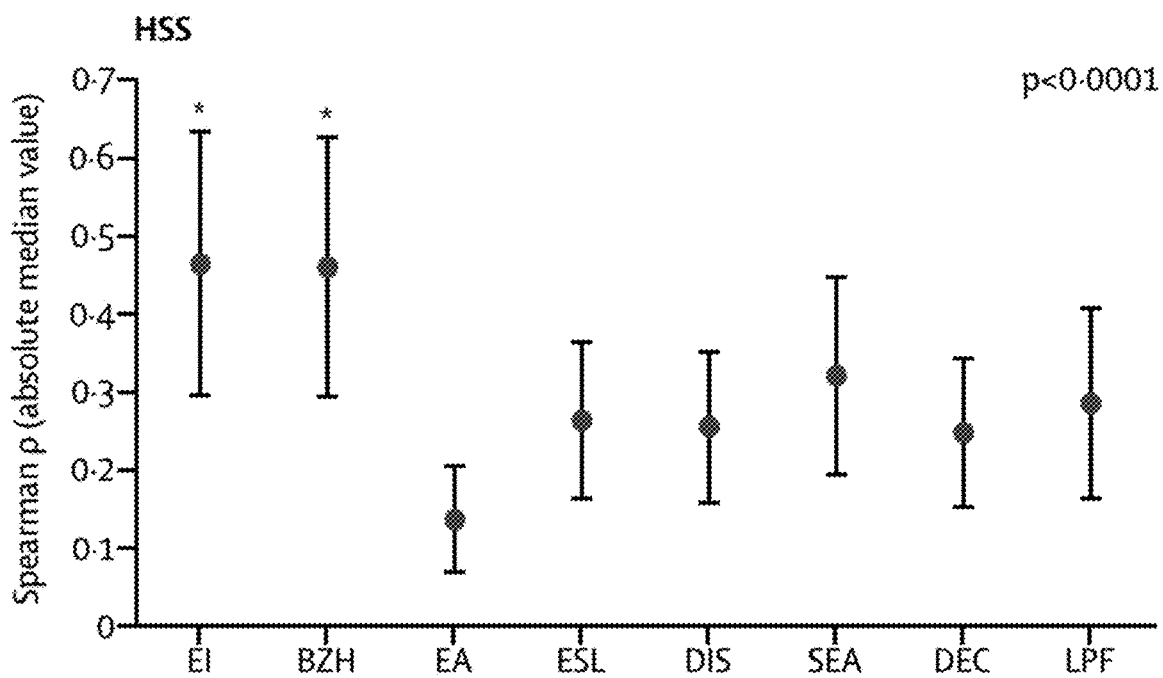
FIG. 2A-B: Associations between the EDP and HSS domains and EREFS features Spearman correlation analysis between gene expression levels on EDP and HSS domains (A) and EREFS features (B), using the absolute value to account for differences in the direction of the effect across genes. p values calculated with the Kruskal-Wallis test and Dunn's post-hoc test. Datapoints represent the absolute median and error bars the IQR. BZH=basal zone hyperplasia. DEC=dyskeratotic epithelial cells. DIS=dilated intercellular spaces. EA=eosinophilic abscess. EDP=eosinophilic esophagitis diagnostic panel. EI=eosinophilic inflammation. EREFS=eosinophilic esophagitis endoscopic reference score. ESL=eosinophilic surface layering. HSS=eosinophilic esophagitis histology scoring system. LPF=lamina propria fibres. SEA=surface epithelial alteration. *Dunn's post-hoc test, p<0.0001 vs EA, ESL, DEC, DIS, SEA, and LPF. †Dunn's post-hoc test, p=0.0324 vs oedema, p=0.0034 vs exudates, and p<0.0001 vs rings and stricture.
Figure 2B:
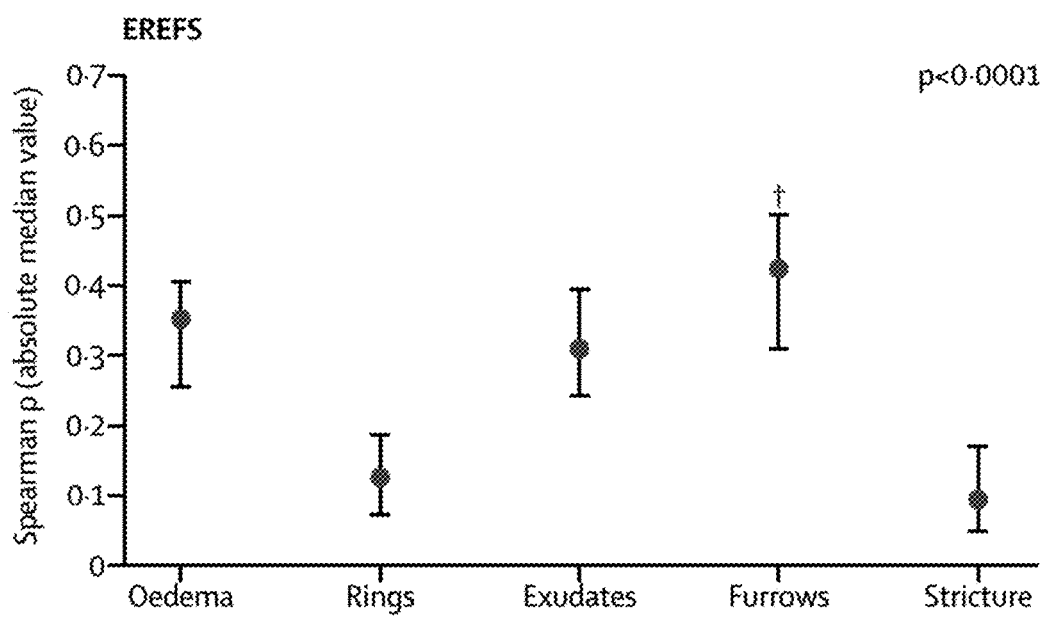

We subsequently focused on individual components of HSS and EREFS and their relationship with overall EDP. There were relatively strong associations between the EDP's 95 genes and several HSS domains (absolute median Spearman $\rho=0.30$ [IQR, 0.20–0.40]) (FIG. 2A). In particular, the basal zone hyperplasia (BZH) domain from the distal esophagus exhibited the highest magnitude of correlation with the overall EDP (absolute median Spearman $\rho=0.47$ [IQR, 0.36–0.61]). There were moderate associations between several EREFS domains and the EDP's 95 genes (absolute median Spearman $\rho=0.25$; [IQR, 0.11–0.38]) (FIG. 2B). In particular, distal furrows as a single endoscopic feature exhibited the highest magnitude of correlation with overall EDP (absolute median Spearman $\rho=0.43$ [IQR: 0.32–0.50]). A clustering tree based on the Spearman correlations showed their hierarchic relationships, supporting that the HSS and EREFS features aligned with the biological features associated with EoE.

Figure 3A:
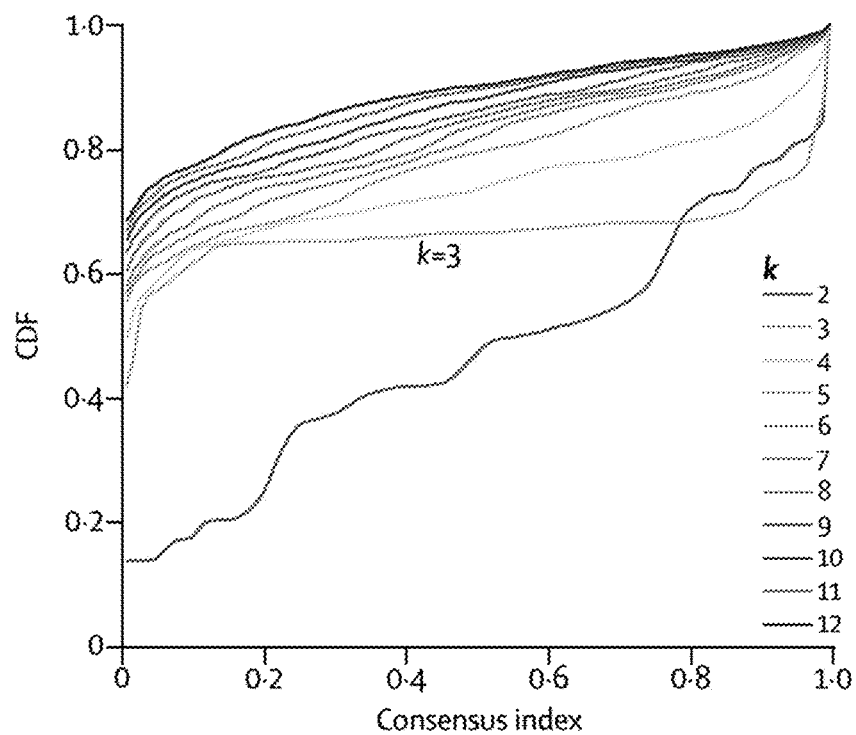
FIG. 3A-E: Clustering analysis of the active eosinophilic esophagitis group in the discovery cohort. (A) Consensus CDF with increasing number of clusters (k2 to k12). (B) Unsupervised consensus clustering of active eosinophilic esophagitis showed optimum partitioning to three clusters (endotypes). (C) Comparison of esophageal transcriptomes by endotype. Color range is based on log 2 normalized intensity value. (D) Three-dimensional plot containing sample points from the three endotypes, derived from principal component analysis of the entities shown in the heat map to visualize the geometric distance between any given samples. (E) Venn diagrams were generated based on 92 EDP transcripts that met criteria for differentially expressed genes. Venn diagrams compare the number of genes identified as differentially expressed genes (adjusted p<0.05 and two-fold change) that characterize the three endotypes. CDF=cumulative distribution function. EDP=eosinophilic esophagitis diagnostic panel. EoEe=eosinophilic esophagitis endotype.
Figure 3B:
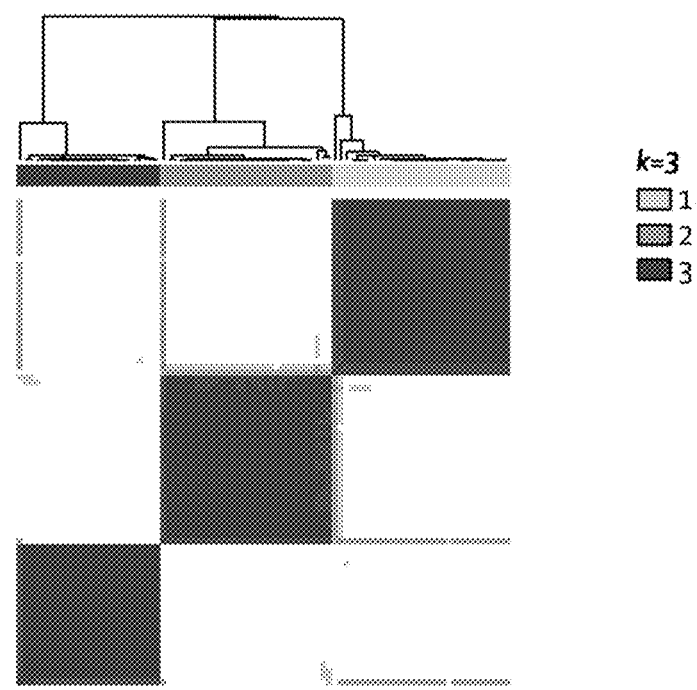
Figure 3C:
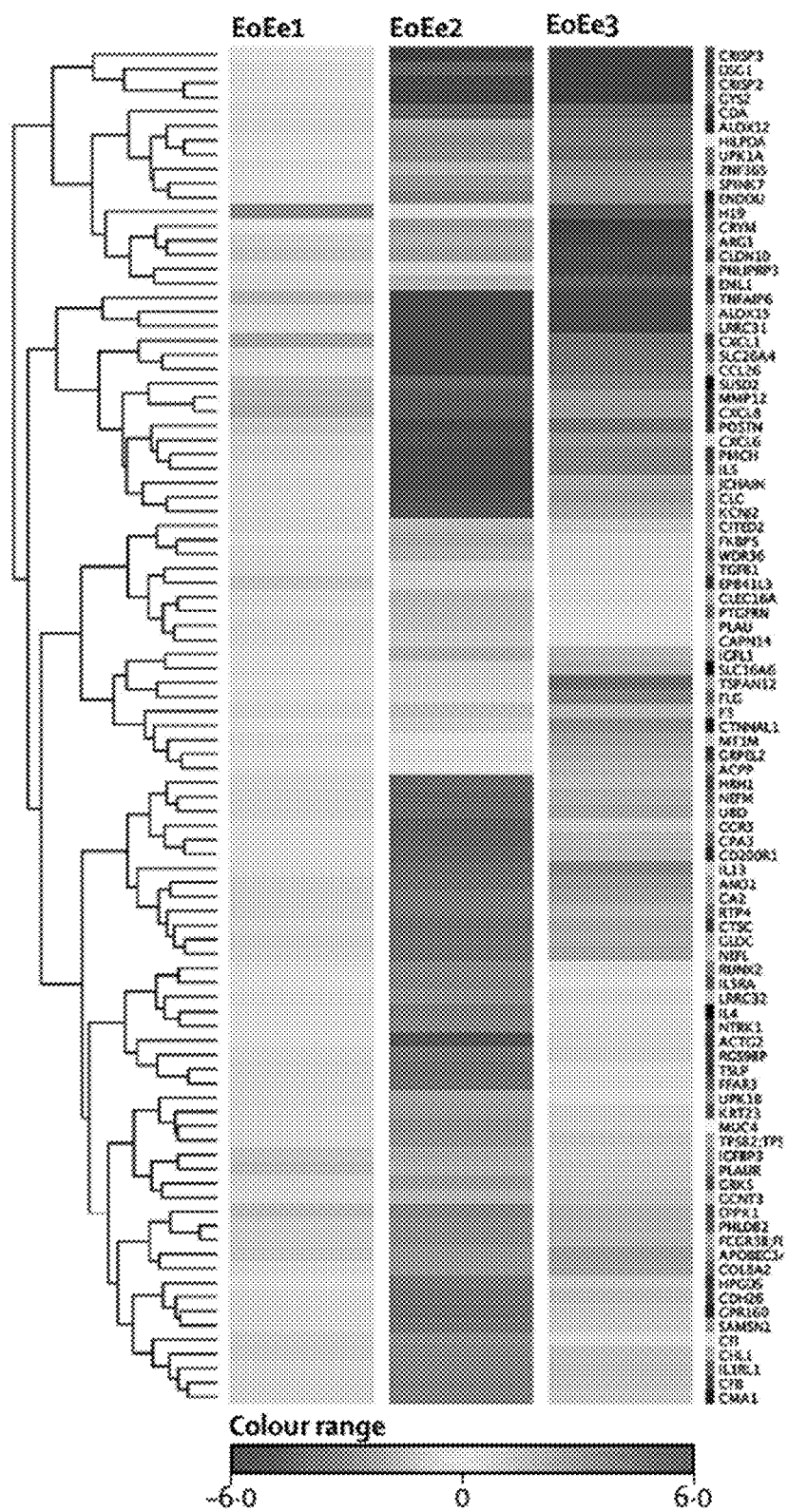
Figure 3D:
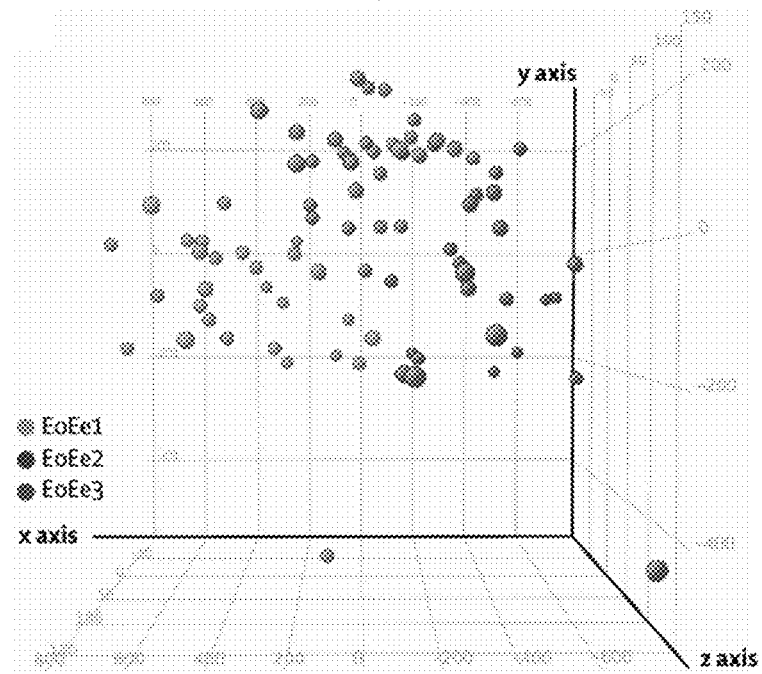
Figure 3E:
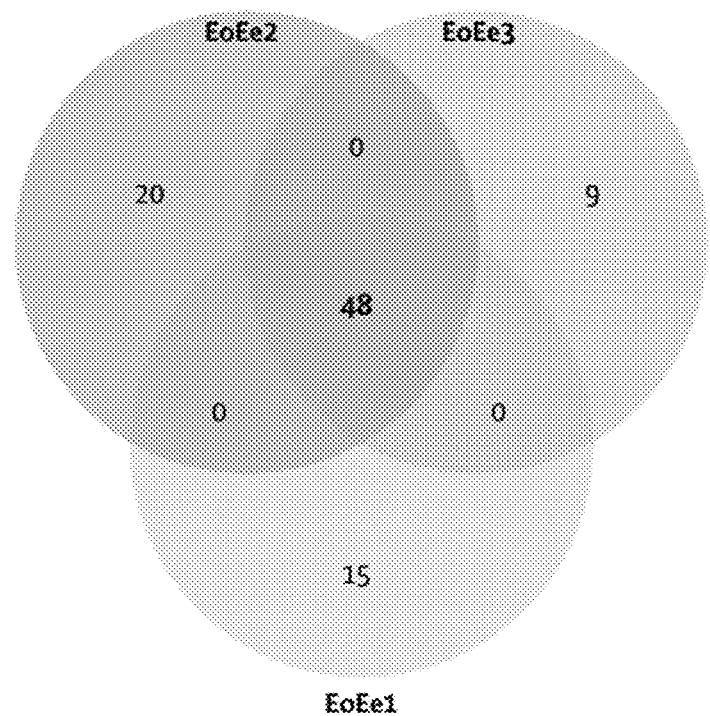

To test the hypothesis that active EoE demonstrates heterogeneous molecular profiling, we focused on analyzing subjects with active EoE (n=86). Consensus clustering based solely on the EDP was examined to assess stability for a number of potential cluster numbers varying from 2 to 12. This established 3 stable groups (i.e., endotypes, referred to as EoEe1-3) after resampling, as defined by a flat middle part of the consensus CDF (Figure A) and well-defined squares within the consensus matrix (FIG. 3B), in addition to the CLC values and silhouette widths. Although a few clinical sites enrolled a higher number of subjects, there was no significant difference in the distribution of the endotypes at any given site. On the heat map (FIG. 3C) and 3-dimensional plot by principal component analysis (PCA, FIG. 3D), these endotypes were well separated from each other. As a control, multiple biopsies obtained from the same endoscopy maintained each separate endotype (n=4, each endotype) (appendix p 24). Differentially expressed genes between each endotype were identified using a Benjamini-Hochberg false discovery rate of less than 0.05 and greater than 2-fold change. Using this threshold, there were a total of 15 differentially expressed genes in EoEe1, 20 in EoEe2, and 9 in EoEe3 (FIG. 3E). The differentially expressed genes between each endotype are detailed in Table 2 below.

TABLE 2

Differentially expressed genes between each endotype.

| | Fold change | | Adjusted |
| --- | --- | --- | --- |
| | Comparison 1 | Comparison 2 | p value |
| EoEe1 | EoEe1 vs EoEe2 | EoEe1 vs EoEe3 | ... |
| ALOX12 | 3.3 | 6.3 | $6.0 \times 10^{-6}$ |
| ALOX15 | −263.1 | −176.4 | $3.3 \times 10^{-11}$ |
| APOBEC3A | −11.0 | −8.3 | $6.8 \times 10^{-8}$ |
| CDA | 10.4 | 10.1 | $7.0 \times 10^{-9}$ |
| COL8A2 | −6.3 | −4.3 | $2.8 \times 10^{-4}$ |
| CRISP3 | 307.6 | 540.6 | $6.0 \times 10^{-11}$ |
| ENDOU | 6.1 | 5.6 | $1.0 \times 10^{-8}$ |
| EPB41L3 | −3.3 | −2.0 | $1.5 \times 10^{-2}$ |
| GCNT3 | −3.6 | −2.7 | $8.0 \times 10^{-7}$ |
| HILPDA | 5.3 | 7.5 | $3.9 \times 10^{-9}$ |
| IGFL1 | 2.9 | 2.7 | $1.4 \times 10^{-3}$ |
| PLAUR | −7.3 | −4.4 | $9.0 \times 10^{-7}$ |
| SPINK7 | 4.9 | 5.3 | $1.9 \times 10^{-5}$ |
| UPK1A | 5.4 | 9.1 | $4.3 \times 10^{-6}$ |
| ZNF365 | 2.8 | 5.5 | $3.5 \times 10^{-6}$ |
| EoEe2 | EoEe2 vs EoEe1 | EoEe2 vs EoEe3 | ... |
| ACTG2 | 28.9 | 44.2 | $2.0 \times 10^{-7}$ |
| CCR3 | 24.0 | 12.9 | $8.7 \times 10^{-11}$ |
| CLEC16A | 3.3 | 3.0 | $1.5 \times 10^{-7}$ |
| FFAR3 | 18.0 | 14.5 | $1.6 \times 10^{-6}$ |
| FKBP5 | 3.2 | 5.1 | $1.0 \times 10^{-5}$ |
| HPGDS | 9.1 | 6.1 | $1.8 \times 10^{-7}$ |
| IL4 | 9.9 | 10.8 | $1.0 \times 10^{-8}$ |
| IL5RA | 7.3 | 7.8 | $1.1 \times 10^{-6}$ |
| KRT23 | 5.4 | 3.1 | $1.2 \times 10^{-5}$ |
| LRRC32 | 7.1 | 9.2 | $1.4 \times 10^{-7}$ |
| MUC4 | 7.1 | 4.2 | $2.3 \times 10^{-8}$ |
| NTRK1 | 8.4 | 10.6 | $2.3 \times 10^{-8}$ |
| PTGFRN | 2.5 | 2.4 | $1.2 \times 10^{-7}$ |
| RGS9BP | 14.8 | 21.1 | $3.4 \times 10^{-6}$ |
| RUNX2 | 7.9 | 6.1 | $2.7 \times 10^{-8}$ |
| SAMSN1 | 13.4 | 7.2 | $1.0 \times 10^{-8}$ |
| TGFB1 | 2.5 | 2.2 | $2.3 \times 10^{-5}$ |
| TSLP | 20.8 | 14.6 | $1.6 \times 10^{-6}$ |
| UPK1B | 4.6 | 3.3 | $3.1 \times 10^{-4}$ |
| WDR36 | 3.2 | 4.1 | $8.1 \times 10^{-9}$ |
| EoEe3 | EoEe3 vs EoEe1 | EoEe3 vs EoEe2 | ... |
| ACPP | −2.8 | −3.1 | $9.2 \times 10^{-9}$ |
| CITED2 | −2.9 | −5.7 | $7.6 \times 10^{-8}$ |
| CTNNAL1 | −5.9 | −8.0 | $2.9 \times 10^{-10}$ |
| EML1 | −10.7 | −5.6 | $1.6 \times 10^{-6}$ |
| FLG | −6.4 | −5.5 | $1.3 \times 10^{-7}$ |
| GRPEL2 | −3.4 | −4.0 | $2.7 \times 10^{-9}$ |
| MT1M | −4.9 | −4.5 | $1.2 \times 10^{-5}$ |
| PNLIPRP3 | −21.8 | −12.8 | $2.4 \times 10^{-9}$ |
| TSPAN12 | −10.1 | −5.3 | $2.0 \times 10^{-7}$ |

TABLE 2A

Names of differentially expressed genes.

| Gene abbreviation | Name |
| --- | --- |
| ALOX12 | Arachidonate 12-lipoxygenase |
| ALOX15 | Arachidonate 15-lipoxygenase |
| APOBEC3A | Apolipoprotein B mRNA editing enzyme catalytic subunit 3A |
| CDA | Cytidine deaminase |
| COL8A2 | Collagen type VIII alpha-2 chain |
| CRISP3 | Cysteine-rich secretory protein 3 |
| ENDOU | Endonuclease, poly(U)-specific |
| EPB41L3 | Erythrocyte membrane protein band 4.1 like 3 |
| GCNT3 | Glucosaminyl (N-acetyl) transferase 3, mucin-type |
| HILPDA | Hypoxia-Inducible Lipid Droplet Associated protein |
| IGFL1 | IGF-like family member 1 protein |
| PLAUR | Plasminogen Activator, Urokinase Receptor |
| SPINK7 | Serine-peptidase inhibitor, Kazel Type 7 (putative) |
| UPK1A | Uroplakin 1A |
| ZNF365 | Zinc finger protein 365 |
| ACTG2 | Actin, Gamma 2, Smooth Muscle |
| CCR3 | C-C motif chemokine receptor 3 |
| CLEC16A | C-type lectin domain containing 16A |
| FFAR3 | Free fatty acid receptor 3 |
| FKBP5 | FKBP prolyl isomerase 5 |
| HPGD5 | Hematopoietic prostaglandin D synthase |
| IL4 | Interleukin 4 |
| IL5RA | Interleukin 5 receptor subunit alpha |
| KRT23 | Keratin 23 |
| LRRC32 | Leucine-rich repeat containing 32 |
| MUC4 | Mucin 4, cell surface associated |
| NTRK1 | Neurotrophic receptor tyrosine kinase 1 |
| PTGFRN | Prostaglandin F2 receptor inhibitor |
| RGS9BP | Regulator of G-protein signaling 9 binding protein |
| RUNX2 | Runt-related transcription factor 2 |
| SAMSN1 | SAM domain, SH3 domain and nuclear localization signals 1 |
| TGFB1 | Transforming growth factor beta 1 |
| TSLP | Thymic stromal lymphopoietin |
| UPK1B | Uroplakin 1B |
| WDR36 | WD repeat domain 36 |
| ACPP | Acid phosphatate, prostate |
| CITED2 | Cbp/P300 Interacting Transactivator With Glu/Asp Rich Carboxy-Terminal Domain 2 |
| CTNNAL1 | Catenin alpha-like 1 |
| EML1 | Echinodermi Microtubule-Associated Protein Like 1 |
| FLG | Filaggrin |
| GRPEL2 | GrpE Like 2, Mitochondrial |
| MT1M | Metallothionein 1M |
| PNLIPRP3 | Pancreatic lipase-related protein 3 |
| TSPAN12 | Tetraspanin 12 |

The clinical and demographic characteristics (which were not included in the consensus Clustering) for each EoE endotype are described below and in FIG. 4. The 3 endotypes did not differ significantly by their peak eosinophil level, age at time of biopsy collection, gender, race, nor length of time since diagnosis of EoE to biopsy collection. To address whether the identified endotypes have histologic and endoscopic distinctions, we evaluated the association of each endotype with several disease parameters (peak eosinophil counts, EDP, HSS, and EREFS).

Figure 4A:
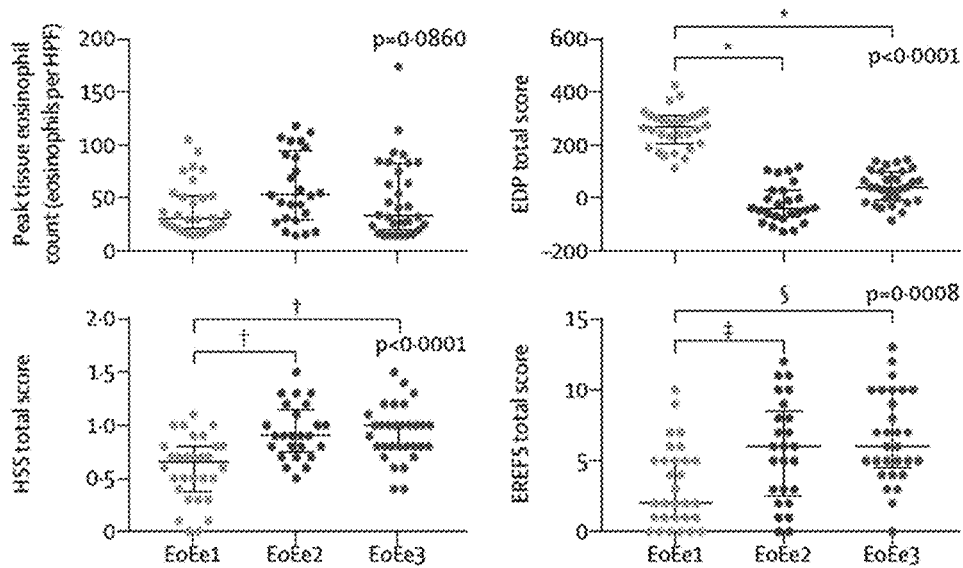
FIG. 4A-D: Clinical features of each eosinophilic esophagitis endotype. (A) Comparison of each eosinophilic esophagitis endotype by diagnostic platform, peak esophageal eosinophil count (upper left), EDP score (upper right), HSS score (lower left), and EREFS score (lower right). Centre line represents the median and error bars represent the IQR. Every dot represents an individual participant. p values at the top of each graph are calculated by the Kruskal-Wallis test, and p values indicated by symbols are calculated with Dunn's post-hoc test and are versus EoEe1. (B) Comparison of each HSS domain in each eosinophilic esophagitis endotype (upper) and each EREFS feature in each eosinophilic esophagitis endotype (lower). Data are mean (SE). p values at the top of each graph (for each feature) are calculated by the Kruskal-Wallis test, and p values indicated by symbols are calculated by Dunn's post-hoc test and are versus EoEe1. (C) Summary of significant associations for each endotype. (D) Multiple correspondence analysis of the relations between clinical phenotypes and endotypes. Dimension 1 represents the summation of the major variations, whereas Dimension 2 represents the minor variation for each data point. Distance between variables (phenotype and endotype) indicates the approximate relation between variables. The distance between variables is inversely proportional to the strength of the relation. Circles have been added to emphasize the proximity between points. BZH=basal zone hyperplasia. DEC=dyskeratotic epithelial cells. DIS=dilated intercellular spaces. EA=eosinophilic abscess. EDP=eosinophilic esophagitis diagnostic panel. EI=eosinophilic inflammation. EoEe=eosinophilic esophagitis endotype. EREFS=eosinophilic esophagitis endoscopic reference score. ESL=eosinophilic surface layering. HPF=high-power field. HSS=eosinophilic esophagitis histology scoring system. LPF=lamina propria fibres. RR=risk ratio. SEA=surface epithelial alteration. *p<0.0001. †p=0.0003. ‡p=0.0308. § p=0.0007. ¶p=0.0004. ‖p=0-0178. **p=0.0096. ††p=0-0017. ‡‡p=0-0317. §§ p=0.0163.
Figure 4B:
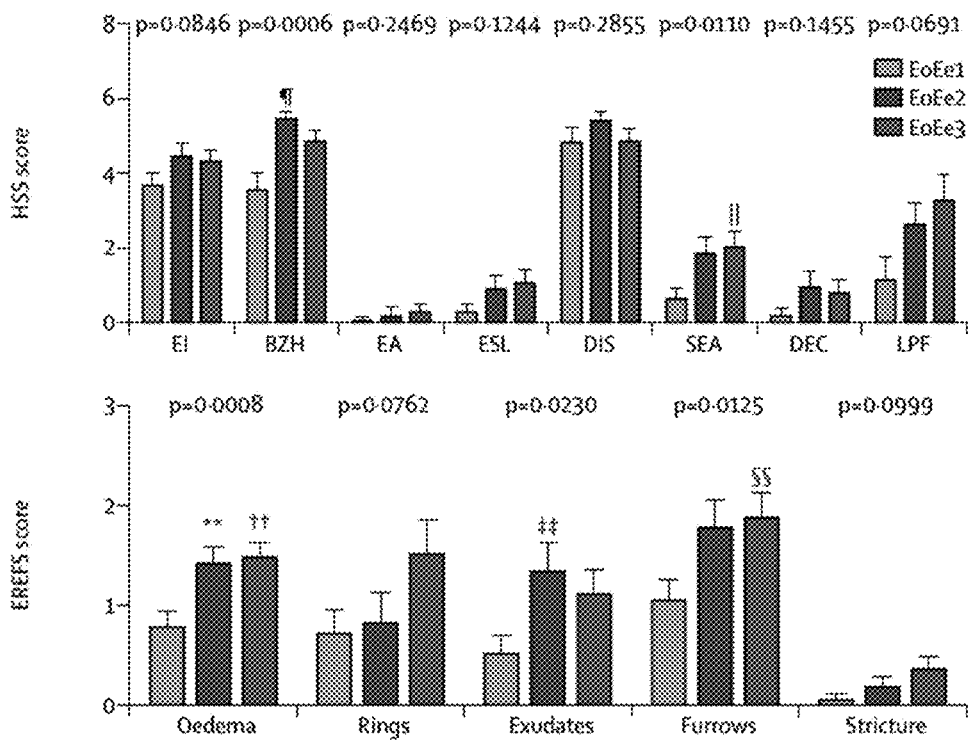

Notably, even though there was no difference in peak eosinophil counts among the endotypes, EDP, HSS, and EREFS parameters were associated with endotype classification (FIG. 4A). Among the HSS domains, the BZH and surface epithelial alteration (SEA) domains showed the most significant association with endotype (FIG. 4B). BZH was significantly higher in EoEe2 compared to EoEe1 (p=0.0004), whereas SEA was significantly higher in EoEe3 compared to EoEe1 (p=0.0178). Among the EREFS features, edema, exudates, and furrows showed significant association with endotypes (FIG. 4B). Endoscopic edema was significantly higher in EoEe2 and EoEe3 compared to EoEe1 (p=0.0096 and p=0.0017, respectively). Occurrence of exudates was significantly higher in EoEe2 compared to EoEe1 (p=0.0317), whereas occurrence of furrows was significantly higher in EoEe3 compared to EoEe1 (p=0.0163).

Figure 4C:
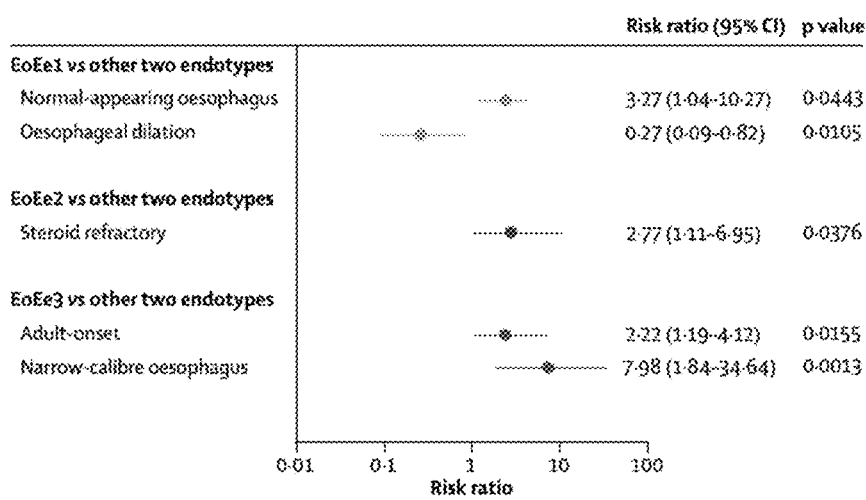
Figure 4D:
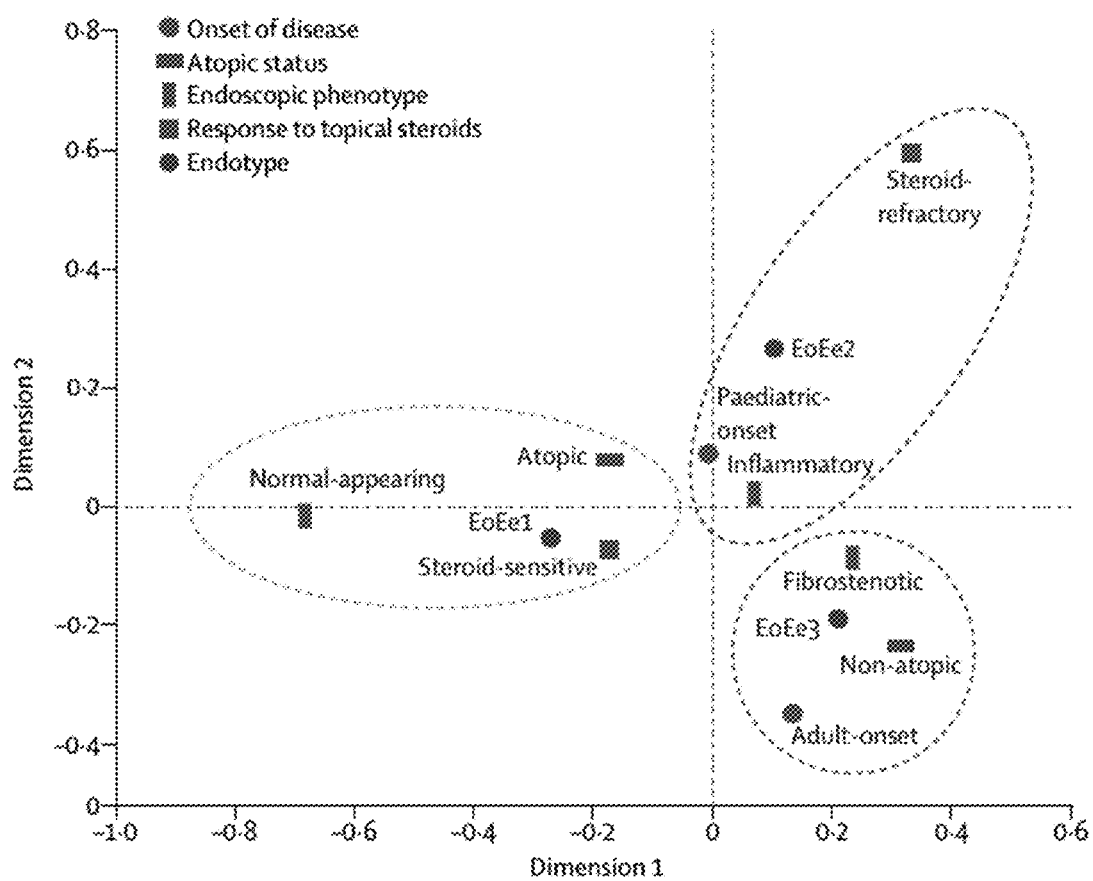

To determine which clinical characteristics were specific to each endotype, logistic regression analysis was performed. From logistic regression modeling adjusted by age at time of biopsy, we observed strong associations between EoEe1 and normal-appearing esophagus (aOR=4.96 [95% CI 1.12–22.02]; p=0.035), EoEe2 and steroid refractory (aOR=4 0.91 [95% CI 1.19-20.30]; p=0.028), and EoEe3 and the presence of narrow-caliber esophagus (aOR=10.08 [95% CI 1.96-51.83]; p=0.006) (FIG. 4C). MCA was performed to demonstrate the pattern of the endotypes with regards to clinical features (FIG. 4D). EoEe1 was situated near atopic, pediatric-onset, steroid-sensitivity, and normal endoscopic appearance. EoEe2 was situated close to inflammatory and steroid-resistance, whereas EoEe3 was located near non-atopic, adult-onset, and fibrostenotic phenotypes.

To facilitate potential translation to clinical practice, a clinically reproducible method to identify endotypes was developed. Briefly, stepwise discriminant analysis was performed using the stepwise forward selection method. The discovery cohort was split into training (75%) and testing sets (25%) by random selection, estimation of the variables in the training set and classification of the testing set. Variables were selected from the EDP genes based on a p-value of 0.05 to determine which variables (if any) to include in the discriminating function and whether some of the entered variables should be excluded from the model. The procedure continued until none of the excluded variables had a p-value below the threshold and none of the entered variables had a p-value above the threshold (the stopping rule was applied).

Figure 5A:
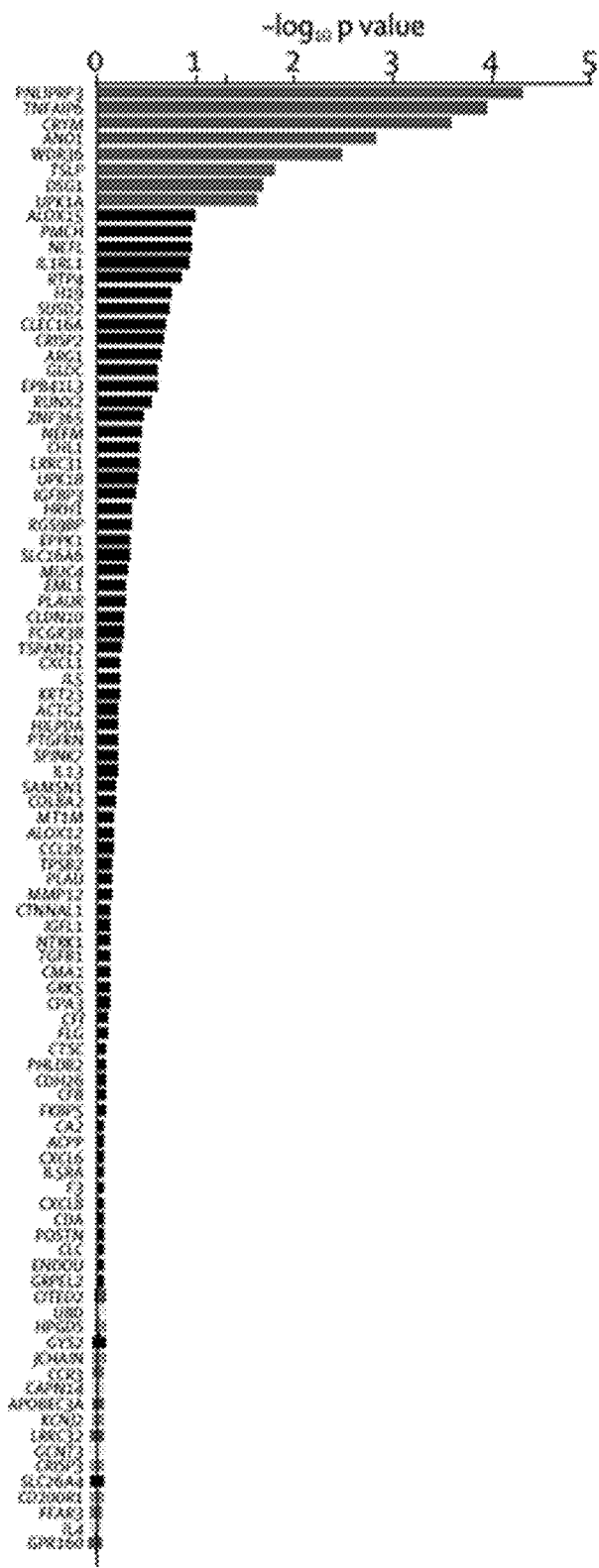
FIG. 5A-J: Eosinophilic esophagitis endotype prediction based on machine learning with high accuracy. (A) Stepwise discriminant analysis shows the eight strongest discriminatory genes for cluster assignment (red bars). (B) Canonical plot in which participants are plotted in a two-dimensional space. Every dot represents an individual participant. Canonical 1 represents the summation of major variations, whereas Canonical 2 represents the minor variation for each data point. A 95% CI ellipse (inner) and an ellipse denoting a 50% contour (outer) are plotted for each group. The flow of the analysis is plotted in the lower diagram. Diagnostic accuracy is summarized in the right-hand table. EDP=eosinophilic esophagitis diagnostic panel. EoEe=eosinophilic esophagitis endotype. NPV=negative predictive value. PPV=positive predictive value. (C-J) Gene expression measured as delta Ct in each endotype for PNLIPRP3 (C), CRYM (D), WDR36 (E), DSG1 (F), TSLP (G), TNFAIP6 (H), ANO1 (I), and UPK1A (J). Comparison of continuous variables between diagnostic groups was performed by Wilcoxon/Kruskal-Wallis tests (rank sums), using nonparametric comparison for all pairs using Dunn method for joint ranking.

Stepwise linear discriminant analysis using the same 96 EDP genes for active EoE (including EoEe1-3) identified the 8 strongest discriminatory genes as PNLIPRP3, CRYM, WDR36, DSG1, TSLP, TNFAIP6, ANO1, and UPK1A (FIG. 5A). Using these 8 genes, 84 (98%) patients in the discovery cohort were assigned to the appropriate endotype. The three endotypes were discriminated well from each other with good diagnostic accuracy (FIG. 5B).

Figure 5B:
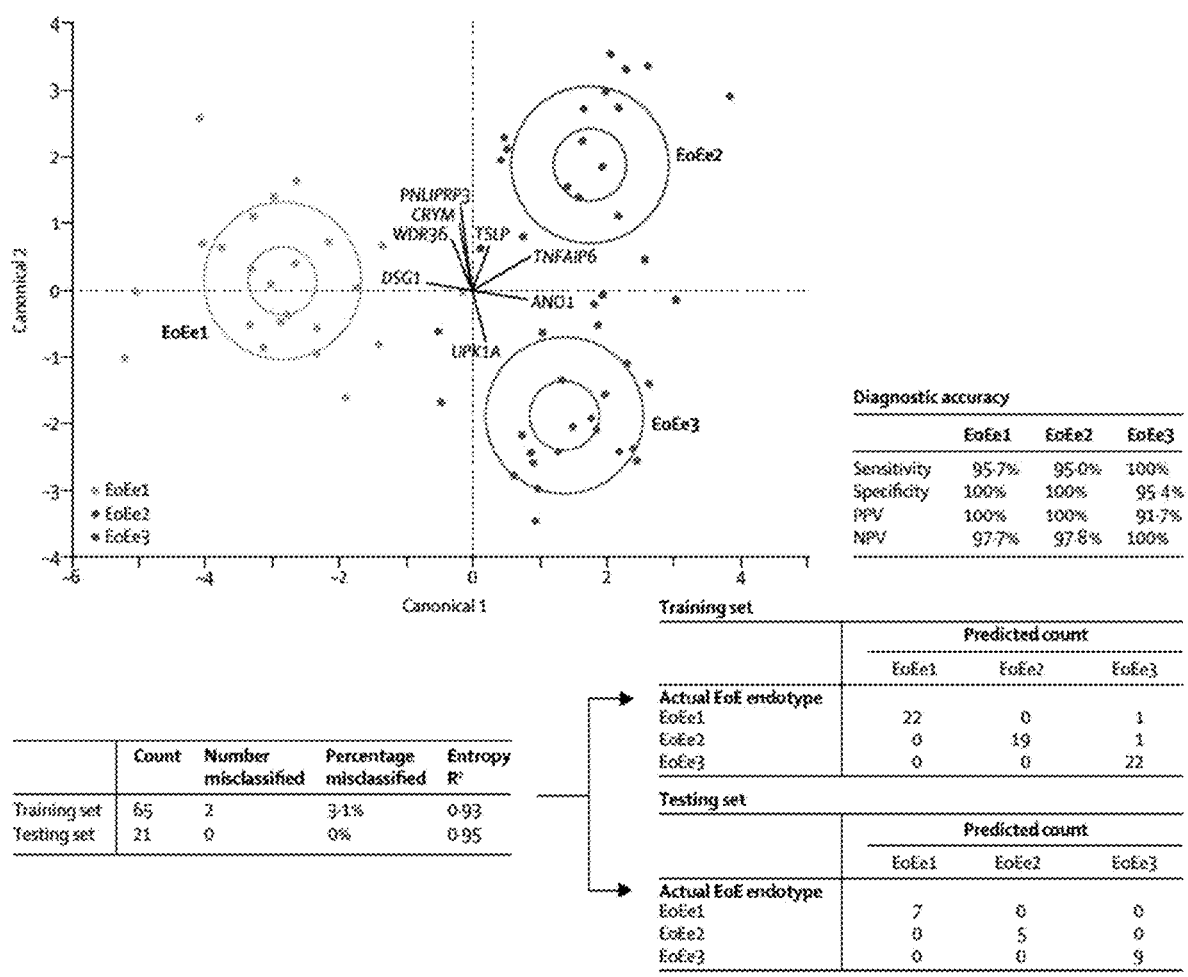
Figure 5C:
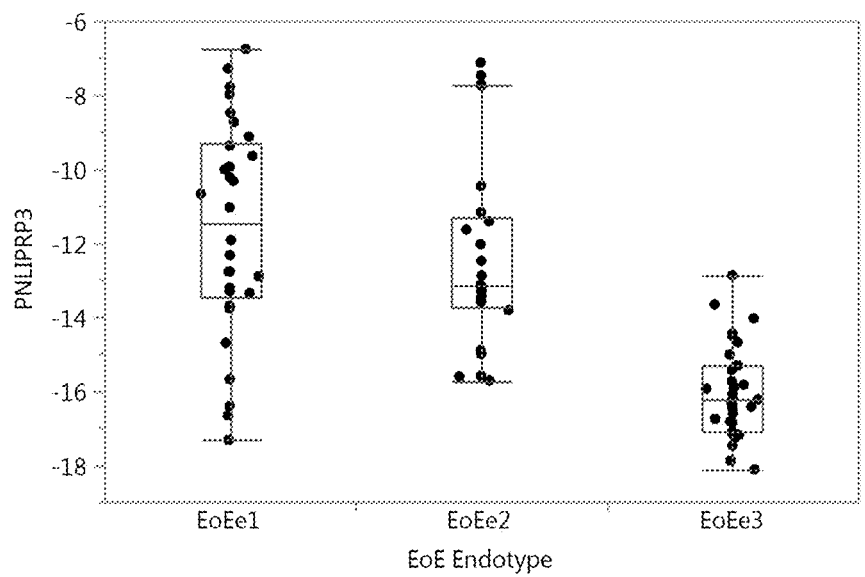
Figure 5D:
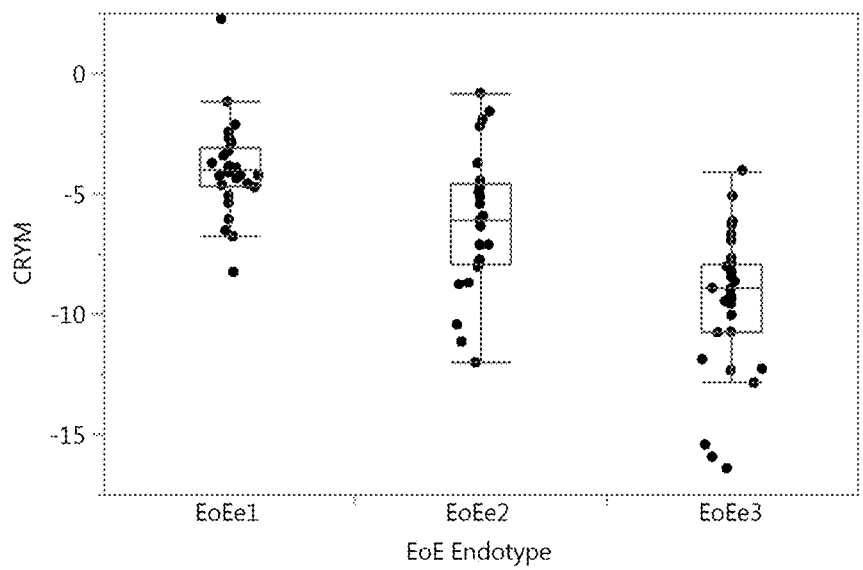
Figure 5E:
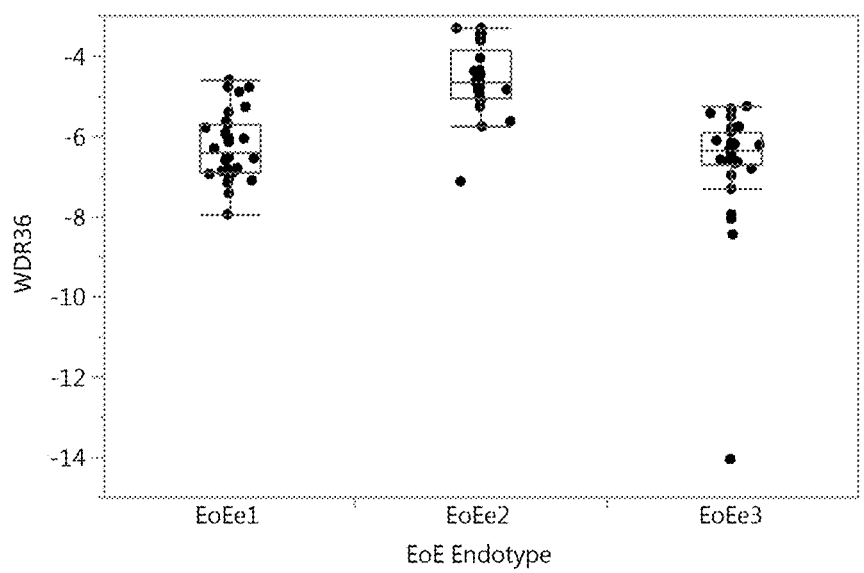
Figure 5F:
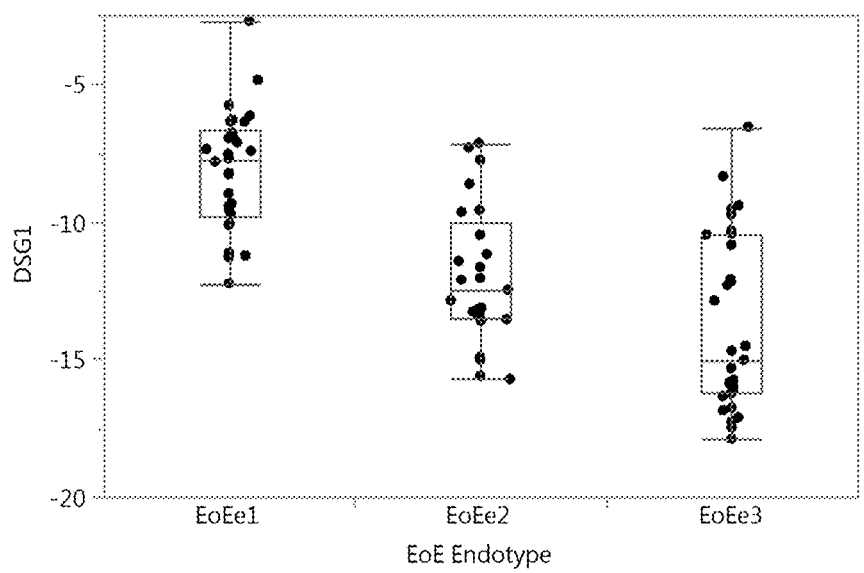
Figure 5G:
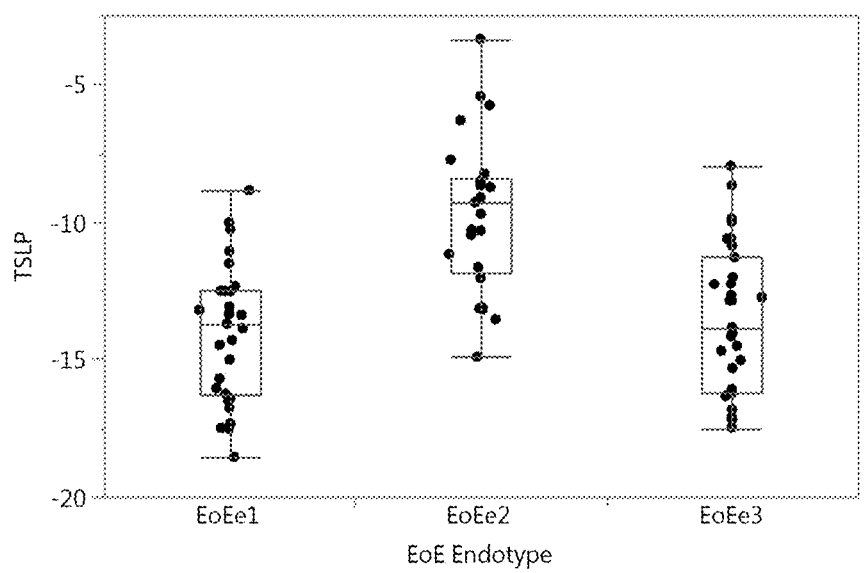
Figure 5H:
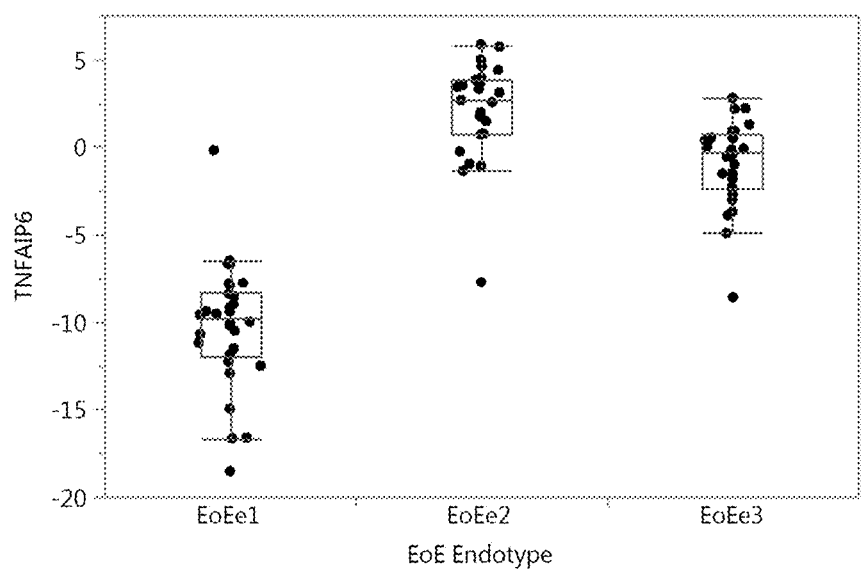
Figure 5I:
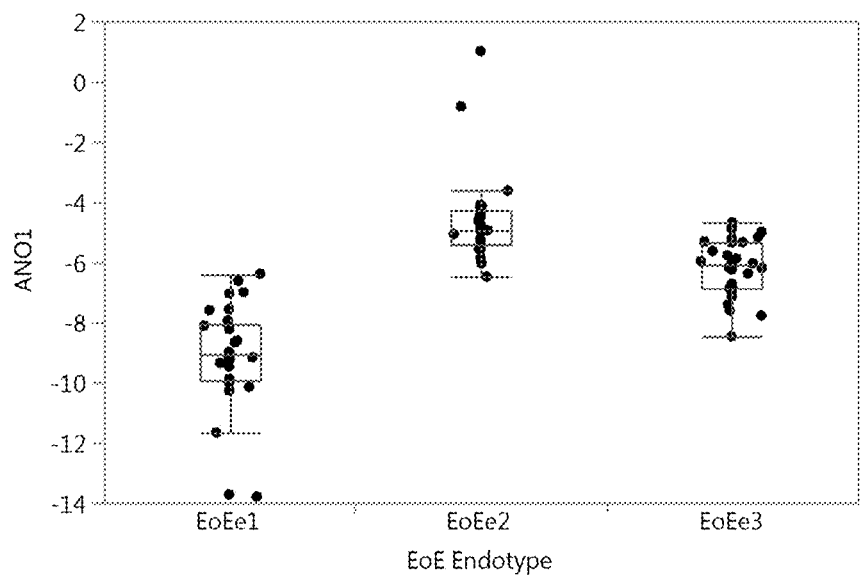
Figure 5J:
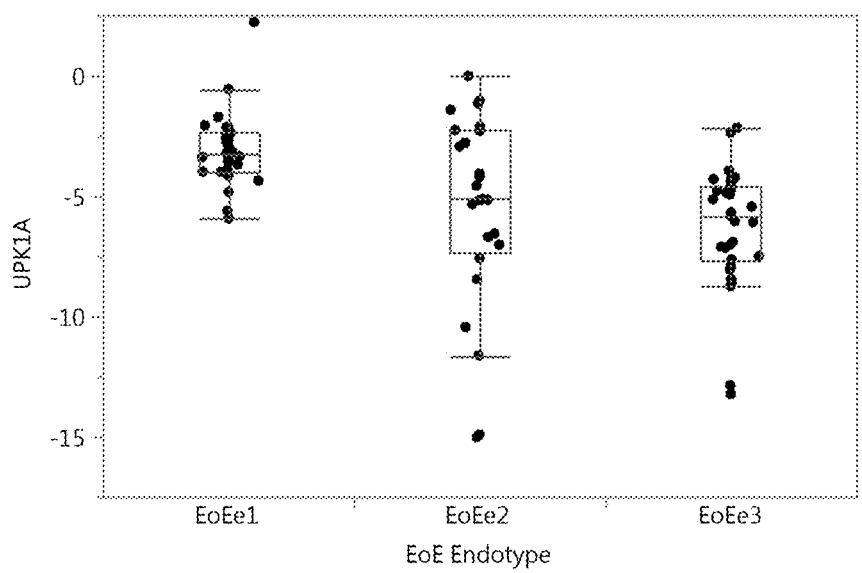

FIG. 5B shows a canonical biplot based on a linear discriminant analysis to predict endotype classification based on the observed continuous variables, or covariates, of gene expression. Gene expression for each endotype is shown in FIG. 5C-J.

In FIG. 5B, the biplot axes are the first two canonical variables which define the two dimensions providing maximum separation between endotypes. Each canonical variable is a linear combination of the gene expression covariates. The biplot shows how each subject is represented in terms of canonical variables and how each covariate contributes to the canonical variables. The subjects are represented as points on the biplot and are expressed in terms of the first two canonical variables. A 95% confidence level ellipse is plotted for each mean. If two groups differ significantly, the confidence ellipses tend not to intersect. An ellipse denoting a 50% contour is plotted for each group. This depicts a region in the space of the first two canonical variables that contains approximately 50% of the observations, assuming normality. The set of rays that appears in the plot represents the gene expression covariates. For each canonical variable, the coefficients of the gene expression covariates in the linear combination can be interpreted as weights. To facilitate comparisons among the weights, the gene expression covariates are standardized so that each has a mean of 0 and standard deviation of 1. The coefficients for the standardized covariates are referred to as the canonical weights. The larger a covariate's canonical weight, the greater its association with the canonical variable. The length of each ray is a multiple of the canonical weight. The rays emanate from the point (0,0), which represents the grand mean of the data in terms of the canonical variables. The length and direction of each ray in the biplot indicates the degree of association of the corresponding covariate with the first two canonical variables. Thus, the length and direction of each ray indicates the degree of association of gene expression with the canonical variables. Comparison of continuous variables between diagnostic groups was performed by Wilcoxon/Kruskal-Wallis tests (rank sums), using nonparametric comparison for all pairs using Dunn method for joint ranking, as shown in FIG. 5C-5J.

To further validate the eosinophilic esophagitis endotype findings, the same analysis was done in the validation cohort, which comprised 100 patients with active eosinophilic esophagitis. Two separate strategies (consensus clustering based solely on the EDP, and endotype prediction based on the highly discriminatory genes) were used for assignment of endotype, then the validation cohort was compared with the discovery cohort. For validation of endotypes by clustering, 60 patients were segregated into the three endotypes with optimum quality and stability. The remaining 40 patients were assigned to one of the three endotypes based on results of the endotype-prediction algorithm developed with the discovery cohort. The endotypes generated from the validation cohort were like those generated from discovery cohort, in that the gene expression relations among the endotypes were maintained. Furthermore, differences in eosinophilic esophagitis scores and several gene expression levels among the endotypes were similar between validation and discovery cohorts. In the validation cohort, peak eosinophil counts among the three endotypes did not differ. Moreover, consistent with the discovery cohort, the three endotypes showed similar differential trends in clinical and endoscopic findings.

DISCUSSION

Herein, we have dissected EoE disease molecular heterogeneity via the EoE EDP, across a multi-site cohort of subjects associated with CEGIR, and assessed its relevance using a combination of standardized histologic, endoscopic, and clinical platforms. First, we demonstrated that the EDP showed consistency across sites, had similar findings between pediatric and adult EoE subjects, and correlated with esophageal eosinophil levels. Second, we report the existence of three disease endotypes and present evidence for their clinical, histologic and endoscopic significance. Notably, these disease endotypes remained stable using distinct statistical methodology including unsupervised clustering, 3-dimensional principal component analysis (PCA), and cumulative distribution functionality. Third, disease endotypes occurred independent of peak eosinophil counts, underscoring that these findings surpass information provided by eosinophil counts, consistent with prior findings that disease severity and clinical symptoms do not simply reflect eosinophil levels. Fourth, focusing on the unique features of the disease endotypes, we report that EoEe1 has the mildest phenotype, most closely resembling findings seen in healthy tissue of normal biopsies; EoEe2 is characterized by substantial inflammatory changes, type-2 immune responses, and evidence of refractoriness to steroids; and EoEe3 shows a strong association with the presence of a narrow-caliber esophagus, the highest degree of endoscopic and histologic severity, and the lowest expression of epithelial differentiation genes. Fifth, we demonstrate that machine learning can be used to reproducibly separate disease endotypes. Six, we have uncovered a strong association between eosinophilic inflammation, BZH, and endoscopic furrowing. Lastly, we have identified genes that are modulated within each of the endotypes, establishing insight into distinct disease mechanisms Collectively, the new endotypes described here stratify patients with EoE into subgroups with clinical and therapeutic significance, thereby providing a framework for a precision medicine approach to EoE therapy. For example, because fibrostenotic eosinophilic esophagitis is typically steroid resistant, EoEe2 and EoEe3 likely represent more complex or severe phenotypes and could benefit from treatments in addition to, or even instead of inflammatory control. By uncovering three distinct disease endotypes, each associated with different clinical features, and importantly, molecular pathways and hence mechanisms, our findings provide a framework for distinct prognostic medicine and therapeutic intervention strategies targeted to specific EoE patient subpopulations.

In the present study, we highlighted the strong association between the EDP, the HSS and the EREFS, which are important assessments of disease severity. The overall EDP exhibited the strongest association with the basal zone hyperplasia (BZH) domain. This is consistent with recent work by others suggesting a substantial role of the basal epithelium, particularly related to loss of cellular differentiation. We also found that the endoscopic finding of furrowing stands out as a unique feature, related to transcript changes, particularly those involved in inflammatory responses. Of note, this association was consistent across age groups, even though it is well recognized that clinical and endoscopic features differ between children and adults.

To our knowledge, the present study is the first to characterize endotypes in EoE. EoEe1, representing 35% of patients, had relatively small changes in epithelial differentiation genes, a pauci-inflammatory state, and a greater proportion of normal-appearing esophagus by endoscopy. EoEe2, representing 29% of patients, had particularly high type-2 immune response mechanisms and a steroid-refractory phenotype. EoEe3, representing 36% of patients, had particularly low expression of epithelial differentiation genes and a greater frequency of narrow-caliber esophagus. Endotypes were associated with distinct clinical features, including pediatric-onset versus adult-onset EoE (EoEe1 and EoEe2 vs. EoEe3), atopic versus non-atopic (EoEe1 and EoEe2 vs. EoEe3), normal versus inflammatory versus fibrostenotic endoscopic appearance (EoEe1 vs. EoEe2 vs. EoEe3), and steroid-sensitive versus steroid-refractory (EoEe1 vs EoEe2 and EoEe3).

Our study demonstrates that EoE populations are molecularly and biological distinct and thus has implications for targeting therapy to specific subgroups. EoEe1 is characterized by markedly low expression of ALOX15, suggesting that this gene may be associated with a more severe phenotype and that its suppression and/or suppression of the metabolic products of 15-lipoxygenase may be therapeutic, particularly in subjects with EoEe2 or EoEe3. EoEe2 is characterized by a pronounced inflammatory response, observed by endoscopy and molecular transcript profiling. EoEe2 transcript profiles are notable for relatively high expression of a variety of pro-inflammatory cytokines, especially those characterized by type-2 immune responses (e.g., IL-4 and TSLP). The highest relative expression is seen in the ACTG2 gene, encoding for the actin gamma smooth muscle 2 protein. This protein has been shown to be involved in epithelial cell responses including mesenchymal transition, which is observed in EoE. EoEe3 is enriched for epithelial genes that lose expression, particularly ACPP, CITED2, CTNNAL1, EML1, FLG, GRPEL2, MT1M, PNLIPPR3 and TSPAN12. This is the first molecular analysis of the fibrostenotic disease group and provides pathogenic insight and potential points of therapeutic intervention for this difficult-to-treat EoE subgroup. For example, TSPAN12 is tetraspan protein involved in epithelial cell contact, proliferation, and migration and therefor represents a promising therapeutic target.

Our findings also suggest distinct therapeutic strategies for patients falling within each of the endotypes described here. For example, our results indicate that EoEe2 is relatively more responsive to specific anti-type-2 immune therapies, such as anti-IL-4Ra, rather than anti-IL-13 therapy, which shows less differentiation between the three endotypes. Taken together with recent work by others suggesting the presence of a subgroup having a T-helper-2-type inflammatory profile with high expression of TSLP (Lexmond W S, et al. Clin Exp Allergy 2013; 43(8): 902-13), the present findings also indicate that EoEe2 patients represent a subgroup that will be responsive to anti-TSLP therapy. Our findings also indicate that pediatric and adult EoE have comparable pathogenesis and therefor are likely to be similarly responsive to therapy.

A growing body of evidence supports the reassessment of clinical trial designs to include biomarkers reflecting the status of the host response. The molecular endotypes described here show that EoE presents heterogeneously with distinct pathophysiologic profiles that are not distinguishable by esophageal eosinophil counts alone. This has potential value for future clinical trials that could stratify participants prospectively or retrospectively to identify subgroups with distinct responsiveness to therapy. In addition, by deriving machine learning prediction for each endotype, we provided evidence that molecular subtyping of subjects with EoE is feasible in clinical practice and that the technology to produce such tests with automated generation of results exists.

In conclusion, we have established that at least three EoE endotypes exist, each having distinct features of gene expression, histology, and endoscopy, that correlate with clinical features and can be used to stratify patients for personalized therapy.

Study Design and Participants

This study was done within the wider context of CEGIR, which is part of Rare Diseases Clinical Research Network (RDCRN) of the National Institutes of Health. For the discovery cohort, between 2015-2017, children and adults with EoE (≥3 years of age) were enrolled in a multicenter prospective observational study associated with CEGIR. Data were entered and managed by the Data Management and Monitoring Center (DMCC) associated with the RDCRN. Subjects with EoE were defined as having symptomatic esophageal dysfunction and a peak count of 15 or more esophageal eosinophils/HPF. For the validation cohort, children and adults with EoE (≥3 years of age) presenting for standard of care were enrolled in an independent, local Cincinnati cohort. Subjects in the validation cohort were not in the discovery cohort. This study was approved by the institutional review boards of the participating institutions via a central institutional review board at Cincinnati Children's Hospital Medical Center.

Procedures

Transcriptomic signatures in distal esophageal biopsy samples were obtained using an EDP as previously reported. Histologic and endoscopic features were assessed by peak eosinophil counts, the EoE HSS, and EREFS. Clinical features of subjects were captured across sites by the CEGIR questionnaires, which include self-reported demographic, race/ethnicity, exposure assessments, and clinical variables. Clinical phenotypes were defined using metrics previously reported. In addition, steroid-sensitivity/-resistance was determined using a positive/negative response, respectively, to whether swallowed topical steroids have been effective on the basis of pathology (see the REGID [Registry for Eosinophilic Gastrointestinal Disease] questionnaire in the appendix p 29-30).

We evaluated the associations between peak eosinophil counts and disease parameters (EDP, HSS, and EREFS). Furthermore, the EDP (either as a whole or individual genes) was examined for association with the HSS and EREFS features. Spearman correlation analysis was performed between the gene expression levels on the EDP and the HSS and EREFS features.

EDP data from subjects with active EoE were further examined by an unbiased/unsupervised clustering. Consensus clustering was performed by the partition-around-medoids (PAM) algorithm with the Euclid distances metric. Bootstrapping was performed by randomly removing 10% of the data and repeating the clustering a total of 1,000 times. To assess the optimal number of clusters, stability was assessed by the cumulative distribution function (CDF), cluster-consensus (CLC) values, and silhouette width analysis. To identify specific clinical associations for each cluster, logistic regression modeling adjusted by age at biopsy, which could act as potential confounder, was performed. Multiple correspondence analysis (MCA) was also performed to present the pattern of relationships among each cluster and several phenotypes. To develop the algorithm for identifying EoE endotypes, stepwise linear discriminant analysis was performed with a stepwise selection method. The diagnostic performance of the algorithm was evaluated by receiver operator characteristic (ROC) analyses to calculate the area under the curve (AUC). Results were validated with a validation cohort.

The primary objectives of this study were to establish the relationships between various endoscopic, histologic, and molecular features and to determine whether EoE endotypes exist and their significance in terms of histologic, endoscopic, and clinical features.

Statistical Analysis

Data are n (%) or median (interquartile range [IQR]) unless otherwise stated. Statistical analyses were done using the JMP v13-0 (SAS Institute, Cary, NC), GeneSpring GX 12.6 (Agilent Technologies, Santa Clara, CA), GraphPad Prism 7 (GraphPad Software, Inc., San Diego, CA), and the R statistical computing environment (version 3.1.2). Correlation analysis was done using Spearman's rank correlation coefficient followed by Bonferroni adjustment. Adjusted odds ratio (aOR) and 95% confidence intervals (CI) were calculated for each endotype with reference to all other endotypes. To compare differences between endotypes, the Kruskal-Wallis with the Dunn's multiple comparison test were used for nonparametric, continuous variables and the chi-square tests for nonparametric, categorical variables. A significant p value was defined as less than 0.05.

EQUIVALENTS

Those skilled in the art will recognize or be able to ascertain using no more than routine experimentation, many equivalents to the specific embodiments of the invention described herein. Such equivalents are intended to be encompassed by the following claims.

All references cited herein are incorporated herein by reference in their entirety and for all purposes to the same extent as if each individual publication or patent or patent application was specifically and individually indicated to be incorporated by reference in its entirety for all purposes.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. A method for treating eosinophilic esophagitis (EoE) in a subject determined to have a severe form of EoE, the method comprising
subjecting a biological sample from the subject to a method for gene expression analysis,
determining the expression of a panel of genes in the biological sample, the panel comprising ACPP, CITED2, CTNNAL1, EML1, FLG, GRPEL2, MT1M, PNLIPRP3, and TSPAN12,
determining the subject's EoE endotype is severe based on the expression of the panel of genes, wherein a decrease in expression of one or more of CTNNAL1, EML1, FLG, PNLIPRP3, and TSPAN12 by at least 2-fold compared to a reference indicates the subject's EoE endotype is severe,
and
treating the patient with an EoE therapy comprising one or more of esophageal dilation, anti-cytokine therapy, and glucocorticoid therapy.

2. The method of claim 1, wherein the biological sample is an esophageal biopsy sample.

3. The method of claim 1, wherein the determining the expression of a panel of genes in the biological sample is performed using a PCR-based method.

4. The method of claim 1, wherein the determining the subject's EoE endotype based on the expression of the panel of genes is performed by a method comprising linear discriminant analysis.

5. The method of claim 4, wherein the linear discriminant analysis comprises determining a probability distance.

6. The method of claim 5, wherein the distance is the Mahalanobis distance.

7. The method of claim 1, wherein the endotype is further characterized by one or more histologic, endoscopic, or clinical features.

8. The method of claim 7, wherein the one or more histologic features is selected from basal zone hyperplasia (BZH) and surface epithelial alteration (SEA).

9. The method of claim 7, wherein the one or more endoscopic features is selected from the occurrence of edema, exudates, and furrows.

10. The method of claim 7, wherein the one or more clinical features is selected from pediatric onset, adult onset, atopic, non-atopic, steroid sensitivity, steroid refractory, and fibrostenotic.

11. A method for treating eosinophilic esophagitis (EoE) in a subject in need thereof, the method comprising
subjecting a biological sample from the subject to a method for gene expression analysis,
determining the expression of a panel of genes in the biological sample, the panel comprising ACTG2, CCR3, FFAR3, IL4, RGS9BP, and TSLP,
determining the subject's EoE endotype is intermediate based on the expression of the panel of genes, wherein an increase in expression of one or more of ACTG2, CCR3, FFAR3, IL4, RGS9BP, and TSLP by at least 2-fold compared to a reference indicates the subject's EoE endotype is intermediate,
and
treating the patient with an EoE therapy comprising one or more of anti-cytokine therapy and anti-TSLP therapy, but not glucocorticoid therapy.

12. The method of claim 11, wherein the biological sample is an esophageal biopsy sample.

13. The method of claim 12, wherein the determining the expression of a panel of genes in the biological sample is performed using a PCR-based method.

14. The method of claim 13, wherein the determining the subject's EoE endotype based on the expression of the panel of genes is performed by a method comprising linear discriminant analysis.

15. A method for treating eosinophilic esophagitis (EoE) in a subject in need thereof, the method comprising
subjecting a biological sample from the subject to a method for gene expression analysis,
determining the expression of a panel of genes in the biological sample, the panel comprising ALOX15, APOBEC3A, CDA, and CRISP3,
determining the subject's EoE endotype is mild based on the expression of the panel of genes, wherein a decrease in expression of one or both of ALOX15 and APOBEC3A by at least 2-fold compared to a reference and an increase in expression of one or both of CDA and CRISP3 indicates the subject's EoE endotype is mild,
and
treating the patient with an EoE therapy comprising one or both of proton pump inhibitor (PPI) therapy and dietary therapy.

16. The method of claim 15, wherein the biological sample is an esophageal biopsy sample.

17. The method of claim 16, wherein the determining the expression of a panel of genes in the biological sample is performed using a PCR-based method.

18. The method of claim 17, wherein the determining the subject's EoE endotype based on the expression of the panel of genes is performed by a method comprising linear discriminant analysis.

* * * * *